US00H002074H

(19) United States

(12) Statutory Invention Registration (10) Reg. No.: US H2074 H

Lundquist et al. (43) Published: Jul. 1, 2003

(54) FERTILE TRANSGENIC CORN PLANTS

(75) Inventors: Ronald C. Lundquist, Minnetonka, MN (US); David A. Walters, Bloomington, MN (US); Julie A. Kirihara, Bloomington, MN (US)

(73) Assignee: DeKalb Genetics Corporation, Dekalb, IL (US)

(21) Appl. No.: 08/679,001

(22) Filed: Jul. 12, 1996

Related U.S. Application Data

(62) Division of application No. 08/618,749, filed on Mar. 20, 1996, now Pat. No. 5,780,708, which is a division of application No. 08/285,488, filed on Aug. 3, 1994, now Pat. No. 5,508,468, which is a continuation-in-part of application No. 07/974,379, filed on Nov. 10, 1992, now Pat. No. 5,538,877, which is a continuation of application No. 07/636,089, filed on Dec. 28, 1990, now abandoned, which is a continuation-in-part of application No. 07/508,045, filed on Apr. 11, 1990, now Pat. No. 5,484,956, which is a continuation of application No. 07/467,983, filed on Jan. 22, 1990, now abandoned.

(51) Int. Cl.[7] ..... A01H 5/00; A01H 1/00; C07H 21/04

(52) U.S. Cl. ..... 800/320; 800/301; 800/302; 800/303; 800/278; 536/24.1

(58) Field of Search ..... 800/205, 200, 800/250, DIG. 56, 320, 301, 302, 303; 435/172.3, 172.1; 935/66, 67; 536/24.1

(56) References Cited

U.S. PATENT DOCUMENTS

| | | | | |
|---|---|---|---|---|
| 4,370,160 | A | 1/1983 | Ziemelis | 71/117 |
| 4,399,216 | A | 8/1983 | Axel et al. | 435/6 |
| 4,520,113 | A | 5/1985 | Gallo et al. | 436/504 |
| 4,535,060 | A | 8/1985 | Comai | 435/172 |
| 4,536,475 | A | 8/1985 | Anderson | 435/172.3 |
| 4,559,301 | A | 12/1985 | Turner | 435/76 |
| 4,559,302 | A | 12/1985 | Turner | 435/76 |
| 4,581,847 | A | 4/1986 | Hibberd et al. | 47/58 |
| 4,634,665 | A | 1/1987 | Axel et al. | 435/68 |
| 4,642,411 | A | 2/1987 | Hibberd et al. | 800/1 |
| 4,665,030 | A | 5/1987 | Close | 435/240 |

(List continued on next page.)

FOREIGN PATENT DOCUMENTS

| | | | |
|---|---|---|---|
| AU | 80893/87 | 12/1988 | C12N/15/00 |
| DE | 37 38 847 A1 | 11/1988 | A01H/1/06 |

(List continued on next page.)

OTHER PUBLICATIONS

Andrews et al. Biochem J. vol. 252, pp. 199–206, 1988.*

Jaynes et al. TIB 4(12) pp 314–320, 1986.*

Dure III, L., et al., "Common Amino Acid Sequence Domains Among the LEA Proteins of Higher Plants", *Plant Molecular Biology*, 12, 475–486 (1989).

(List continued on next page.)

*Primary Examiner*—Charles T. Jordan

*Assistant Examiner*—Aileen J. Baker

(74) *Attorney, Agent, or Firm*—Schwegman Lundberg Woessner & Kluth

(57) ABSTRACT

Fertile transgenic *Zea mays* (corn) plants which stably express recombinant DNA which is heritable are provided wherein said DNA preferably comprises a recombinant gene which encodes a seed storage protein, so that the amino acid profile of the corn is improved.

9 Claims, 8 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | | | |
|---|---|---|---|---|---|
| 4,666,844 | A | | 5/1987 | Cheng | 435/240 |
| 4,683,202 | A | | 7/1987 | Mullis | 435/91 |
| 4,708,818 | A | | 11/1987 | Montagnier et al. | 435/5 |
| 4,727,028 | A | | 2/1988 | Santerre et al. | 435/240 |
| 4,743,548 | A | | 5/1988 | Crossway et al. | 435/172 |
| 4,761,373 | A | | 8/1988 | Anderson et al. | 435/172.3 |
| 4,806,483 | A | | 2/1989 | Wang | 435/240 |
| 4,885,357 | A | | 12/1989 | Larkins et al. | 530/373 |
| 4,886,878 | A | | 12/1989 | Larkins et al. | 536/26 |
| 4,940,835 | A | | 7/1990 | Shah et al. | 800/205 |
| 4,945,050 | A | | 7/1990 | Sanford et al. | 435/172.1 |
| 4,956,282 | A | | 9/1990 | Goodman et al. | 435/69.51 |
| 4,971,908 | A | | 11/1990 | Kishore et al. | 435/172 |
| 5,001,060 | A | | 3/1991 | Peacock et al. | 435/172 |
| 5,004,863 | A | | 4/1991 | Umbeck | 800/205 |
| 5,013,658 | A | | 5/1991 | Dooner et al. | 435/172.3 |
| 5,015,580 | A | | 5/1991 | Christou et al. | 435/172 |
| 5,034,322 | A | | 7/1991 | Rogers et al. | 435/172 |
| 5,036,006 | A | | 7/1991 | Sanford et al. | 435/170.1 |
| 5,049,500 | A | | 9/1991 | Arnizen et al. | 435/172 |
| 5,077,399 | A | | 12/1991 | Brauer et al. | 536/27 |
| 5,082,767 | A | | 1/1992 | Hatfield et al. | 435/6 |
| 5,094,945 | A | | 3/1992 | Comai | 435/172 |
| 5,097,093 | A | | 3/1992 | Vandeventer et al. | 800/200 |
| 5,110,732 | A | | 5/1992 | Benfey et al. | 435/172 |
| 5,134,074 | A | | 7/1992 | Gordon et al. | 435/240 |
| 5,145,777 | A | | 9/1992 | Goodman et al. | 435/172.3 |
| 5,164,310 | A | | 11/1992 | Smith et al. | 435/172.3 |
| 5,177,010 | A | | 1/1993 | Goldman et al. | 435/172 |
| 5,187,073 | A | | 2/1993 | Goldman et al. | 435/172 |
| 5,187,267 | A | | 2/1993 | Comai et al. | 536/23.1 |
| 5,188,642 | A | | 2/1993 | Shah et al. | 47/58 |
| 5,188,958 | A | | 2/1993 | Moloney et al. | 435/240 |
| 5,196,342 | A | | 3/1993 | Donovan | 435/320.1 |
| 5,215,912 | A | | 6/1993 | Hoffman | 435/240.4 |
| 5,240,841 | A | | 8/1993 | Johnston et al. | 435/172.3 |
| 5,250,515 | A | | 10/1993 | Fuchs et al. | 514/12 |
| 5,254,799 | A | | 10/1993 | Degrave et al. | 800/205 |
| 5,258,300 | A | | 11/1993 | Glassman et al. | 435/240 |
| 5,268,463 | A | | 12/1993 | Jefferson | 536/23 |
| 5,273,894 | A | | 12/1993 | Strauch et al. | 435/129 |
| 5,276,268 | A | | 1/1994 | Strauch et al. | 800/205 |
| 5,278,325 | A | | 1/1994 | Strop et al. | 554/12 |
| 5,290,924 | A | | 3/1994 | Last et al. | 536/241 |
| 5,302,523 | A | | 4/1994 | Coffee et al. | 435/172 |
| 5,310,667 | A | | 5/1994 | Eichholtz et al. | 435/172.3 |
| 5,350,689 | A | | 9/1994 | Shillito et al. | 435/240 |
| 5,352,605 | A | | 10/1994 | Fraley et al. | 435/240 |
| 5,371,003 | A | | 12/1994 | Murry et al. | 435/172 |
| 5,371,015 | A | | 12/1994 | Sanford et al. | 435/287 |
| 5,380,831 | A | | 1/1995 | Adang et al. | 536/23.71 |
| 5,384,253 | A | | 1/1995 | Krzyzek et al. | 435/172 |
| 5,405,765 | A | | 4/1995 | Vasil et al. | 435/172 |
| 5,436,393 | A | * | 7/1995 | Rocha-Sosa et al. | 800/205 |
| 5,451,513 | A | | 9/1995 | Maliga et al. | 438/172.3 |
| 5,464,763 | A | | 11/1995 | Schilperoort et al. | 435/172.3 |
| 5,472,869 | A | | 12/1995 | Krzyzek et al. | 435/240.4 |
| 5,484,956 | A | | 1/1996 | Lundquist et al. | 800/205 |
| 5,489,520 | A | | 2/1996 | Adams et al. | 435/172.3 |
| 5,495,071 | A | | 2/1996 | Fischhoff et al. | 800/205 |
| 5,500,365 | A | | 3/1996 | Fischhoff | 435/240.4 |
| 5,508,468 | A | | 4/1996 | Lundquist et al. | 800/205 |
| 5,538,877 | A | | 7/1996 | Lundquist et al. | 435/172.3 |
| 5,538,880 | A | | 7/1996 | Lundquist et al. | 435/172.3 |
| 5,545,545 | A | | 8/1996 | Gengenbach et al. | 435/172.3 |
| 5,550,318 | A | | 8/1996 | Adams et al. | 800/205 |
| 5,554,798 | A | | 9/1996 | Lundquist et al. | 800/205 |
| 5,561,236 | A | | 10/1996 | Leemans et al. | 800/205 |
| 5,565,347 | A | | 10/1996 | Fillatti et al. | 435/172.3 |
| 5,567,600 | A | | 10/1996 | Adang et al. | 536/23.71 |
| 5,567,862 | A | | 10/1996 | Adang et al. | 530/350 |
| 5,576,203 | A | | 11/1996 | Hoffman | 435/172.3 |
| 5,578,702 | A | | 11/1996 | Adang et al. | 530/350 |
| 5,580,716 | A | | 12/1996 | Johnston et al. | 435/5 |
| 5,589,615 | A | | 12/1996 | De Clercq et al. | 800/205 |
| 5,589,616 | A | | 12/1996 | Hoffman et al. | 800/205 |
| 5,593,963 | A | | 1/1997 | Van Ooijen et al. | 514/12 |
| 5,595,733 | A | | 1/1997 | Carswell et al. | 424/93.21 |
| 5,596,131 | A | | 1/1997 | Horn et al. | 800/205 |
| 5,623,067 | A | | 4/1997 | Vandekerckhove et al. | 536/24.1 |
| 5,641,664 | A | | 6/1997 | D'Halluin et al. | 435/172.3 |
| 5,641,876 | A | | 6/1997 | McElroy et al. | 536/24.1 |
| 5,677,474 | A | | 10/1997 | Rogers | 800/205 |
| 5,693,507 | A | | 12/1997 | Daniell et al. | 435/172.3 |
| 5,743,477 | A | | 4/1998 | Walsh et al. | 424/94.6 |
| 5,780,708 | A | | 7/1998 | Lundquist et al. | 800/205 |
| 5,874,265 | A | | 2/1999 | Adams et al. | 435/172.3 |
| 5,886,244 | A | | 3/1999 | Tomes et al. | 800/293 |
| 5,919,675 | A | | 7/1999 | Adams et al. | 435/172.3 |

FOREIGN PATENT DOCUMENTS

| | | | | |
|---|---|---|---|---|
| EP | 126537 | A2 | 4/1983 | |
| EP | 131623 | B1 | 1/1984 | |
| EP | 141373 | A3 | 5/1985 | |
| EP | 0 142 924 | A2 | 5/1985 | C12N/15/00 |
| EP | 154204 | A2 | 9/1985 | |
| EP | 160390 | A2 | 11/1985 | |
| EP | 0 189 707 | A2 | 8/1986 | C12N/15/00 |
| EP | 193259 | A1 | 9/1986 | |
| EP | 204549 | A2 | 10/1986 | |
| EP | 202668 | A2 | 11/1986 | |
| EP | 242236 | A1 | 10/1987 | |
| EP | 242246 | A1 | 11/1987 | |
| EP | 299552 | A1 | 1/1988 | |
| EP | 257472 | A2 | 3/1988 | |
| EP | 262971 | A2 | 5/1988 | |
| EP | 0 269 601 | A2 | 6/1988 | C12N/15/00 |
| EP | 270356 | A2 | 6/1988 | |
| EP | 271408 | | 6/1988 | |
| EP | 275069 | A2 | 7/1988 | |
| EP | 280400 | A2 | 8/1988 | |
| EP | 282164 | A2 | 9/1988 | |
| EP | 289479 | A2 | 11/1988 | |
| EP | 290395 | A2 | 11/1988 | |
| EP | 292435 | A1 | 11/1988 | C12N/15/00 |
| EP | 301749 | A2 | 2/1989 | |
| EP | 353908 | A2 | 7/1989 | |
| EP | 0 331 083 | A2 | 9/1989 | C12N/15/00 |
| EP | 334539 | A2 | 9/1989 | |
| EP | 338155 | A2 | 9/1989 | |
| EP | 0 335 528 | A2 | 10/1989 | C12N/15/00 |
| EP | 348348 | A2 | 12/1989 | |
| EP | 0 385 962 | A1 | 2/1990 | C12N/15/82 |
| EP | 0 359 472 | A2 | 3/1990 | C12N/15/32 |
| EP | 0 359 617 | A2 | 3/1990 | C12N/15/53 |
| EP | 0 360 750 | A2 | 3/1990 | C12N/15/29 |
| EP | 0 408 403 | A1 | 5/1990 | C12N/15/32 |
| GB | 2159173 | A | 11/1985 | |
| JP | 61-134343 | | 5/1984 | |
| NL | 8801444 | | 1/1990 | |
| WO | 85/01856 | | 5/1985 | |
| WO | 85/02972 | | 7/1985 | |
| WO | 86/01536 | | 3/1986 | C12P/15/00 |
| WO | 86/03776 | | 7/1986 | C12N/15/00 |
| WO | 87/04181 | | 7/1987 | C12N/1/00 |
| WO | 87/05629 | | 9/1987 | |
| WO | 88/08034 | | 10/1988 | C12P/21/00 |
| WO | 89/04371 | | 5/1989 | C12N/21/00 |
| WO | 89/10396 | | 11/1989 | C12N/5/00 |
| WO | 89/11789 | | 12/1989 | A01H/1/00 |

| | | | |
|---|---|---|---|
| WO | 89/12102 | 12/1989 | ..... C12N/15/00 |
| WO | 90/01551 | 2/1990 | ..... C12N/15/82 |
| WO | 90/01869 | 3/1990 | ..... A01H/1/00 |
| WO | 90/02801 | 3/1990 | ..... C12N/15/32 |
| WO | 90/10691 | 8/1990 | ..... C12N/5/00 |

OTHER PUBLICATIONS

Hong, B., et al., "Cloning and Characterization of cDNA Encoding a mRNA Rapidly–Induced by ABA in Barley Aleurone Layers", *Plant Molecular Biology*, 11, 495–506 (1988).

Lemaux, P.G., et al., "Selection of Stable Transformants from Maize Suspension Cultures Using the Herbicide Bialaphos", *J. Cell. Biochem.,* vol. 14e, Abstract R230, 304 (Mar. 31, 1990).

Mundy, J., et al., "Abscisic Acid and Water–Stress Induce the Expression of a Novel Rice Gene", *The EMBO Journal*, 7, 2279–2286 (1988).

Piatkowski, D., et al., "Characterization of Five Abscisic Acid–Responsive cDNA Clones Isolated from the Desiccation–tolerant Plant *Craterostigma plantagineum* the Their Relationship to Other Water–Stress Genes", *Plant Physiology*, 94, 1682–1688 (1990).

Armstrong, C.L., et al., "Genetic and Cytogenetic Variation in Plants Regenerated from Organogenic and Friable, Embryogenic Tissue Cultures of Maize," *Crop Sci., 28,* 363–369 (1988).

Casas, A.M., et al., "Transgenic Sorghum Plants via Microprojectile Bombardment", *Proc. Natl. Acad. Sci. USA*, 90, 11212–11216 (Dec. 1993).

Lemaux, P.G., et al., "Selection of Stable Tranformants from Maize Suspension Cultures Using the Herbicide Bialaphos," *J. Cell. Biochem.*, 14e, Abstract No. R230, p. 304 (Mar. 31, 1990).

Somers, D.A., et al., "Fertile, Transgenic Oat Plants," *Bio/Technology*, 10, 1589–1594 (Dec. 1992).

Wan, Y., et al., "Generation of Large Numbers of Independently Transformed Fertile Barley Plants", *Plant Physiol.*, 104, 37–48 (1994).

Flavell, R., et al., "Prospects for Transforming Monocot Crop Plants", *Nature*, 307, 108–109 (Jan. 12, 1984).

Goodman, R.M., et al., "Gene Transfer in Crop Improvement", *Science*, 236, 48–54 (Apr. 3, 1987).

Paszkowski, J., et al., "Direct Gene Transfer to Plants", *The EMBO Journal*, 3, 2717–2722 (1984).

Poehlman, J.M., "Backcross Breeding", In: *Breeding Field Crops*, 3rd Edition, AVI Publishing Company, Inc., Westport, CT, 203–206 (1988).

Potrykus, I., et al., "Driect Gene Transfer to Cells of a Graminaceous Monocot", *Mol. Gen. Genet.*, 199, 183–188 (1985).

Datta, S.K., et al., "Genetically Engineered Fertile Indica–Rice Recovered from Protoplasts", *Bio/Technology*, 8, 736–740 (Aug. 1990).

McCue, K.F., et al., "Drought and Salt Tolerance: Towards Understanding and Application", *TIBTECH*, 8, 358–362 (Dec. 1990).

Vasil, V., et al., "Regeneration of Plants from Embryogenic Suspension Culture Protoplasts of Wheat (*Triticum aestivum* L.)", *Bio/Technology*, 8, 429–434 (May 1990).

Specification of U.S. patent application Ser. No. 07/205,155, entitled "Stable Transformation of Plant Cells," pp. 1–29 (Filed Jun. 10, 1988).

"BioTechnica Applies for Field Test of Genetically Engineered Corn," *Genetic Technology News,* 10(3), (Mar. 1990).

"Chipping Away at Old Weed Enemies," Farm Science Outlook, *Prairie Farmer* 162, 34 (Feb. 20, 1990).

"Corn Transformers Multiply," *Bio/Technol.,* 8, 490 (Jun. 1990).

"Dekalb Researchers Produce Fertile Corn Plants with Foreign Genes," *ARI Newsletter* (Oct./Nov. 1990).

"Gene Guns Succeed in Altering Corn," *Biotechnology News,* p. 2 (Apr. 1990).

"Genetic Engineering Advance Announced for Corn Plants," *Investor's Daily,* (Apr. 19, 1990).

"Genetically Engineering Corn, Breakthrough Brings Market Closer," *Genetic Technology News,* 8–11 (Oct. 1990).

"Keystone Crops," *Agricultural Genetics Report,* (Mar./Apr. 1990).

"Plant Science Research, Inc. Achieves Successful Transformation of Corn," *Genetic Engineering News,* 10(3), 3 (Mar. 1990).

"Sticky Ends," Genetic Engineering News, 10(5), 1 (May 1990).

"Teams from USDA/Monsanto and DeKalb Genetically Engineer Corn," *Genetic Technology News,* 10(5) (May 1990).

"Two Teams Succeed in Putting Foreign Genes in Corn Plants," *Genetic Engineering Letter,* 10(8), 3 (Apr. 24, 1990).

"USDA Approves Field Test for BioTechnica's Genetically Engineered Corn," *Genetic Technology News,* 10(7), 6 (Jul. 1990).

Bishop, J. E., "Two Teams Plane Genes into Corn," *The Wall Street Journal,* B1 (Apr. 1990).

Clark, B., "Biotech Advance in Corn: Gunslinging Researchers Fire Marker Genes in to Corn," *AG Consultant,* 46(7), 12 (Jul. 1990).

Creissen, G., et al., "Agrobacterium– and Microprojectile–Mediated Viral DNA Delivery into Barley Microspore Derived–Cultures," *Plant Cell Rep.,* 8, 680–683 (Apr. 1990).

DeWald et al., "Plant regeneration from inbred maize suspensions," VIIth International Congress on Plant Tissue and Cell Culture, p. 12, Abstract No. A1–36 (Jun. 24–29, 1990).

Donn, G., et al., "Stable Transformation of Maize with a Chimaeric, Modified Phosphinothricin–Acetyltransferase Gene from *Streptomyces viridochromogenes,"* Abstracts, VIIth International Congress Plant Tissue Cell Culture, p. 53, Abstract No. A2–38 (Jun. 24–29, 1990).

Gordon–kamm, W.J., et al., "Stable Transformation of Embryonic Maize Cultures by Microprojectile Bombardment", *J. Cellular Biochem.*, 13D, p. 259, Abstract No. M122 (1989).

Gunset, G., "Genetic Advance May Transform Corn," *Chicago Tribune* (Apr. 19, 1990).

Kreitlow, B., "Genetic Engineering 'Breakthrough' Disputed," Cedar Rapids Gazette (Apr. 20, 1990).

Looker, D., "Dekalb Claims Success in Effort to Alter Genetic Makeup of Corn," *Des Moines Register* (Apr. 19, 1990).

Moffat, A. S., "Corn Transformed," *Science* 249, 630 (Aug. 10, 1990).

Potrykus, I., "Gene Transfer to Cereals: An Assessment," *Bio/Technol.*, 8, 535–542 (Jun. 1990).

Robbins–Roth et al., "They Make it Happen in Biotech," *Bioworld,* pp. 30–36 (Nov./Dec. 1990).
Spencer et al., "Bialaphos Selection of Stable Transformations from Maize Cell Culture," *Theor. Appl. Genet., 79,* 625–631 (May 1990).
Steimel, D., "Corn Breeders Stalk Perfect Hybrid," *Rockford Register Star,* (Aug. 6, 1990).
Steimel, D., "New Gun Will Custom–Design Corn: Breeding Technique Expected by End of '90's Will Let Crop Grow Without Pesticides or Much Water," (Apr. 1990).
Tomes, D. "Status of Corn Transformation," 26th Annual Corn Breeders School, Meeting Proceedings, U. Illinois, p. 7–8 (Feb. 26–27 1990).
Tomes, D. T., et al., "Transgenic Tobacco Plants and their Progeny Derived by Microprojectile Bombardment of Tobacco Leaves," *Plant Mol. Biol.*, 14, 261–268 (Feb. 1990).
Vasil, I. K., "Transgenic Cereals Becoming a Reality," *Bio/Technol.*, 8, 797 (Sep. 1990).
Botterman, J., et al. "Engineering Herbicide Resistance in Plants", *Trends in Genetics*, vol. 4, No. 8, 221–222, (Aug. 1988).
Ranch, J.P., et al., "Expression of 5–methyltryptophan resistance in plants regnerated from resistant cell lines of Datura innoxia", *Plant Physoil.,* vol. 71, pp. 136–140, (1983).
Van–Slogteren, G.M., et al., "Expression of Ti plasmid genes in monocotyledonous plants infected with Agrobacterium tumefaciens", *Nature* vol. 311, Letter to Nature, pp. 763–764, (Oct. 25, 1984).
"Bullets Transform Plant Cells", *Agricell Report*, 9, 5, (Jul. 1987).
"Catalog, Handbook of Fine Chemicals", Aldrich Chem. Co., p. 508 (1988).
"Cornell U. Gene Gun Hits Biotech Bullseye", *Agriculture Technology,* p. 13.
"Dalapon", *Merck Index,* 11th edition, S. Budavae, (ed.), Merck and Co., pp. 405–406 (1989).
"Dialog Search of Japanese Patent No. 61–13443 (1986)".
"Herbicide–Resistant Corn", *CT Academy of Science and Engineering*, Case Reports, 5(4), 6 (1990).
"Patent Family Record for Australia Patent 87 80 893", Patent Family Record for Australia Patent 87 80 893.
"Shotgunning DNA into Cells", *Genetic Engineering News* (Jul./Aug. 1987).
M. J. Adang, et al., "Characterized Full Length and Truncated Plasmid Clones of the Crystal Protein of *Bacillus thuringiensis* subsp. *kurstadki* HD–73 and Their Toxicity to Maduca sexta", *Gene*, 36, 289–300, (1985).
H. Ahokas, "Transfection of Germinating Barley Seed Electrophorecetically with Exogenus DNA", *Theor. Appl. Genet.* 77, 469–472 (1989).
H. Ahokes, "Electrophorectic transfection of cereal grain with exogenous nucleic acid", *Soc., biochem Biophys. Microbio. Fen., Biotieteen Paivat* (*Bioscience Days*), Abstracts, Technical University of Helsinki, Espoo, p. 2 (1989).
S. B. Altenbach, et al., "Cloning and Sequence Analysis of a cDNA Encoding a Brazil Nut Protein Exceptionally Rich in Methionine", *Plant Mol. Biol.*, 8, 239–250 (1987).
S. B. Altenbach, et al., "Enhancement of the Methionine Content of Seed Proteins by the Expression of a Chimeric Gene Encoding a Methionine–Rich Protein in Transgenic Plants", *Plant. Mol. Biol.*, 13, 513–522 (1989).
C. Ampe, et al., "The Amino–Acid Sequence of the 2S Sulphur–Rich Storage Protein Accumulation in Maize", *Theor. Appl. Genet.*, 78, 761–767 (1989).
C. L. Armstrong, et al., "Establishment and Maintenance of Friable, Embryogenic Maize Callus and the Involvement of L–Proline", *Planta*, 164, 207–214 (1985).
C. L. Armstrong, et al., "Genetic and cytogenetic variation in plants regnerated from organogenic and friable, embryonic tissues cultures of maize", *Biological Abstracts*, 85, Abstract No. 117662 (1988).
R. F. Barker, et al., "Nucelotide Sequence of the T–DNA Region from the Agrobacterium tumefaciens Octopone Ti Plasmid pTi5955", *Plant Mol. Biol.*, 2, 335–350 (1983).
M. S. Benner, et al., "Genetic Analysis of Methionine–Rich Storage Protein Accumulation in Maize", *Theor. Appl. Genet.* 78, 761–767 (1989).
M. Bevan, et al., "A Chimaeric Antibiotic Resistance Gene as a Selectable Marker for Plant Cell Transformation", *Nature*, 304, 184–187 (1983).
M. Bevan, et al., "Structure and Transcription of the Nopaline Synthase Gene Region of T–DNA", *Nuc. Acids Res.* 11, 369–385 (1983).
A. N. Binns, "Agrobacterium–mediated gene delivery and the biology of host range limitations", *Physiologia Plantarum*, 79, 135–139 (1990).
J. E. Bishop, "Two Teams Plane Genes into Corn", *The Wall Street Journal*, B1 (Apr. 1990).
G. Booy, et al., "Attempted Pollen–Mediated Transformation of Maize", *J. Plant Physiol*, 135, 319–324 (1989).
M. I. Boulton, et al., "Specificity fo Agrobacterium mediated delivery of maize streak virus DNA to members of the Gramineae", *Plant Molecular Biology*, 12, 31–40 (1989).
J. S. Boyer, "Water Deficits and Photosynthesis", In: *Water Deficits and Plant Growth*, vol. V, Kozlowski, T.T., (ed), Academic Press, New York, 153–190, (1976).
W. J. Brill, "Agricultural Microbiology", *Scientific American*, 245 (3), 199–215 (Sep. 1981).
V. Buchanan–wollaston, et al., "Detoxification of the Herbicide Dalapon by Transformed Plants", *J. of Cell, Biochem*, 13D, p. 330, Abstract No. M503 (1989).
J. Callis, et al., "Introns Increase Gene Expression in Cultures Maize Cells", *Genes and Development*, 1, 1183–1200 (1987).
J. Cao, et al., "Transformation of Rice and Maize Using the Biolistic Process", In: *Plant Gene Transfer,* Alan R. Liss, Inc., pp. 21–33 (1990).
N. C. Carpita, "The Biochemistry of Growing Cell Walls", In: *Physiology of Cell Expansion During Plant Growth,* Cosgrove, D. J. et al, (eds) Am. Soc. Plant Physiol, pp. 28–100 (1987).
V. L. Chandler, et al., "Two Regulatory Genes of the Maize Anthocyanin Pathway are Homolgous: Isolation of B Utilizing R Genomic Sequences", *The Plant Cell*, 1, 1175–1183 (1989).
P. S. Chourey, et al., "Callus Formation from Protoplasts of a Maize Cell Culture", *Theor. Appl. Genet*. 59, 341–344 (1981).
P. Christou, et al., "Contransformation Frequencies of Foreign Genes in Soybean Cell Cultures", *Theor. Appl. Genet.*, 79, 337–341 (1990).
P. Christou, et al., "Opine Synthesis in Wild Type Plant Tissue", *Plant Physiol*, 82, 218–221 (1986).

P. Christou, et al., "Soybean Genetic Engineering–Commercial Production of Transgenic Plants", *Trends Biotechnol*, 8, 145–151 (1990).
P. Christou, et al., "Stable Transformation of Soybean Callus DNA–Coated Gold Particles", *Plant Physiol*, 87, 671–674 (1988).
C. C. Chu, et al., "Establishment of an Efficient Medium for Another Culture of Rice Through Comparative Experiments on the Nitrogen Sources", *Sci. Sein.* (Peking), 13, 659–668 (1975).
F. Cocking, et al., "Gene Transfer in Cereals", *Science*, 236, 1259–1262 (1987).
Coe, et al., "The Genetics of Corn", In: *Corn and Corn Improvement,* 2nd Edition, Sprague, G.F. (ed.), American Soc. Agronomy, Inc., Madison, WI, p. 138 (1977).
L. Comai, et al., "Expression in Plants of a Mutant aroA Gene from *Salmonella typhimurium* Confers Tolerance to Glyphosate", *Nature*, 317, 741–744 (Oct. 1985).
A. Crossway, et al., "Integrated of foreign DNA following microinjection of tobacco mesophyll protoplasts", *Mol. Gen. Genet*, 202, 179–185 (1986).
A. Darvill, et al., "The Primary Cell Walls of Flowering Plants", *In: The Biochemistry of Plants*, vol. 1, pp. 91–162 (1980).
B. Dauce–lereverand, et al., "Improvement of *Escherichia coli* Strains Overproducing Lysine Using Recombinant DNA Techniques", *Eur. J. Appl. Microbiol. Biotechnol.*, 15, 227–231 (1982).
M. De Block, et al., "Engineering herbicide resistance on plants by expression of a detoxifying enzyme", *EMBO J.*, 6, 2513–2518 (1987).
W. De Greef, et al., "Evaluation of herbicide resistance in transgenic crops under field conditions", *Bio/Technol*, 7, 61–64 (1989).
R. A. Dekeyser, et al., "Evaluation of Selectable Markers for Rice Transformation", *Plant Physiol.* 90, 217–23 (1989).
R. A. Dekeyser, et al., "Transient Gene Expression in Intact and Organized Rice Tissues", *The Plant Cell, 2*, 591–602, (1990).
J. R. Dewet, et al., "Cloning of Firefly Luciferase cDNA and the Expression of Active Luicferase in *Escherichia coli", Proc. Nat. Acad. Sci. USA*, 82, 7870–7873 (1985).
J.m. J. Dewet, et al., "Exogenous gene transfer in maize (*Zea mays*) using DNA–treated pollen", In: *The experimental manipulation of ovule tissues.* Chapman, G.P., et al., (eds.), Longman, New York, pp. 197–209 (1985).
J. G. Ellis, et al., "Does the OCS–Element Occur as a Functional Component of the Promoters of Plant Genes", *EMBO J.*, 6, 3203–3208 (1987).
D. A. Evans, et al., "Somaclonal Variation–Genetic Basis and Breeding Applications", *Trends Genet.*, 5, 46–50 (1989).
J. Finnegan, et al., "Transgene Inactivation: Plants Fight Back?", *Bio/Technol.*, 12, 883–888, (Sep. 1994).
P. Fransz, et al., "Cytodifferentiation during callus initation and somatic embryogenesis in *Zea mays* L", *Ph. D. thesis, U of Wageningen Press, The Netherlands,* (1988).
J. C. Freeling, et al., "Development Potentials of Maize Tissue Cultures", *Maydica, XXI,* 97–112 (Jul. 1977).
Freiberg, "More Researchers Discover Corn Transformation Technology", *AG Biotechnology News,* p. 26 (1990).
M. Fromm, et al., "Expression of Genes Transfected into Monocot and Dicot Plant Cells by Electroportion", *Proc. Nat. Acad. Sci. USA, 82,* 6824–5828, (1985).
M. E. Fromm, et al., "Inheritance and Expression of Chimeric Genes in the Progeny of Transgenic Maize Plants", *Bio/Technol.*, 8, 833–839 (1990).
M. E. Fromm, et al., "Stable Transformation of Maize after Gene Transfer by Electroporation", *Nature*, 319, 791–793, (1986).
S. C. Fry, "Introduction to the Growing Cell Wall", In: *The Growing Plant Cell Wall: Chemical and Metabolic Analysis,* Longman Scientific and Technical, New York, pp. 1–5, 102–109 (1988).
M. Geiser, et al., "The Hypervariable Region on the Genes Coding for Entomopahtogenic Crystal Proteins of *Bacillus thuringiensis*: Nucleotide Sequence of the kurhdl gene fo subsp. kurstaki HD1", *Gene*, 48, 109–108 (1986).
S. A. Goff, et al., "Plant Regeneration of Anthocyanin Biosynethic Genes Following Transfer of B Regulatory Genes into Maize Tissues", *EMBO J.*, 9, 2517–2522 (1990).
W. J. Gordon–Kamm, et al., "Transformation of Maize Cells and Regeneration of Fertile Transgenic Plants," *The Plant Cell,* 2, 603–618 (1990).
W. J. Gordon–kamm, et al., "Stable Transformation of Maize Cells and Regeneration of Fertile Transgenic Plants", *The Plant Cell*, 2, 603–618 (1990).
O. Gould, et al., "Shoot Tip Culture as a Potential Transformation System", Abstracts, *Beltwide Cotton production research conferences,* New Orleans, LA, p. 91 (1988).
A. Graves, et al.,"The transformation of *Zea mays* seedlings with *Agrobacterium tumefacians", Plant Mol. Biol.*, 7, 43–50 (1986).
C. Green, et al., "Plant Regeneration in Tissue Cultures of Maize", *Crop. Sci.*, 15, 417–421 (1975).
C. Green, et al., "Plant Regeneration in Tissue Cultures in Maize", In: *Maize for Biological Research,* Sheridan, W., F., (ed) Plant Mol. Biol. Assoc., pp. 367–372 (1983).
C. Green, et al., "Somatic Cell Genetic System in Corn", *Advances in Gene Technology: Molecular Genetics of Plant and Animals,* Academic Press, Inc., pp. 147–157 (1983).
N. Grimsley, et al., "DNA Transfer from Agrobacterium to *Zea mays* or Brassica by Agroinfection is Dependent on Bacterial Virulence Functions", *Mol. Gen. Genet.*, 217, 309–316 (1989).
L. Gritz, et al., "Plasmid–Encoded Hygromycin B Resistance: The Sequence of Hygromycin B Phosphotransferase Gene and Its Expression in *Escherichia coli* and *Saccharomyces cerevisiae", Gene*, 25, 179–188 (1983).
F. Guerineau, et al., "Sulfonamide Resistance Gene for Plant Transformation", *Plant Molecular Biology*, 15, 127–136 (1990).
H. Guilley, et al., "Transcription of Cauliflower Mosaic Virus DNA: Detection of Promoter Sequences, and Characterization of Transcripts", *Cell*, 30, 763–773 (Oct. 1982).
A. R. Hallauer, et al., "Corn Breeding", *In Corn and Corn Improvement,* 3rd Edition, Sprague, G.F., et al (eds), Agronomy Soc. Amer. pp. 463–564 (1988).
G. W. Haughn, "Transformation with a Mutant Arabidopsis Acetolactate Synthase Gene Renders Tobacco Resistant to Sulfonylurea Herbicides", *Mol. Gen. Genet.*, 211, 266–271 (1988).
R. M. Hauptman, et al., "Evaluation of Selectable Markers for Obtaining Stable Transformants on the Gramineae", *Plant Physil*, 86, 602–606 (1988).
L. M. Hoffman, et al., "A Modified Storage Protein is Synthesized, Processed, and Degraded in the Seeds of Transgenic Plants", *Plant. Mol. Biol.*, 11, 717–729 (1988).

L. M. Hoffman, et al., "Synthesis and Protein Body Deposition of Maize 15kD Zein in Transgenic Tobacco Seeds", *EMBO J.*, 6, 3213–3221 (1987).

H. Hofte, et al., "Insecticidal Crystal Proteins of *Bacillus thruingiensis", Microbiol. Rev.*, 53, 242–255 (1989).

P. J. J. Hooykaas, "Transformation of plant cell via Agrobacterium", *Plant Mol. Biol.* 13, 327–336, (1989).

M. Horn, et al., "Transgenic Plants of Orchard Grass (*Dactylis glomerata* L) from Protoplasts", *Chem. Abstracts*, 110, p. 208, Abstract No. 89869a (1989).

M. Horn, et al., "Transgenic Plants of Orchardgras (*Dactylis glomerata* L.) from Protoplasts", *Plant Cell Reports*, 7, 469, (1988).

Y. Huang, et al., "Factors Influencing Stable Transformation of Maize Protoplasts by Electroporation", *Plant Cell, Tissue and Organ Culture*, 18, 281 (1989).

C. Imbrie–milligan, et al., "Microcallus Growth from Maize Protoplasts", *Planta*, 171, 58–64 (1987).

R. Jefferson, "Assaying chimeric genes in plants: the GUS gene fusion system", *Plant Mol. Biol. Rep.*, 5, 387–405 (1987).

R. Jefferson, et al., "B–Glucuronidase from *Escherichia coli* as a Gene–Fusion Marker", *Proc. Natl. Acad. Sci. USA*, 83, 8447–8451 (1986).

R. Jefferson, et al., "GUS Fusions: B–Glucuronidase as a Sensative and Versatile Gene Fusion Marker in Higher Plants", *EMBO J.*, 6, 3901–3907, (1987).

H. Jones, et al., "Recent Advances in Plant Electroporation", *Oxford Surveys of Plant Molecular and Cell Biol.*, 4, 347–357 (1987).

H. Jones, et al., "Transcient Gene Expression in Electroporated Solanum Protoplasts", *Plant Mol. Biol.*, 13, 503–511 (1989).

H. F. Kaeppler, et al., "Silicon Carbide Fiber–Mediated DNA Delivery into Plant Cells", *Plant Cell Rep.*, 9, 415–418 (1990).

K. Kamo, et al., "Establishment and Characterization of Long–Term Embryonic Maize Callus and Cell Suspension Cultures", *Plant Sci.*, 45, 111–117 (1986).

K. Kamo, et al., "Regeneration of *Zea mays* L. from Embryogenic Callus", *Bot. Gaz.* 146, 327–334 (1985).

K. N. Kao, et al., "Nutritional Requirement for Growth of *Vicia hajastana* Cells and Protoplasts at a Very Low Population Densith in Liquid Media", *Planta*, 126, 105–110 (1978).

K. Kartha, et al., "Transient Expression of Chloramphenicol Acetyl Transferase (CAT) Gene in Barley Cell Cultures and Immature Embryos Through Microprojectile Bombardment", *Plant, Cell, Rep.*, 8, 429–432 (1989).

R. Kay, et al., "Duplication of CaMV 35S Promoter Sequences Creates a Strong Enhancer for Plant Genes", *Science, 236*, 1299–1302 (Jun. 5, 1987).

J. Kirihara, et al., "Differential Expressioni of a Gene for a Methionine–Rich Storage Protein in Maize", *Mol. Gen. Genet.*, 211, 477–484 (1988).

J. Kirihara, et al., "Isolation and Sequence of a Gene Encoding a Methionine–Rich 10–kD Zein Protein from Maize", *Gene*, 71, 359–370 (1988).

T. M. Klein, et al., "Factors Influencing Gene Delivery into *Zea mays* Cells by High Velocity Microprojectiles", *Bio/Technol*, 6, 559–563 (1988).

T. Klein, et al., "Genetic Transformatio of Maize Cell by Particle Bombardment and the Influence of Mehtylation on Foreign Gene Expression", In: *Gene Manipulation In Plant Improvement II,* Gustafson, J.P., (ed.), Plenum Press, NY, pp. 265–266 (1990).

T. M. Klein, et al., "High–Velocity Microprojectiles for Delivering Nucleic Acids to Living Cells", *Nature*, 327, 70–73 (1987).

T. M. Klein, et al., "Genetic Transformation of Maize Cells by Particle Bombardment," *Plant Physiol.*, 91, 440–444 (1989).

T. Klein, et al., "Regulation of Anthocyanin Biosynthtic Genes Introduced into Intact Maize Tissue by Microprojectiles", *Pro. Nat. Acad. Sci., USA*, 86, 6682–6685 (1989).

T. Klein, et al., "Transfer of Foreign Genes into Intact Maize Cells with High–Velocity Microprojectiles", *Pro. Nat. Acad. Sci. USA, 85*, 4305–4309 (1988).

M. Kozak, "Compilation and Analysis of Sequence from the Translational Start Site in Eukaryotic mRNAs", *Nuc. Acids. Res.*, 12, 857–871 (1984).

M. Kozak, "Point Mutations Define a Sequence Flanking the AUG Inhitiator Codon that Modulates Translation by Eukaryotic Ribosomes", *Cell*, 44, 283–292 (1986).

C. Kuhlemeier, et al., "Regulation of Gene Expression in Higher Plants", *Ann. Rev. Plant Physiol*, 38, 234–239 (1987).

P. Lazzeri, et al., "In Vitro Genetic Manipulation of Cereals and Grasses", *Ad. Cell Culture*, 6, 291–293 (1988).

J. S. Lee, et al., "Gene Transfer into Inact Cells of Tobacco by Electroporation", *Korean J. Gent.*, 11, 65–72 (1989).

J. Levitt, "Growth Regulators", In: *Introduction to Plant Physiology,* The C.V. Mosby Company, St. Louis, p. 241 (1969).

K. Lindsey, et al., "Electroporation of Cells", *Physiologia Plantarum*, 79, 168–172 (1990).

K. Lindsey, et al., "Stable Transformation of Sugarbeet Protoplasts by Electroporation", *Plant Cell. Rep.*, 8, 71–74 (1989).

K. Lindsey, et al., "The Permeability of Electroporated Cells and Protoplasts of Sugar Beet", *Planta*, 172, 346–355 (1987).

K. Lindsey, et al., "Transient Gene Expression in Electroporated Protoplasts and Inact Cells of Sugar Beet", *Plant Mol. Biol.*, 10, 43–52 (1987).

H. Lorz, et al., "Advances in Tissue Cultures and Progress Towards Genetic Transformation of Cereals", *Plant Breeding*, 100, 1–25 (1988).

C. Lu, et al., "Improved Efficiency of Somatic Embryogenesis and Plant Regeneration on Tissue Cultures of Maize (*Zea mays* L.", *Theor. Appl. Genet.* 66, 285–289 (1983).

C. Lu, et al., "Somatic Embryogenesis in *Zea mays* L", *Theor. Appl. Genet,* 62, 109–112 (1982).

S. Ludwig, et al., "A Regulatory Gene as a Novel Visible Marker for Maize Transformation", *Science*, 247, 449–450 (1990).

S. Ludwig, et al., "High Frequency Callus Formation from Maize Protoplasts", *Theor. Appl. Genet.*, 71, 344–350 (1985).

S. Ludwig, et al., "Lc, a Member of the Maize R Gene Family Responsible for Tissue–Specific Anthocyanin Production, Encodes a Protein Similar to Transcriptional Activators and Contains the myc–Homology Region", *Proc., Nat. Acad. Sci. USA*, 86, 7092–7096 (1989).

S. Ludwig, et al., "Maize R Gene Family: Tissue Specific Helix Loop Helix Proteins", *Cell*, 62, 849–851 (1990).
H. Lutcke, et al., "Selection of AUG Initation Codons Differs in Plants and Animals", *EMBO J.*, 6, 43–48 (1987).
T. Masumura, et al., "cDNA Cloning of an mRNA Encoding a Sulfur–Rich 10 kDa Prolamin Polyeptide in Rice Seeds", *Plant Mol.*, 12, 123–130 (1989).
Mccabe, et al., "Stable Transformation of Soybean (Glycine max) by Particle Acceration", *Bio/Technol,* 6, 923–926 (1988).
C. Mcdaniel, et al., "Cell–Lineage Pattens in the Shoot Apical Meristem of the Germinating Maize Embryo", *Planta*, 175, 13–22 (1988).
M. Meadows, "Characterization of Cells and Protoplasts of the B73 Maize Cell Line", *Plant Sci. Lett.*, 28, 337–348 (1982/83).
R. Mendel, et al., "Delivery of Foreign Genes to Intact Barley Cell by High–Velocity Microprojectiles", *Theor. Appl. Genet.*, 78, 31–34 (1989).
J. Messing, "Corn Storage Protein: A Molecular Genetic Model", *Division of Energy BioSciences–Summeries of FY 1990 Activities,* p. 70, Abstract No. 135 (1990).
B. V. Milborrow, "Abscisic Acid and Other Hormones", In: *The Physiology and Biochemistry of Drought Resistance in Plants,* Paleg, L.G. et al. (eds), Academic Press, New York, 347–388, (1981).
Morikawa, et al., "Gene Transfer into Intact Plant Cells by Electroporation Through Cell Walls and Membranes", *Gene*, 41, 121 (1986).
S. Morocz, et al., "An Improved System to Obtain Fertile Regenerants via Maize Protoplasts Isolated From a Highly Embryonic Suspension Culture", *Theor. Appl. Genet.*, 80, 721–726 (1990).
S. Morocz, et al., "Two Approaches to Rendering *Zea mays* L. Applicable to Tissue Culture Manipulations", *Abstracts, VIIth Int. Cong. on Plant Tissue and Cell Culture, Amsterdam A1–102,* Abstract No. 209, p. 190 (1990).
T. Murakami, et al., "The Bialaphos Biosynthetic Genes of *Streptomyces hygroscopicus*: Molecular Cloning and Characterization of the Gene Cluster", *Mol. Gen. Genet.* 205, 42–50 (1986).
T. Murashige, et al., "A Revised Medium for Rapid Growth and Bio Assays with Tobacco Tissue Cultures", *Physiol Plant*, 15, 473–497 (1962).
H. L. Murphy, "New Dekalb–Pfizer Seed Chief to Harvest R & D Breakthroughs", *Crain's Business Weekly,* pp. 38–39 (1990).
E. E. Murray, et al., "Codon usage in plant genes", *Nuc. Acids Res.*, 17, 477–498 (1989).
T. Nelson, "New Horses for Monocot Gene Jockeys", *The Plant Cell*, 2, 589 (1990).
R. S. Nelson, "Virus Tolerance, Plant Growth and Field Performance of Transgenic Tomato Plants Expressing Coat Protein from Tobacco Mosaic Virus", *Bio/Technol*, 6, 403–409 (1990).
Neuffer, "Growing Maize for Genetic Purposes", *Maize for Biological Research, Plant Mol. Biol. Assoc.,* (1988).
J. Odell, et al., "Identification of DNA Sequences Required for Activity of the Caulliflower Mosaic Virus 35S Promoter", *Nature*, 313, 810–811 (1985).
Y. Ohta, et al., "High–Efficiency Genetic Transformation of Maize by a Mixture of Pollen and Exogenous DNA", *Pro. Nat. Acad. Sci. USA*, 83, 715–719 (1986).
Y. Okta, et al., "Gene Manfestation of Exogenous DNA Applied to Self–Propagating Stigma (Gene Action Revealed in the M1 and M2 Generations from Self–Pollination Applying Exogenous DNA", *Jap. J. Breed.*, 30, 184–185 (1980).
P. Ozias–akins, et al., "In vitro regeneration and genetic manipulation of grasses", *Physiol. Plant.*, 73, 565–569 (1988).
P. Ozias–akins, et al., "Progress and Limitations in the Culture of Cereal Protoplasts", *Trends in Biotechnol*, 2, 119–123 (1984).
W. B. Parker, et al., "Selection and Characterization of Sethoxydim–Tolerant Maize Tissue Cultures", *Plant Physiol.*, 92, 1220–1225 (1990).
K. Pederson, et al., "Sequence Analysis and Characterization of a Maize Gene Encoding a High Sulfure Zein Protein of M1 15,000", *J. Biol. Chem*, 261, 6279–6284 (1986).
R. L. Phillips, et al., "Cell/Tissue Culture and In Vitro Manipulation", In: *Corn and Corn Improvement*, 3rd edition, Sprague, G.F., et al, (eds.), Agronomy Soc. Amer., pp. 345–387 (1988).
R. L. Phillips, et al., "Elevated Protein–Bound Methionine in Seeds of a Maize Line Resistant to Lysine Plus Threonine", *Cereal Chem*, 62, 213–218 (1985).
J. Poehlman, "Breeding Corn (Maize)", In: *Breeding Field Crops,* 3rd edition, AVI Publishing Co., Westport CN, pp. 469–471, 477–481 (1986).
J. Poehlman, "Breeding Corn (Maize)," In: *Breeding Field Crops,* 3rd edition, AVI Publishing Co., Westport CN, pp. 452 (1986).
I. Potrykus, et al., "Callus Formation from Cell Culture Protoplasts of Corn (*Zea mays* L.)," *Theor. Appl. Genet.*, 54, 209–214 (1979).
I. Potrykus, "Gene Transfer to Cereals: An Assessment," *Trends Biotechnol.*, 7, 269–273 (Oct., 1989).
I. Potrykus, et al., "Callus formation from stem protoplasts of corn (*Zea mays* L.)", *Mol. Gen. Genet.* 156, 347–350 (1977).
I. Potrykus, "Gene Transfer to Plants: Assessment and Perspectives", *Physiol. Plant*, 79, 125–134 (1990).
Potter, et al., "Enchancer–Dependent Expression of Human k Immunoglobulin Genes Introduced into Mouse Pre–B Lymphocytes by Electroporation", *Pro. Nat. Acad. Sci. USA*, 81, 7161 (1984).
L. M. Prioli, et al., "Plant Regeneration and Recovery of Fertile Plants from Protoplasts of Maize (*Zea mays* L)", *Bio/Technol*, 7, 589–594 (Jun. 1989).
K. J. Puite, et al., "Electrofusion a Simple and Reproducible Technique in Somatic Hybridization of *Nicotiana plumbaginifolia* mutants", *Plant Cell Rep.*, 4, 274–276 (1985).
C. A. Rhodes, "Corn: From Protoplasts to Fertile Plants", *Bio/Technol*, 7, 548 (Jun. 1989).
C. A. Rhodes, et al., "Genectically Transformed Maize Plants from protoplasts", *Science*, 240, 204–207 (Apr. 8, 1988).
C. A. Rhodes, et al., "Plant Regeneration from Protoplasts Isolated from Embryogenic Maize Cell Cultures", *Bio/Technol.*, 6, 56–60 (Jan. 1988).
F. Richaud, et al., "Chromosomal Location and Nucleotide Sequence of the *Escherichia coli* dapA Gene", *Biol. Abstracts*, 82, p. AB–391, Abstract No. 3396 (1986).
F. Richaud, et al., "Chromosomal Location and Nucleotide Sequence of the *Escherichia coli* dapA Gene", *J. Bacteriol*, 166, 297–300 (1986).

D. S. Robertson, "Loss of Mu Mutator Activity when Active Mu Systems are Transferred to Inbred Lines", *Maize Genetics Coop. Newsletter*, 60, 10 (1986).

M. C. Ross, et al., "Transient and Stable Transgenic Cells and Calli of Tobacco and Maize Following Microprojectile Bombardment", *J. Cell. Biochem.*, 13D, p. 268, Abstract No. M149 (1989).

S. V. Sahi, et al., "Metabolites in Maize Which Affect Virulence Induction in *Agrobacterium tumefaciens", Plant Physiol., Supplement,* p. 86, Abstract No. 514 (1989).

J. C. Sanford, et al., "Attempted Pollen–Mediated Plant Transformation Employing Genomic Donor DNA", *Theor. Appl. Genet.*, 69, 571–574 (1985).

J. C. Sanford, et al., "Biolistic Plant Transformation", *Physiol Plant*, 79, 206–209, (1990).

J. C. Sanford, et al., "Delivery of Substances into Cells and Tissues Using a Particle Bombardment Process", *Particulate Sci. Technol.*, 5, 27–37 (1987).

J. C. Sanford, "The Biolistic Process", *Trends Biotechnol, 6,* 299–302 (1988).

Sass, "Morphology: Development of the Caryopsis", In: *Corn and Corn Improvement*, 2nd edition, Sprauge, G.F., (ed), American Soc. Agronomy, p. 89, 98 (1977).

A. Schmidt, et al., "Media and environmental effects of phenolics production from tobacco cell cultures", *Chem. Abstracts.*, 100, p. 514, Abstract No. 230156z(1989).

K. Shigekawa, et al., "Electroporation of Eukaryotes and Prokaryotes: A General Approach to the Intoduction of Macromoleucles into Cells", *BioTechniques*, 6, 742–751 (1988).

R. D. Shillito, et al., "High Efficiency Direct Gene Transfer to Plants", *Bio/Technol*, 3, 1099 (1985).

R. D. Shillito, et al., "Regeneration of Fertile Plants From Protoplasts of Elite Inbred Maize", *Bio/Technol*, 7, 581–587 (Jun. 1989).

K. Shimamoto, et al., "Fertile Transgenic Rice Plants Regenerated from Transformed Protoplasts", *Nature*, 338, 274–278 (1989).

M. A. Shotwell, et al., "The Biochemistry of Plants—A Comprehensive Treatise", *The Biochemistry of Plants*, vol. 15, Marcus, A., (ed), Academic Press, Inc, San Diego, pp. 297–345 (1989).

R. Smith, et al., "Shoot apex explant for transformation", *Plant Physiology* (*Suppl*), 86, p. 108, Abstract 646, (1988).

X. Soberon, et al., "Construction and Characterization of New Cloning Vehicles, IV. Deletion Drivatives of pBR322 and pBR325", *Gene* 9, 287–305 (1980).

T. M. Spencer, et al., "Fertile Transgenic Maize", *Abstracts, 7th Annual Meeting, Mid Atlantic Plant Mol. Biol. Soc.,* p. 30 (1990).

T. M. Spencer, et al., "Selection of Stable Transformants from Maize Suspension Cultures using the Herbicide Bialaphos", *Poster presentation, FASEB Plant Gene Expression Conference,* Copper Mountain, Colorado (Aug. 8, 1989).

Sprauge, et al., "Corn Breeding", In: *Corn and Corn Improvement,* Sprague, G.F. (ed), American Society of Agronomy, Inc., Madison, Wi. pp. 305, 320–323 (1977).

M. Sugiyama, et al., "Use of Tyrosinase Gene from Streptomyces to Probe promoter Sequences for *Escherichia coli", Plasmid*, 23, 237–241 (1990).

C. Thompson, et al., "Characterization of the Herbicide–Resistance Gene bar from *Streptomyces hygroscopicus", EMBO J.*, 6, 2519–2523 (1987).

D. Twell, et al., "Transient Expression of chimeric genes delivered into Pollen by Microprojectile Bombardment", *Plant Physiol*, 91, 1271–1274 (1989).

E. Ulian, et al., "Transformation of Plants via the Shoot Apex", *In Vitro Cell Dev. Biol.*, 9, 951–954, (1988).

S. Usami, et al., "Absence in Monocotyledonous Plants of the Diffusable Plant Factors including T–DNA Circulazation and vir Gene Expression in Agrobacterium", *Mol. Gen. Genet.*, 209, 221–226 (1987).

I. K. Vasil, et al., "Culture of Protoplasts Isolated from Embryogenic Cell Suspension Cultures of Sugarcane and Maize", *IAPTC Abstracts,* 443, (1986).

V. Vasil, et al., "Isolation and Maintenane of Embryogenic Cell Suspension Cultures of Gramineae", In: *Cell Culture and Somatic cell Genetics of Plants*, vol. I, Academic Press, pp. 152–158 (1984).

V. Vasil, et al., "Plant Regeneration from Friable Embryonic Callus and Cell Suspension Cultures of *Zea mays* L", *J. Plant Physiol*, 124, 399–408 (1986).

V. Walbot, et al., "Molecular genetics of corn", *Corn and Corn Improvement*, 3rd edition, Sprague, G.F., et al, (eds), American Soc. Agronomy, Madison, WI, pp. 389–430 (1988).

C. Waldron, et al., "Resistance to Hygromycin B", *Plant Mol. Biol.*, 5, 103–108 (1985).

Y. Wang, et al., "Transient Expression of Foreign Genes in Rice, Wheat, and Soybean Cells following particle bombardment", *Plant Mol. Biol.* 11, 433–439 (1988).

K. Weising, et al., "Foreign Genes in Plants: Transfer, Structure, Expression and Applicatioins", *Ann. Rev. Genet.* 22, 421–478 (1988).

J. White, et al., "A Cassette Containing the bar Gene of *Streptomyces hygroscopicus*: a Selectable Marker for Plant Transformation", *Nuc. Acid. Res.*, 18, 1062 (1989).

H. R. Whiteley, et al., "The Molecular Biology of Parasporal Crystal Body Formation in *Bacillus thuringiensis", Ann. Rev. Microbiol.*, 40, 549–576 (1986).

H., Yang, et al., "Production of Kanamycin Resistant Rice Tissues Following DNA Uptake into Protoplasts", *Plant Cell Rep.*, 7, 421 (1988).

C. Yanisch–perron, et al., "Improved M13 Phage Vectors and Host Strains: Nucleotide Sequences of the M13mp18 and pUC19 Vectors", *Gene*, 33, 103–119 (1985).

Y. Yugari, et al., "Coordinated End–Product Inhibition in Lysine Synthesis in *Escherichia coli.", Biochem, Biophys. Acta.* 62, 612–614 (1962).

P. J. Charest, et al., "Factors Affecting the Use of Chloramphenicol Acetyltransferase as a Marker for Brassica Genetic Transformation", *Plant Cell Reports*, 7, 628–631 (1989).

L. Herrera–Estrella, et al., "Use of Reporter Genes to Study Gene Expression in Plant Cells", In: *Plant Molecular Biology Manual B1,* Kluwer Academic Publishers, Dordrecht, pp. 1–22 (1988).

M. M. Johri, et al., "Genetic Approaches to Meristem Organization", In: *Maize for Biological Research,* W. F. Sheridan, (ed.), Plant Molecular Biology Association, pp. 301–310 (1982).

U.S. patent application Ser. No. 07/392,176, Adams et al. filed Aug. 9, 1989.

U.S. patent application Ser. No. 07/513,298, Adams et al., filed Apr. 17, 1990.

*In Vitro Cellular & Developmental Biology*, 21, Program Issue: Thirty–Sixth Annual Meeting of the Tissue Culture Association, New Orleans, LA, 88 p. (Mar. 1985).

*In Vitro Cellular & Developmental Biology*, 23, Program Issue: Thirty–Eighth Annual Meeting of the Tissue Culture Association, Washington, D.C., 93 p. (Mar. 1987).

*In Vitro Cellular & Developmental Biology*, 24, Program Issue: Thirty–Ninth Annual Meeting of the Tissue Culture Association, Las Vegas, NV, 92 p. (Mar. 1988).

*In Vitro Cellular & Developmental Biology*, 25, Program Issue: Fortieth Annual Meeting of the Tissue Culture Association, Orlando, Fl, 73 p. (Mar. 1989).

*In Vitro Cellular & Developmental Biology*, 26, Program Issue: Forty–First Annual Meeting of the Tissue Culture Association, Houston, TX 88 p. (Mar. 1990).

"Ciba–Geigy Joins Maize Transformers", *AGROW*, No. 118, 20 (Aug. 31, 1990).

"European Firm Devises Insect–Resistant Plants", *Agricultural Biotechnology News*, 1, 6 (Mar.–Apr. 1986).

"Molecular Strategies for Crop Improvement", *Journal of Cellular Biochemistry*, Supplement 14e, List of Plenary and Poster Sessions, organized by Arntzen, C., et al., for The Keystone Conference on Molecular Strategies for Crop Plant Improvement, held at the 19th UCLA Symposia, 257 (1990).

"Monsanto, DeKalb Gunning for Insect–, Disease–Resistant Corn", *Biotechnology Newswatch*, 4–5 (May 7, 1990).

"Plant Science Produces Transformed Corn", *Chemical and Engineering News*, 7 (Jan. 29, 1990).

Abbe, E.C., et al., "The Growth of the Shoot Apex in Maize: Embryogeny", *American Journal of Botany*, 41, 285–293 (Apr. 1954).

Abe, K., et al., "Molecular Cloning of a Cysteine Proteinase Inhibitor of Rice (Oryzacystatin)", *The Journal of Biological Chemistry*, 262, 16793–16797 (Dec. 15, 1987).

Adang, M.J., et al., "Expression of a *Bacillus thuringiensis* Insecticidal Crystal Protein Gene in Tobacco Plants", *Molecular Strategies for Crop Protection*, Arntzen, C.J., et al. (eds.), Alan R. Liss, Inc., New York, 345–353 (1987).

Anderson, J.M., et al., "The Encoded Primary Sequence of a Rice Seed ADP–glucose Pyrophosphorylase Subunit and Its Homology to the Bacterial Enzyme", *The Journal of Biological Chemistry*, 264, 12238–12242 (Jul. 25, 1989).

Anderson, P.C., et al., "Herbicide–Tolerant Mutants of Corn", *Genome*, 31, 994–999 (1989).

Angus, T.A., "Implications of Some Recent Studies of *Bacillus thuringiensis*—A Personal Purview", *Proceedings of the 4th International Colloquium on Insect Pathology*, College Park, MD, 183–189 (Aug. 25–28, 1970).

Armaleo, D. et al., "Biolistic Nuclear Transformation of *Saccharomyces cervisiae* and Other Fungi", *Curr. Genet.*, 17, 97–103 (1990).

Aronson, A.I., et al., "*Bacillus thuringiensis* and Related Insect Pathogens", *Microbiological Reviews*, 50, 1–24 (Mar. 1986).

Aronson, J.N., et al., "Toxic Trypsin Digest Fragment from the *Bacillus thuringiensis* Parasporal Protein", *Applied and Environmental Microbiology*, 53, 416–421 (Feb. 1987).

Barton, K.A., et al., "*Bacillus thuringiensis* δ–Endotoxin Expressed in Transgenic *Nicotiana tabacum* Provides Resistance to Lepidopteran Insects", *Plant Physiol.*, 85, 1103–1109 (1987).

Birk, Y., et al., "Separation of a Tribolium–Protease Inhibitor from Soybeans on a Calcium Phosphate Column", *Biochem. Biophys. Acta*, 67, 326–328 (Feb. 12, 1963).

Bishop, D.H., et al., "Genetically Engineered Viral Insecticides—A Progress Report 1986–1989", *Pestic. Sci.*, 27, 173–189 (1989).

Bol., J.F., et al., "Plant Pathogenesis–Related Proteins Induced by Virus Infection", *Annu. Rev. Phytopathol.*, 28, 113–138 (1990).

Boynton, J.E., et al., "Chloroplast Transformation in Chlamydomonas with High Velocity Microprojectiles", *Science*, 240, 1534–1537 (Jun. 10, 1988).

Bryant, J.A., "At Last: Transgenic Cereal Plants from Genetically Engineered Protoplasts", *Trends in Biotechnology*, 6, 291–292 (Dec. 1988).

Burgerjon, A., et al., "Industrial and International Standardization of Microbial Pesticides—I. *Bacillus thuringiensis", Entomophaga*, 22, 121–129 (1977).

Busvine, J.R., *A Critical Review of the Techniques for Testing Insecticides*, Table of Contents, Commonwealth Agricultural Bureaux, Slogh, England, iii–xi (1971).

Bytebier, B., et al., "T–DNA Organization in Tumor Cultures and Transgenic Plants of the Monocotyledon *Asparagus officinalis", Proc. Natl. Acad. Sci. USA*, 84, 5345–5349 (Aug. 1987).

Calabrese, D.M., et al., "A Comparison of Protein Crystal Subunit Sizes in *Bacillus thuringiensis", Canadian Journal of Microbiology*, 26, 1006–1010 (Aug. 1980).

Caplan, A., et al., "Introduction of Genetic Material into Plant Cells", *Science*, 222, 815–821 (Nov. 18, 1983).

Chaleff, R.S., "Induction, Maintanance, and Differentiation of Rice Callus Cultures on Ammonium as Sole Nitrogen Source", *Plant Cell Tissue Organ Culture*, 2, 29–37 (1983).

Christou, P. et al., "Inheritance and Expression of Foreign Genes in Transgenic Soybean Plants", *Proc. Natl. Acad. Sci. USA*, 86, 7500–7504 (Oct. 1989).

Cooksey, K.E., "Purification of a Protein from *Bacillus thuringiensis* Toxic to Larvae of Lepidoptera", *Biochem. J.*, 106, 445–454 (1968).

De Block, M., et al., "Expression of Foreign Genes in Regenerated Plants and Their Progeny", *EMBO J.*, 3, 1681–1689 (1984).

De Block, M., et al., "The Use of Phosphinothricin Resistance as a Selectable Marker in Tobacco Protoplast Transformation", In: *Progress in Plant Protoplast Research*, Puite, K.J., et al., (eds.), Kluwer Academic Publishers, Dordrecht, The Netherlands, p. 389–390 (Dec. 6–11, 1987).

Denecke, J., et al., "Quantification of Transient Expression Levels in Genes Transferred to Plant Protoplasts by Electroporation", *Progress in Plant Protoplast Research*, Puite, K.J., et al., (eds.), Proceedings of the 7th International Protoplast Symposium, Waginingen, The Netherlands, 337–338 (Dec. 6, 11, 1987).

Depicker, A.G., et al., "A Negative Selection Scheme for Tobacco Protoplast–Derived Cells Expressing the T–DNA Gene 2", *Plant Cell Reports*, 7, 63–66 (1988).

Domoney, C., et al., "Cloning and Characterization of Complementary DNA for Convicilin, a Major Seed Storage Protein in *Pisum sativum* L.", *Planta*, 159, 446–453 (1983).

Duncan, D.R., et al., "The Production of Callus Capable of Plant Regeneration for Immature Embryos of Numerous *Zea Mays* Genotypes", *Planta*, 165, 322–332 (1985).

Dunleavy, J.M., "*Curtobacterium plantarum* sp. nov. Is Ubiquitous in Plant Leaves and Is Seed Transmitted in Soybean and Corn", *International Journal of Systematic Bacteriology*, 39, 240–249 (Jul. 1989).

Dunn, G.M., et al., "Inheritance of Cyclic Hydroxamates in *Zea mays* L.", *Can. J. Plant Sci.*, 61, 583–593 (Jul. 1981).
Dybvig, K., et al., "Transposition of Gram–Positive Transposon Tn916 in *Acholeplasma laidlawii* and *Mycoplasma pulmonis", Science*, 235, 1392–1394 (Mar. 13, 1987).
Edallo, S., et al., "Chromosomal Variation and Frequency of Spontaneous Mutation Associated with in vitro Culture and Plant Regeneration in Maize", *Maydica*, 26, 39–56 (1981).
Fast, P.G., et al., "*Bacillus thuringiensis* δ–Endotoxin: Evidence that Toxin Acts at the Surface of Susceptible Cells", *Experientia*, 34, 762–763 (1978).
Faust, R.M, et al., "Bacteria and Their Toxins as Insecticides", In: *Microbial and Viral Pesticides*, Kurstak, E., (ed.), Marcel Dekker, Inc., New York, 75–208 (1982).
Finkle, B.J., et al., "Growth and Regeneration of Alfalta Callus Lines After Freezing in Liquid Nitrogen", *Plant Science*, 42, 133–140 (1985).
Finney, D.J., In: *Probit Analysis: A Statistical Treatment of the Sigmoid Response Curve*, iii–ix (1952).
Fischhoff, D.A., et al., "Insect Tolerant Transgenic Tomato Plants", *Bio/technology*, 5, 807–812 (1987).
Fukuto, T.R., "Physicochemical Aspects of Insecticidal Action", In: *Insecticidal Biochemistry and Physiology*, Wilkinson, C.F., (ed.), Plenum Press, New York, 397–428 (1976).
Gallagher, S., "Progress and Promise of the Particle Gun", *Ag Biotechnology News*, 6, 12–13 (Mar.–Apr. 1989).
Gallie, D.R., et al., "The 5'–leader Sequence of Tobacco Mosaic Virus RNA Enhances the Expression of Foreign Gene Transcripts in Vitro and in Vivo", *Nucleic Acids Research*, 15, 3257–3273 (1987).
Gatehouse, A.M.R., et al., "Assessment of the Antimetabolic Effects of Trypsin Inhibitors from Cowpea (*Vigna unguiculata*) and Other Legumes on Development of the Bruchid Beetle *Cellosobruchus maculatus", J. Sci. Food Agric.*, 34, 345–350 (1983).
Genovesi, A.D., "Embryogenesis in Callus Derived from Rice Microspores", *Plant Cell Reports*, 1, 257–260 (1982).
Georghiou, G.P., et al. "Factors Influenceing the Evolution of Resistance", In: *Pesticide Resistance: Strategies and Tactics for Management*, Committee on Strategies for the Management of Pesticide Resistant Pest Populations, Board on Agriculture, National Research Council, National Academy Press, Washington, D.C., 157–169 (1986).
Gepts, P., et al., "Enhanced Available Methionine Concentration Associated with Higher Phaseolin Levels in Common Bean Seeds", *Theor. Appl. Genet.*, 69, 47–53 (1984).
Gerlach, W.L., "Genetic Engineerng: Its Place in Plant Breeding", In: *Plant Breeding and Genetic Engineering*, Zakri, A.H., (ed.), Society for the Advancement of Breeding Researches in Asia and Oceania, Bangi, Malaysia, 269–277 (1988).
Goff, S.A., et al., "Transactivation of Anthocyanin Biosynthetic Genes Following Transfer of B Regulatory Genes into Maize Tissues", *EMBO Journal*, 9, 2517–2522 (1990).
Goldburg, R.J., et al., "Are B.T.K. Plants Really Safe to Eat?", *Bio/technology*, 8, 1011–1015 (Nov. 1990).
Goldfarb, B., et at., "Transient Expression of Microprojectile–Introduced DNA in Douglas–Fir", *J. Cell. Biochem.*, 13D, Abstract No. M121, p. 259 (1989).
Goldman, S.L., et al., "Transformation of *Zea mays* by *Agrobacterium tumefaciens*: Evidence for Stable Genetic Alternations", *Journal of Cellular Biochemistry*, 11B, Abstract No. F 202, p. 26 (1987).
Gordon, P.N. et al., "Plant Regeneration from Tissue Cultures of Maize", *Maize Genetics Cooperation Newsletter*, 51, 79–80 (Mar. 1, 1977).
Green, C.E., "New Developments in Plant Tissue Culture and Plant Regeneration", In: *Basic Biology of New Developments in Biotechnology*, Hollaender, A., et al., (eds.), Plenum Press, New York, 195–209 (1983).
Green, C.E., "Somatic Embryogenesis and Plant Regeneration from the Friable Callus of *Zea mays", Proceedings of the 5th International Congress on Plant Tissue & Cell Culture*, Tokyo, Japan, 107–108 (1982).
Guerrero, F.D., et al., "Turgor–Responsive Gene Transcription and RNA Levels Increase Rapidly When Pea Shoots are Wilted. Sequence and Expression of Three Inducible Genes", *Plant. Mol. Biol.*, 15, 11–26 (1990).
Haccius, B., "Question of Unicellular Origin of Non–Zygotic Embryos in Callus Cultures", *Phytomorphology*, 28, 74–81 (1978).
Harms, C.T., et al., "Regeneration of Plantlets from Callus Cultures of *Zea mays* L.", *Z. Ptlanzenzuchtg.* 77, 347–351 (1976).
Hartree, E.F., "Determination of Protein: A Modification of the Lowry Method that Gives a Linear Photometric Response", *Analytical Biochemistry*, 48, 422–427 (1972).
Harvey, W.R., et al., "Potassium Ion Transport ATPase in Insect Ephthelia", *J. Exp. Biol*, 106, 91–117 (1983).
Heimpel, A.M., et al., "Recent Advances in the Knowledge of Some Bacterial Pathogens of Insects", *Proceedings of the Tenth International Congress of Entomology*, vol. 4, 711–722 (1956).
Heimpel, A.M., et al., "The Site of Action of Crystalliferous Bacteria in Lepidoptera Larvae", *Journal of Insect Pathology*, 1, 152–170 (1959).
Hernalsteens, J.–P., et al., "An Agrobacterium–Transformed Cell Culture from the Monocot *Asparagus Officianlis", The EMBO Journal*, 3, 3039–3041 (Dec. 1984).
Hibberd, K.A., "Induction, Selection, and Characterization of Mutants in Maize Cell Cultures", In: *Cell Culture and Somatic Cell Genetics of Plants*, vol. 1, Vasil, I.K., (ed.), Academic Press, Inc., Orlando, FL, 571–576 (1984).
Hickle, L.A., et al., "Analytical Chemistry of *Bacillus thuringiensis*: An Overview", In: *Analytical Chemistry of Bacillus thuringiensis*, Hickle, L.A., et al., (eds.), Developed from a Symposium Sponsored by the Division of Agrochemicals at the 198th National Meeting of the American Chemical Society, Miami Beach, FL, vii–ix, 1–8 (Sep. 10–15, 1989).
Hilder, V.A., et al., "A Novel Mechanism of Insect Resistanct Engineered into Tobacco", *Nature*, 330, 160–163 (Nov. 12, 1987).
Hodges, T.K., et al., "Genotype Specificity of Somatic Embryogenesis and Regeneration in Maize", *Bio/technology*, 4, 219–223 (Mar. 1986).
Hodges, T.K., et al., "Regeneration of Maize", In: *Biotechnology in Plant Science*, Zaitlin, M., et al., (ed.), Academic Press, Inc., Orlando, FL, 15–33 (1985).
Hoekema, A., et al., "Codon Replacement in the PGK1 Gene of *Saccharomyces cerevisiae*: Experimental Approach to Study the Role of Biased Codon Usage in Gene Expression", *Molecular and Cellular Biology*, 7, 2914–2924 (Aug. 1987).
Hofmann, C., et al., "Binding of the Delta Endotoxin from *Bacillus thuringiensis* to Brush–Border Membrane Vesicles of the Cabbage Butterfly (*Pieris Brassicae*)", *Eur. J. Biochem.*, 173, 85–91 (1988).

Hofmann, C., et al., "Specificity of *Bacillus thuringiensis* δ–Endotoxins is Correlated with the Presence of High–Affinity Binding Sites in the Brush Border Membrane of Target Insect Midguts", *Proc. Natl. Acad. Sci. USA*, 85, 7844–7848 (Nov. 1988).

Höfte, H., et al., "Monoclonal Antibody Analysis and Insecticidal Spectrum of Three Types of Lepidopteran–Specific Insecticidal Crystal Proteins of *Bacillus thuringiensis", Applied and Environmental Microbiology*, 54, 2010–2017 (Aug. 1988).

Höfte, H., et al., "Structural and Functional Analysis of a Cloned Delta Endotoxin of *Bacillus thuringiensis* berliner 1715", *Eur. J. Biochem.*, 161, 273–280 (1986).

Hollingworth, R.M., "The Biochemical and Physiological Basis of Selective Toxicity", In: *Insecticidal Biochemistry and Physiology*, Wilkinson, C.F., (ed.), Plenum Press, New York, 431–506 (1976).

Horsch, R.B., et al., "A Simple and General Method for Transferring Genes into Plants", *Science*, 227, 1229–1231 (Mar. 8, 1985).

Hu, N.T., et al., "Primary Structure of a Genomic Zein Sequence of Maize", *The EMBO Journal*, 1, 1337–1342 (1982).

Huber, H.E., et al., "*Bacillus thuringiensis* δ–Endotoxin: Composition and Activation", In: *Pathogenesis of Invertebrate Microbial Diseases*, Davidson, E.W., (ed.), Allanheld, Osmun & Co., Publishers, Inc., Totowa, NJ, 209–234 (1981).

Huber–Lukac, M., et al., "Characterization of Monoclonal Antibodies to a Crystal Protein of *Bacillus thuringiensis* subsp. *kurstaki", Infection and Immunity*, 54, 228–232 (Oct. 1986).

Imbrie–Milligan, C.W., et al., "Microcallus Formation from Maize Protoplasts Prepared from Embryogenic Callus", *Planta*, 168, 395–401 (1986).

Jarrett, P., "Potency Factors in the delta–Endotoxin of *Bacillus thuringiensis* var. *aizawi* and the Significance of Plasmids in their Control", *Journal of Applied Bacteriology*, 58, 437–448 (1985).

Jaworski, J.G., et al., "A Cerulenin Insensitive Short Chain 3–Ketoacyl–Acyl Carrier Protein Synthase in *Spinacia oleracea* Leaves", *Plant. Physiol*, 90, 41–44 (1989).

Johnson, D.E., "Toxicity of *Bacillus thuringiensis* Entomocidal Protein Toward Cultured Insect Tissue", *Journal of Invertebrate Pathology*, 38, 94–101 (1981).

Josefsson, L.G., et al., "Structure of a Gene Encoding the 1.7 S Storage Protein, Napin, from *Brassica napus", The Journal of Biological Chemistry*, 262, 12196–12201 (Sep. 5, 1987).

Kim, C.S., et al., "Improvement of Nutritional Value and Functional Properties of Soybean Glycinin by Protein Engineering", *Protein Engineering*, 3, 725–731 (1990).

King, P., et al., "Maize", In: *Handbook of Plant Cell Culture*, vol. 2, Sharp, W.R., et al., (eds.), Macmillan Publishing Company, New York, 69–91 (1984).

Klein, T.M., et al., "Advances in Direct Gene Transfer into Cereals", In: *Genetic Engineerng: Principles and Methods*, vol. 11, Setlow, J.K., (ed.), Plenum Publishing Corp., New York, 13–31 (1989).

Klein, T.M., et al., "Particle Gun Technology: A Novel Method for the Introduction of DNA into Living Cells", *Program and Abstracts for an International Symposium: "Biotechnology in Plant Science: Relevance to Agriculture in the Eighties",* Poster, #28, Ithaca, NY, 25 (Jun. 23–27, 1985).

Klein, T.M., et al., "Stable Genetic Transformation of Intact Nicotiana Cells by the Particle Bombardment Process", *Proc. Natl. Acad. Sci. USA*, 95, 5502–5505 (Nov. 1988).

Knowles, B.H., et al., "Characterization and Partial Purification of a Plasma Membrane Receptor for *Bacillus thuringiensis* var. *Kurstaki* Lepidopteran–Specific δ–Endotoxin", *J. Cell. Sci.*, 83, 89–101 (1986).

Knowles, B.H., et al., "Lectin–Like of *Bacillus thuringiensis* var. *Kurstaki* Lepidopteran–Specific Toxin in an Initial Step in Insecticidal Action", *FEBS Letters*, 168, 197–202 (Mar. 1984).

Langridge, W.H., et al., "Electric Field Mediated DNA Transformation in Plant Protoplasts", *Program and Abstracts for an International Symposium: "Biotechnology in Plant Science: Relevance to Agriculture in the Eighties",* Ithaca, NY, Poster #30, p. 25 (Jun. 23–27, 1985).

Leason, M., et al., "Inhibition of Pea Leaf Glutamine Synthetase by Methionine Sulphoximine, Phosphinithricin and Other Glutamate Analogues", *Biochemistry*, 21, 855–857 (1982).

Lee, B., "Cereal Transformation", *Plants Today*, 9–11 (Jan.–Feb. 1989).

Lörz, H., et al., "Gene Transfer to Cereal Cells Mediated by Protoplast Transformation", *Mol. Gen. Genet.,* 199, 178–182 (1985).

Lowe, K., et al., "Plant Regeneration via Organogenesis and Embryogenesis in the Maize Inbred Line B73", *Plant Science*, 41, 125–132 (1985).

Luckow, V.A., et al., "Trends in the Development of Baculovirus Expression Vectors", *Bio/Technology*, 6, 47–55 (Jan. 1988).

Lüthy, P., "Insecticidal Toxins of *Bacillus thuringiensis", FEMS Microbiology Letters*, 8, 1–7 (1980).

Malan, C., et al., "Correlation Between CuZn Superoxide Dismutase and Glutathione Reductase, and Environmental and Xenobiotic Stress Tolerance in Maize Inbreds", *Plant Science*, 69, 157–166 (1990).

Mangano, M.L., et al., "Long–Term Cold Storage of Regenerable Maize Callus", *In Vitro Cellular and Developmental Biology*, 25, Abstract No. 224, p. 66A (Mar. 1989).

Marks, M.D., et al., "Nucleotide Sequence Analysis of Zein mRNAs from Maize Endosperm", *The Journal of Biological Chemistry*, 260, 16451–16459 (Dec. 25, 1985).

Martens, J.W.M., et al., "Insecticidal Activity of a Bacterial Crystal Protein Expressed by a Recombinant Baculovirus in Insect Cells", *Applied and Environmental Microbiology*, 56, 2764–2770 (Sep. 1990).

McElroy, D., et al., "Isolation of an Efficient Actin Promoter for Use in Rice Transformation", *The Plant Cell*, 2, 163–171, (Feb. 1990).

Merryweather, A.T., et al., "Construction of Genetically Engineered Baculovirus Insecticides Containing the *Bacillus thuringiensis* subsp. *Kurstaki* HD–73 Delta Endotoxin", *Journal of General Virology*, 71, 1535–1544 (1990).

Molnar, S.J., et al., "Initiation of Totipotent Tissue Cultures from Undeveloped Axillary and Secondary Ears", *Maize Genetics Cooperation Newsletter*, 54, 52–53 (Mar. 31, 1980).

Montoliu, L., et al., "A Tamdem of α–Tubulin Genes Preferentially Expressed in Radicular Tissues from *Zea mays", Plant Molecular Biology*, 14, 1–15 (1989).

Morris, G.D., "Ciba–Geigy Enters the $1.5–Billion/Year Corn Biotech Race", *Chemical Week* (Sep. 12, 1990).

Mundy, J., et al., "Selective Expression of a Probable Amylase/Protease Inhibitor in Barley Aleurone Cells: Comparison to the Barley Amylase/Subtilisin Inhibitor", *Planta*, 169, 51–63 (1986).

Murphy, D.W., et al., "*Bacillus thuringiensis* Enzyme–Digested Delta Endotoxin: Effect on Cultured Insect Cells", *Science*, 194, 954–956 (Nov. 26, 1976).

Nishiitsutsuji–Uwo, J., et al., "Mode of Action of *Bacillus thuringiensis* δ–Endotoxin: Effect on TN–368 Cells", *Journal of Invertebrate Pathology*, 34, 267–275 (1979).

Ochatt, S.J., et al., "Selection for Salt/Drought Tolerance using Isolated Protoplasts and Protoplast–Derived Calli of Colt Cherry (*Prunus avium×pseudocerasus*)", In: *Progress in Plant Protoplast Research*, Puite, K.J., et al., (eds.), Kluwer Academic Publishers, Dordrecht, The Netherlands, p. 391–392 (1988).

Oeda, K., et al., "Formation of Crystals of the Insecticidal Proteins of *Bacillus thuringiensis* subsp. *aizawai* IPL7 in *Escherichia coli", Journal of Bacteriology*, 171, 3568–3571 (Jun. 1989).

O'Reilly, D.R., et al., "A Baculovirus Blocks Insect Molting by Producing Ecdysteroid UDP–Glucosyl Transferase", *Science*, 245, 1110–1112 (Sep. 8, 1989).

Park, W.D., et al., "High–Level, Sucrose–Inducible Expression of a Chimeric Palatin–GUS Gene In Leaf Explants of Transgenic Tobacco Plants", *Journal of Cellular Biochemistry*, 13D, Abstract No. M 343, p. 310 (Mar. 27–Apr. 7, 1989).

Perlak, F.J., et al., "Expression of *Bacillus thuringiensis* Proteins in Transgenic Plants", In: *Biotechnology, Biological Pesticides and Novel Plant–Pest Resistance for Insect Pest Management*, Roberts, D.W., et al., (eds.), Insect Pathology Resource Center, Boyce Thompson Institute for Plant Research, Cornel University, Ithaca, NY, 77–81 (1988).

Perlak, F.J., et al., "Insect Resistant Cotton Plants", *Bio/technology*, 8, 939–943 (Oct. 1990).

Poehlman, J.M., et al., In: *Breeding Field Crops*, 3rd Edition, AVI Publishing Company, Inc., Westport, CT, 149–152 (1987).

Poethig, R.S. "Maize—The Plant and Its Parts", In: *Maize for Biological Research*, Sheridan, W.F., (ed.), Plant Molecular Biology Association., Charlottesville, VA, 9–18 (1982).

Potrykus, I., et al., "Direct Gene Transfer: State of the Art and Future Potential", *Plant Molecular Biology Reporter*, 3, 117–128 (Summer 1985).

Randolph, L.F., et al., "Developmental Morphology of the Caryopsis in Maize", *Journal of Agricultural Research*, 53, 881–916 (Dec. 15, 1936).

Rhodes, C.A., et al., "Cytogenetic Stability of Aneuploid Maize Tissue Cultures", *Can. J. Genet. Cytol.*, 28, 374–384 (1986).

Rhodes, C.A., et al., "Factors Affecting Tissue Culture Initiation from Maize Tassels", *Plant Science*, 46, 225–232 (1986).

Rice, T.B., "Tissue Culture Induced Genetic Variation in Regenerated Maize Inbreds", *Proceedings of the 37th Annual Corn & Sorghum Industry Research Conference*, 148–162 (1982).

Rosahl, S., et al., "Expression of a Tuber–Specific Storage Protein In Transgenic Tobacco Plants: Demonstration Of An Esterase Activity", *EMBO. J*, 6, Press Limited, Oxford, England, 1155 (1987).

Roth, B.A., et al., "Genetic Regulation of Transient Expression of Maize Anthocyanin Pathway Genes Introduced into Intact Maize Tissues by Microprojectile Bombardment", *Journal of Cellular Biochemistry*, 13D, Abstract No. M 344, p. 310 (Mar. 27–Apr. 7, 1989).

Roush, R.T., et al., "Ecological Genetics of Insecticidal and Acaricide Resistance", *Ann. Rev. Entomol.*, 32, 361–380 (1987).

Ryan, A.J., et al., "The Expression of the Napin Gene Under the Control of Its Own Promoter in Transgenic Tobacco Plants", *Journal of Cellular Biochemistry*, 13D, Abstract No. M 345, p. 310 (Mar. 27–Apr. 7, 1989).

Sanford, J.C., "The Biolistic Process", *Plant Physiology*, 89, Abstract No. 9, p. 2 (Apr. 1989).

Sanford, J.C., et al., "Delivery of DNA into Regenerable Tissues of Monocots, Using High–Velocity Microprojectiles", Grant Application No. 86–0183, United States Department of Agriculture, Science and Education, 57 p. (Feb. 27, 1986).

Sass, J.E., "Comparative Leaf Number in the Embryos of Some Types of Maize", *Iowa State Coll. J. Sci.*, 25, 509–512 (1951).

Schafer, W., et al., "T–DNA Integration and Expression in a Monocot Crop Plant After Induction of Agrobacterium", *Nature*, 327, 529–532 (Jun. 11, 1987).

Schardl, C.L., et al., "Design and Construction of a Versatile System for the Expression of Foreign Genes in Plants", *Gene*, 61, 1–11 (1987).

Schnepf, H.E., et al., "Delineation of a Toxin–Encoding Segment of a *Bacillus thuringiensis* Crystal Protein Gene", *The Journal of Biological Chemistry*, 260, 6273–6280 (1985).

Schnepf, H.E., et al., "Specificity–Determining Regions of a Lepidopteran–Specific Insecticidal Protein Produced by *Bacillus thuringiensis", The Journal of Biological Chemistry*, 265, 20923–20930 (Dec. 5, 1990).

Shaner, D.L., et al., "Mechanism of Action of the Imidazolinones and Cell Culture Selection of Tolerant Maize", In: *Biotechnology in Plant Sciences*, Zaitlin, M., et al., (eds.), Academic Press, Orlando, FL, 287–299 (1985).

Sharman, B.C., "Developmental Anatomy of the Shoot of *Zea mays* L.", *Annals of Botany*, VI, 246–281 (Apr. 1942).

Shields, R., "Towards Insect–Resistant Plants", *Nature*, 328, 12–13 (Jul. 2, 1987).

Shivakumar, A.G., et al., "Vegetative Expression of the γ–Endotoxin Genes of *Bacillus thuringiensis* subsp. *kurstaki* in *Bacillus subtilis", Journal of Bacteriology*, 166, 194–204 (Apr. 1986).

Shotwell, M.A., et al., "Analysis of Seed Storage Protein Genes of Oats", *The Journal of Biological Chemistry*, 265, 9652–9658 (Jun. 15, 1990).

Smith, G.E., et al., "Molecular Engineering of the *Autographa californica* Nuclear Polyhedrosis Virus Genome: Deletion Mutations Within the Polyhedrin Gene", *Journal of Virology*, 46, 584–593 (May 1983).

Smith, I.K., et al., "Properties and Functions of Gluthatione Reductase in Plants", *Physiol. Plant.*, 77, 449–456 (1989).

St. Julian, G., et al., "Bacteria, Spirochetes, and Rickettsia as Insecticides", *Annals of the New York Academy of Sciences*, 217, 65–75 (1973).

Stalker, D.M., et al., "Herbicide Resistance in Transgenic Plants Expressing a Bacterial Detoxification Gene", *Science*, 242, 419–422 (Oct. 21, 1988).

Stiefel, V., et al., "Expression of a Maize Cell Wall Hydroxyproline–Rich Glycoprotein Gene in Early Leaf and Root Vascular Differentiation", *The Plant Cell*, 2, 785–793 (Aug. 1990).

Stolle, C.A., et al., "Cellular Factor Affecting the Stability of β–globulin mRNA", *Gene*, 62, 65–74 (1988).

Strauch, E., et al., "Cloning of a Phosphinothricin N–Acetyltransferase Gene from Streptomyces Viridochromogenes Tu494 and its Expression in *Streptomyces lividans* and *Escherichia coli", Gene*, 63, 65–74 (1988).

Stroo, H.F., et al., "Heterotrophic Nitrification in an Acid Forest Soil and by an Acid–Tolerant Fungus", *Applied and Environmental Microbiology*, 52, 1107–1111 (Nov. 1986).

Suprasanna, P., et al., "Plantlet Regeneration from Glume Calli of Maize (*Zea mays* L.)", *Theor. Appl. Genet.*, 72, 120–122 (1986).

Thomas, W.E., et al., "Mechanism of Action of *Bacillus thuringiensis* var *israelensis* Insecticidal δ–Endotoxin", *FEBS Letters*, 154, 362–368 (Apr. 1983).

Tojo, A., et al., "Dissolution and Degradation of *Bacillus thuringiensis* δ–Endotoxin by Gut Juice Protease of the Silkworm *Bombyx mori", Applied and Environmental Microbiology*, 45, 576–580 (Feb. 1983).

Tomes, D.T., "Cell Culture, Somatic Embryogenesis and Plant Regeneration in Maize, Rice, Sorghum and Millets", In: *Cereal Tissue and Cell Culture*, Bright, S.W.J., et al., (eds.), Martinus Nijnoff/Dr. W. Junk, Amsterdam, The Netherlands, 175–203 (1985).

Tomes, D.T., "Initiation of Embryogenic Callus Cultures from Immature Embryos of Elite Corn (*Zea mays* L.) Germplasm", *In Vitro*, 20, Abstract No. 146, p. 276 (Mar. 1984).

Tomes, D.T., et al., "The Effect of Parental Genotype on Initiation of Embryogenic Callus from Elite Maize (*Zea mays* L.) Germplasm", *Theor. Appl. Genet.*, 70, 505–509 (1985).

Torne, J.M., et al., "Regeneration of Plants from Meoscotyl Tissue Cultures of Immature Embryos of *Zea mays* L.", *Plant Science Letters*, 17, 339–344 (1980).

Vaeck, M., et al., "*Bacillus thuringiensis* Endotoxin Gene Expression and Insect Resistance in Higher Plants", *Pesticide Science*, 20, 319–320 (1987).

Vaeck, M., et al., "Engineering Improved Crops for Agriculture: Protection from Insects and Resistance to Herbicides", In: *Plant Gene Systems and Their Biology*, Key, J.L., et al., (eds.), Alan R. Liss, Inc., New York, 171–181 (1987).

Vaeck, M., et al., "Engineering of Insect Resistant Plants Using a *B. thuringiensis* Gene", In: *Molecular Stragegies for Crop Protection*, New York, Alan R. Liss, Inc., 355–366 (1987).

Vaeck, M., et al., "Insect Resistance in Transgenic Plants Expressing *Bacillus thuringiensis* Toxin Gens", *An. Soc. Entomol. Brasil*, 16, 427–435, (1987).

Vaeck, M., et al., "Protein Engineering in Plants: Expression of *Bacillus thuringiensis* Insecticidal Protein Genes", *Cell Culture and Somatic Cell Genetics of Plants*, 6, 425–439, (1989).

Vaeck, M., et al., "Transgenic Plants Protected from Insect Attack", *Nature*, 328, 33–37, (Jul. 2, 1987).

van den Elzen, P.J., et al., "A Chimaeric Hygromycin Resistance Gene as a Selectable Marker in Plant Cells", *Plant Molecular Biology*, 5, 299–302, (1985).

van den Elzen, P.J., et al., "Simple Binary Vectors for DNA Transfer to Plant Cells", *Plant Molecular Biology*, 5, 149–154, (1985).

Van Lammeren, A.A., "Developmental Morphology and Cytology of the Young Maize Embryo (*Zea mays* L.)", *Acta Bot. Neerl.*, 35, 169–188 (Aug. 1986).

Vasil, I.K., "Isolation and Culture of Protoplasts of Grasses", *International Review of Cytology, Supplement* 16, Bourne, G.H., et al., (eds.), Academic Press, New York, 79–88 (1983).

Vasil, V., et al., "Histology of Somatic Embryogenesis in Cultured Immature Embryos of Maize (*Zea Mays* L.)", *Protoplasma*, 127, 1–8 (1985).

Viotti, A., et al., "Each Zein Gene Class Can Produce Polypeptides of Different Sizes", *The EMBO Journal*, 4, 1103–1110 (1985).

Watson, S.A., "Corn Marketing, Processing and Utlilization", In: *Corn and Corn Improvement*, 3rd Edition, Sprague G.F., et al., (eds.), American Society of Agronomy, Inc., et al., Madison, WI, 881–939 (1988).

Weigel, Jr., R.C., et al. "Somatic Embryogenesis in Barley", *In Vitro*, 20, Abstract No. 147, p. 277 (Mar. 1984).

Weissinger, A., et al., "Maize Transformation via Microprojectile Bombardment", In: *Genetic Improvements of Agriculturally Important Crops*, Fraley, R.T., et al., (eds.), Cold Spring Harbor Laboratory, Cold Spring Harbor, NY, 21–25 (1988).

Weissinger, A., et al., "Microprojectile Bombardment for Maize Transformation", *In Vitro Cellular and Developmental Biology*, 23, Program Issue, 38th Annual Meeting of the Tissue Culture Association, Washington, D.C., Abstract No. 254 (Mar. 1987).

Wernicke, W., et al., "Adventitious Embryoid and Root Formation from Rice Leaves", *Z. Pflanzenphysiol. Bd.*, 103, 361–365 (1981).

Werr, W. et al., "Structure of the Sucrose Synthase Gene on Chromosome 9 of *Zea mays* L.", *The EMBO Journal*, 4, 1373–1380 (1985).

Withers, L., et al., "Proline: A Novel Cryoprotectant for the Freeze Preservation of Cultured Cells of *Zea mays* L.", *Plant Physiology*, 64, 675–678 (1979).

Witt, D.P., et al., "Cytotoxicity of *Bacillus thuringiensis* δ–Endotoxins to Cultured Cf–1 Cells Does Not Correlate with In Vivo Activity Toward Spruce Budworm Larvae", In: *Fundamental and Applied Aspects of Invertebrate Pathology*, Samson, R.A., et al., (eds.), Fourth International Colloquium of Invertebrate Pathology, Wangingen, The Netherlands, 3–6 (Aug. 18–22, 1986).

Wohlleben, W., et al., "Nucleotide Sequence of the Phosphinothricin N–Acetyltransferase Gene from *Streptomyces viridochromogenes* Tü494 and Its Expression in *Nicotania tabacum", Gene*, 70, 25–37 (1988).

Wood, M., "Blast Those Genes!", *Agricultural Research*, 2 p. (Jun. 1989).

Yang, N.S., et al., "Maize Sucrose Synthase–1 Promoter Directs Phloem Cell–Specific Expression of Gus Gene in Transgenic Tobacco Plants", *Proc. Natl. Acad. Sci. USA*, 87, 4144–4148 (Jun. 1990).

Yenofsky, R.L., et al., "Isolation and Characterization of a Soybean (*Glycine max*) Lipoxygenase–3 Gene", *Mol. Gen. Genet.*, 211, 215–222 (1988).

* cited by examiner

PHI $R_o$ PLANTS

PHI $R_1$ GENERATION

PH2 CALLUS

FERTILE TRANSGENIC CORN PLANTS

This is a division of application Ser. No. 08/618,749, filed Mar. 20, 1996, now U.S. Pat. No. 5,780,708, which is a division of application Ser. No. 08/285,488, filed Aug. 3, 1994, now U.S. Pat. No. 5,508,468, issued Apr. 16, 1996, which is a continuation of application Ser. No. 07/636,089, filed Dec. 28, 1990 now abandoned, which is a continuation-in-part of U.S. patent application Ser. No. 07/508,045, filed Apr. 11, 1990, now U.S. Pat. No. 5,484,956 issued Jan. 16, 1996, which in turn is a continuation-in-part of U.S. patent application Ser. No. 07/974,379, filed Nov. 10, 1992, now U.S. Pat. No. 5,538,877 issued Jun. 23, 1996 which in turn is a continuation of U.S. patent application Ser. No. 07/467,983, filed Jan. 22, 1990, now abandoned, all of which are incorporated by reference herein.

FIELD OF THE INVENTION

This invention relates to fertile transgenic plants of the species *Zea mays* (oftentimes referred to herein as maize or corn). The invention further relates to producing fertile transgenic plants via particle bombardment and subsequent selection techniques.

BACKGROUND OF THE INVENTION

Genetic engineering of plants, which entails the isolation and manipulation of genetic material (usually in the form of DNA or RNA) and the subsequent introduction of that genetic material into a plant or plant cells, offers considerable promise to modern agriculture and plant breeding. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Once a gene has been identified, cloned, and engineered, it is still necessary to introduce it into a plant of interest in such a manner that the resulting plant is both fertile and capable of passing the gene on to its progeny.

A variety of methods have been developed and are currently available for the transformation of various plants and plant cells with DNA. Generally, these plants have been dicotyledonous, and some success has been reported with certain of the monocotyledonous cereals. However, some species have heretofore proven untransformable by any method. Thus, previous to this discovery, no technology had been developed which would permit the production of stably transformed *Zea mays* plants in which the introduced recombinant DNA is transmitted through at least one complete sexual cycle. This failure in the art is well documented in the literature and has been discussed in a number of recent reviews (I. Potrykus, *Trends in Biotechnology,* 7, 269 (1989); K. Weising et al., *Ann. Rev. of Genetics,* 22, 421 (1988); F. Cocking et al., *Science,* 236, 1259 (1987)).

Some of the techniques attempted, or proposed, for introducing DNA into corn cells include electroporation, microinjection, microprojectile bombardment, liposome fusion, Agrobacterium-mediated transfer, macroinjection, and exposure to naked DNA in solution.

For example, J. DeWet et al., *Experimental Manipulation of Ovule Tissue,* G. Chapman et al., eds., Longman, Inc., New York (1985) at pages 197–269 and Y. Ohta, *PNAS USA,* 83, 715 (1986) reported the introduction of DNA into maize by mixing pollen grains with DNA solutions, and applying the pollen to maize silks. In these papers, there is no molecular data confirming the introduction of the exogenous DNA into the corn cells. Arntzen et al. in published European Patent Application No. 275,069 describe the incubation of DNA with maize pollen followed by pollination of maize ears and formation of seeds. The plants derived from these seeds were reported to contain the introduced DNA, but there is no suggestion that the introduced DNA was transmitted through a complete sexual cycle.

A. Graves et al., *Plant Mol. Biol.,* 3, 43 (1986) reported Aarobacterium-mediated transformation of *Zea mays* seedlings. The evidence was based upon assays which can sometimes be unreliable. To date, there have been no further reported successes with pollen and Agrobacterium-mediated transfer techniques.

Microprojectile bombardment has been reported to yield transformed corn cells. The technique is disclosed in Sanford et al., *Part. Sci. & Techn.,* 5, 27 (1987) as well as in published European patent application number 331,855 of J. C. Sanford et al. which is based upon U.S. Ser. No. 07/161,807, filed Feb. 29, 1988. Klein et al., *Plant Physiol.,* 91, 440 (1989) describe production of transformed corn cells, using microprojectile bombardment. However, the cells used were not capable of regeneration into plants. Thus, no protocols have been published describing the introduction of DNA by a bombardment technique into cultures of regenerable maize cells of any type. No stable introduction of a gene has been reported that results from bombardment of maize callus followed by regeneration fertile plants and transmission of the introduced gene through at least one sexual cycle. D. McCabe et al., in published European patent application No. 270,356, disclose the bombardment of maize pollen with DNA, the application of the pollen to silks, and the formation of seeds which reportedly contain the exogenous DNA. However, there is no evidence that the DNA was transmitted through a complete sexual cycle, and no further results have been reported by this group.

Electroporation of corn protoplasts has been reported to result in transformed cells by M. E. Fromm et al., *Nature,* 319, 791 (1986) although these cells did not provide regenerated plants. Electroporation of corn protoplasts was also reported by C. Rhodes et al., *Science,* 240, 204 (1988). Although the recipient cells were transformed and, in the latter case, were able to regenerate into plants, the plants themselves were sterile. In addition, methods for the production of the cell line used by Rhodes et al. were not reproducible.

A further stumbling block to the successful production of fertile transgenic maize plants has been in selecting those few transformants in such a manner that neither the regeneration capacity (in the case of protplasts or cell cultures) nor the fertility of the transformants are destroyed. Due to the generally low level of transformants produced by a transformation technique, some sort of selection procedure is often necessary. However, selection generally entails the use of some toxic agent, e.g., a herbicide or antibiotic, which may be detrimental to either the regenerability or the resultant plant fertility.

On the other hand, it has been known that untransformed corn protoplasts, cultured cells and callus at least can be regenerated to form mature plants and that the resulting plants are often fertile. For example, R. D. Shillito et al., *Bio/Technology,* 7, 581 (1989), and L. M. Prioli et al., *Bio/Technology,* 7, 589 (1989) discuss methods for producing protoplasts from cell cultures and recovering fertile plants therefrom. C. A. Rhodes et al., *Bio/Technolooy,* 6, 56 (1988) disclose attempts to regenerate maize plants from protoplasts isolated from embryogenic maize cell cultures.

However, it has not been possible for the art worker to determine which maize tissues or cultures are appropriate recipients for exogenous DNA, e.g., contain a useful number of cells which are receptive to and which will stably integrate the exogenous DNA, and at the same time be a part of the germline, i.e., part of the cell lineage that leads to the next plant generation.

The art is thus faced with a dilemma. While certain transformation techniques have been proposed or reported to produce transformed maize cells and certain cells and tissues have been proposed to be potential recipients due to their ability to regenerate plants, the art has failed to find a combination of techniques which would successfully produce transformed maize plants able to transmit the introduced DNA through one complete sexual cycle.

It is thus an object of the present invention to produce fertile, stably-transgenic, *Zea mays* plants and seeds which transmit the introduced gene to progeny. It is a further object to produce such stably-transgenic plants and seeds by a particle bombardment and a selection process which results in a high level of viability for at least a portion of the transformed cells. It is a further object to produce fertile, stably-transgenic plants of other graminaceous cereals besides maize.

References Cited

The references listed below are incorporated by reference herein.

Armstrong, C L, et al. (1985) Planta 164:207–214

Callis, J, et al. (1987) Genes & Develop 1:1183–1200

M. Bevan et al. (1983) Nuc Acids Res 11:36a

Chu, C C, et al. (1975) Sci Sin (Peking) 18:659–668

Cocking, F, et al. (1987) Science 236:1259–1262

DeWet et al. (1985) Proc Natl Sci USA 82:7870–7873

Freeling, J C, et al. (1976) Maydica XXI:97–112

Graves, A, et al. (1986) Plant Mol Biol 7:43–50

Green, C, et al. (1975) Crop Sci 15:417–421

Green, C, et al. (1982) Maize for Biological Research, Plant Mol. Biol. Assoc., pp 367–372

Gritz, L, et al. (1983) Gene 25:179–188

Guilley, H, et al. (1982) Cell 30:763–773

Hallauer, A R, et al. (1988) Corn and Corn Improvement, 3rd ed., Agronomy Society of America, pp 469–564

Jefferson, R, et al. (1987) EMBO J 6:3901–3907

Kamo, K, et al. (1985) Bot Gaz 146:327–334

Klein, T, et al. (1989) Plant Physiol 91:440–444

Klein, T, et al. (1988a) Proc Natl Acad Sci USA 85:4305–9

Klein, T, et al. (1988b) Bio/Technology 6:559–563

Lu, C, et al. (1982) Theor Appl Genet 62:109–112

McCabe, D, et al. (1988) Bio/Technology 6:923–926

Murashige, T, et al. (1962) Physiol Plant 15:473–497

Neuffer, M, (1982) Maize for Biological Research, Plant Mol Biol Assoc, pp 19–30

Phillips, R, et al. (1988) Corn and Corn Improvement, 3rd ed., Agronomy Society of America, pp 345–387

Potrykus, I (1989) Trends in Biotechnology 7:269–273

Rhodes, C A, et al. (1988) Science 240:204–7

Sambrook, J, et al. (1989) Molecular Cloning: A Laboratory Manual, 2nd ed., Cold Spring Harbor Laboratory Press Sanford, J, et al. (1987) Part Sci & Techn 5:27–37

Weising, K, et al., (1988) Ann Rev of Genetics 22:421–478

Yanisch-Perron, L, et al. (1985) Gene 33:109–119

SUMMARY OF THE INVENTION

The present invention relates to fertile transgenic *Zea mays* plants containing recombinant DNA, preferably chromosomally integrated recombinant DNA, which is heritable by progeny thereof.

The invention further relates to all products derived from transgenic *Zea mays* plants, plant cells, plant parts, and seeds.

The invention further relates to transgenic *Zea mays* seeds stably containing recombinant DNA and progeny which have inherited the recombinant DNA. The invention further relates to the breeding of transgenic plants and the subsequent incorporation of recombinant DNA into any zea mays plant or line.

The invention further relates to a process for producing fertile transgenic *Zea mays* plants containing recombinant DNA. The process is based upon microprojectile bombardment, selection, plant regeneration, and conventional backcrossing techniques.

The invention further relates to a process for producing fertile transformed plants of graminaceous species other than *Zea mays* which have not been reliably transformed by traditional methods such as electroporation, Agrobacterium, injection, and previous ballistic techniques.

The invention further relates to regenerated fertile mature maize plants obtained from transformed embryogenic tissue, transgenic seeds produced therefrom, and R1 and subsequent generations.

A preferred embodiment of the present invention is a fertile, transgenic corn plant that has been stably transformed with a recombinant, chimeric gene which is expressed as a seed storage protein, e.g., as the 10 kD zein protein, so that the level of at least one amino acid is elevated above that present in the parent, nontransformed lines. Expression of multiple copies of said gene or overexpression thereof, can substantially increase the whole kernel levels of certain amino acids, such as lysine, methionine, threonine and the like. As used herein, the term "substantially increased" means that the level of a given amino acid is at least 10–20% above that present in the corresponding plant or plant part which has not been transformed with said seed storage protein gene.

In preferred embodiments, this invention produces the fertile, transgenic plants by means of a recombinant DNA-coated microprojectile bombardment of clumps of friable embryogenic callus, followed by a controlled regimen for selection of transformed callus lines.

DESCRIPTION OF THE PREFERRED EMBODIMENTS

Figure 1:
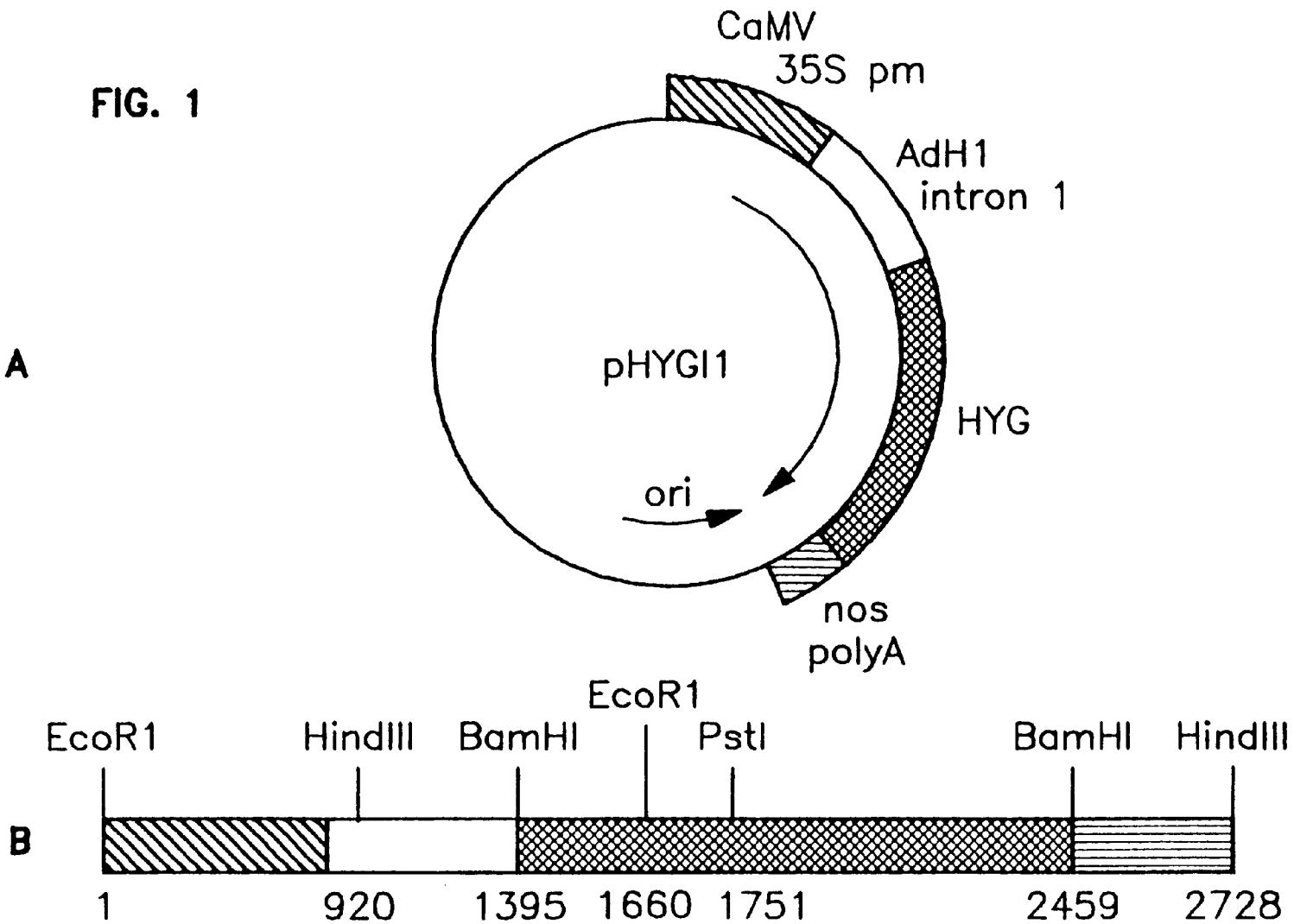
FIG. 1A shows a map of plasmid vector pHYGI1 utilized in EXAMPLE I.
FIG. 1B shows the relevant part of linearized pHYGI1 encompassing the HPT coding sequence and associated regulatory elements. The base pair numbers start from the 5' nucleotide in the recognition sequence for the indicated restriction enzymes, beginning with the EcoRI site at the 5' end of the CaMV 35S promoter.

The present invention is directed to the production of fertile transgenic plants and seeds of the species *Zea mays* and to the plants, plant tissues, and seeds derived from such transgenic plants, as well as the subsequent progeny and products derived therefrom, preferably those transgenic *Zea mays* plants having improved food or feed value. The transgenic plants produced herein include all plants of this species, including field corn, popcorn, sweet corn, flint corn and dent corn.

"Transgenic" is used herein to include any cell, cell line, callus, tissue, plant part or plant, the genotype of which has been altered by the presence of recombinant DNA, which DNA has also been referred to in the art of genetic engineering as "heterologous DNA," "exogenous DNA" or "foreign DNA," wherein said DNA was introduced into the genotype by a process of genetic engineering, or which was initially introduced into the genotype of a parent plant by such a process and is subsequently transferred to later generations by sexual crosses or asexual propagation. As used herein, "genotype" refers to the sum total of genetic material within a cell, either chromosomally, or extrachromosomally borne. Therefore, the term "transgenic" as used herein does not encompass the alteration of the genotype of *Zea mays* by conventional plant breeding methods or by naturally occurring events such as random cross-fertilization, viral infection or spontaneous mutation.

By "heritable" is meant that the DNA is capable of transmission through at least one complete sexual cycle of a plant, i.e., it is passed from one plant through its gametes to its progeny plants.

The transgenic plants of this invention may be produced by (i) establishing a regenerable cell culture, preferably a friable embryogenic callus, (ii) transforming said cell culture by a microprojectile bombardment technique, (iii) identifying or selecting transformed cells, and (iv) regenerating fertile transgenic plants from the transformed cells. Some of the plants of this invention may be produced from the transgenic seed produced from the fertile transgenic plants using conventional crossbreeding techniques to develop transgenic elite lines and varieties, or commercial hybrid seed containing recombinant DNA.

I. Plant Lines and Tissue Cultures

The cells which have been found particularly useful to produce the fertile transgenic maize plants herein are those callus cells which are regenerable, both before and after undergoing a selection regimen as detailed further below. Generally, these cells will be derived from meristematic tissue which contains cells which have not yet terminally differentiated. Such tissue in graminaceous cereals in general and in maize, in particular, comprise tissues found in juvenile leaf basal regions, immature tassels, immature embryos, and coleoptilar nodes. Preferably, immature embryos are used. Methods of preparing and maintaining callus from such tissue and plant types are well known in the art and details on so doing are available in the literature, c.f. Phillips et al. (1988), the disclosure of which is hereby incorporated by reference.

The specific callus used must be able to regenerate into a fertile plant. The specific regeneration capacity of particular callus is important to the success of the bombardment/selection process used herein because during and following selection, regeneration capacity may decrease significantly. It is therefore important to start with cultures that have as high a degree of regeneration capacity as possible. Callus which is more than about 3 months and up to about 36 months of age has been found to have a sufficiently high level of regenerability and thus is preferred. The regenerative capacity of a particular culture may be readily determined by transferring samples thereof to regeneration medium and monitoring the formation of shoots, roots, and plantlets. The relative number of plantlets arising per petri dish or per gram fresh weight of tissue may be used as a rough quantitative estimate of regeneration capacity. Generally, a culture which will produce at least one plant per gram of callus tissue is preferred.

While maize callus cultures can be initiated from a number of different plant tissues, the cultures useful herein are preferably derived from immature maize embryos which are removed from the kernels of an ear when the embryos are about 1–3 mm in length. This length generally occurs about 9–14 days after pollination. Under aseptic conditions, the embryos are placed on conventional solid media with the embryo axis down (scutellum up). Callus tissue appears from the scutellum after several days to a few weeks. After the callus has grown sufficiently, the cell proliferations from the scutellum may be evaluated for friable consistency and the presence of well-defined embryos. By "friable consistency" it is meant that the tissue is easily dispersed without causing injury to the cells. Tissue with this morphology is then transferred to fresh media and subcultured on a routine basis about every two weeks. Sieving to reduce clumping and/or to increase cell surface area may be employed during the subculturing period.

The callus initiation media is preferably solid. In preferred embodiments, the initiation/maintenance media is typically based on the N6 salts of Chu et al. (1975) as described in Armstrong et al. (1985) or the MS salts of Murashige et al. (1962). The basal medium is supplemented with sucrose and 2,4-dichlorophenoxyacetic acid (2,4-D). Supplements such as L-proline and casein hydrolysate have been found to improve the frequency of initiation of callus cultures, morphology, and growth. The cultures are generally maintained in the dark, though low light levels may also be used. The level of synthetic hormone 2,4-D, necessary for maintenance and propagation, should be generally about 0.3 to 3.0 mg/l.

Although successful transformation and regeneration has been accomplished herein with friable embryogenic callus, this is not meant to imply that other transformable regenerable cells, tissue, or organs cannot be employed to produce the fertile transgenic plants of this invention. The only actual requirement for the cells which are transformed is that after transformation they must be capable of regeneration of a plant containing the recombinant DNA following the particular selection or screening procedure actually used.

For example, cells grown in liquid suspension culture may be used. To establish these cultures, the type II callus, after 4–6 months, is transferred to liquid growth media. Methods and references for the production of regenerable suspension cell cultures are given by C. E. Green et al. in *Maize for Biological Research*, Plant Molec. Biol. Assoc. (1982) at pages 367–372, R. Phillips et al., *Corn and Corn Improvement*, Agronomy Soc. Amer., (3d ed., 1988) at pages 345–387, and I. Vasil, *Cell Culture and Somatic Cell Genetics of Plants*, Vol. I, *Laboratory Procedures and Their Applications*, Academic Press (1984) at pages 152–158. Typically, the liquid growth media for suspension cultures is of similar formulation to the solid callus induction media. ABA (abscisic acid) ($10^{-7}$M) may be added to the liquid growth media to augment regenerative capacity and enhance culture vitality. It is preferred that the callus not be sieved prior to introduction into the liquid media.

The cultures in liquid media are subcultured as appropriate for maintaining active growth and their regenerative properties. In preferred embodiments, the cultures are subcultured once a week at a 1:8–9 dilution with fresh growth medium.

II. DNA Used for Transformation

As used herein, the term "recombinant DNA" refers to DNA that has been derived or isolated from any source, that may be subsequently chemically altered, and later introduced into *Zea mays*. An example of recombinant DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Therefore "recombinant DNA" includes completely synthetic DNA, semi-synthetic DNA, DNA isolated from biological sources, and DNA derived from introduced RNA. Generally, the recombinant DNA is not originally resident in the *Zea mays* genotype which is the recipient of the DNA, but it is within the scope of the invention to isolate a gene from a given *Zea mays* genotype, and to subsequently introduce multiple copies of the gene into the same genotype, e.g., to enhance production of a given gene product such as a storage protein.

The recombinant DNA includes but is not limited to, DNA from plant genes, and non-plant genes such as those from bacteria, yeasts, animals or viruses; modified genes, portions of genes, chimeric genes, including genes from the same or different *Zea mays* genotype.

The recombinant DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant corn plant. For example, the recombinant DNA may itself comprise or consist of a promoter that is active in *Zea mays*, or may utilize a promoter already present in the *Zea mays* genotype that is the transformation target.

The compositions of, and methods for, constructing recombinant DNA which can transform certain plants are well known to those skilled in the art, and the same compositions and methods of construction may be utilized to produce the DNA useful herein. The specific composition of the DNA is not central to the present invention and the invention is not dependent upon the composition of the specific recombinant DNA used. K. Weising et al., *Ann. Rev. Genetics,* 22, 421 (1988) describes suitable DNA components, selectable marker genes, reporter genes, enhancers, introns, and the like, as well as provides suitable references for compositions therefrom. J. Sambrook et al., *Molecular Cloning: A Laboratory Manual*, Cold Spring Harbor Laboratory Press (2d ed., 1989), provides suitable methods of construction. Generally, the recombinant DNA will be relatively small, i.e., less than about 30 kb to minimize any susceptibility to physical, chemical, or enzymatic degradation which is known to increase as the size of the DNA increases.

Suitable recombinant DNA for use herein includes all DNA which provides for, or enhances, a beneficial feature of the resultant transgenic corn plant. The DNA may encode proteins or antisense RNA transcripts in order to promote increased food values, higher yields, pest resistance, disease resistance, herbicide resistance, and the like. For example, the DNA can encode a DHDP synthase, as does the dap A gene, for increased lysine production; *Bacillus thuringiensis* (Bt), δ-endotoxin or a protease inhibitor for insect resistance; bacterial EPSP synthase for resistance to glyphosate herbicide; and chitinase or glucan endo-1,3-p-glucosidase for fungicidal properties. Examples of suitable recombinant DNA are listed in Table 1, below.

TABLE 1

Eukaryptic genes transferred to higher plants

| Origin of gene | Transferred constructs | Transformed species | Mode of foreign gene expression | References |
|---|---|---|---|---|
| Animals | | | | |
| Drosophila heat shock gene hsp 70 | 5' hsp70/nptII/3' ocs | tobacco (plants, tumors) | + temperature-dependent and organ-specific | 308, 309 |
| Drosophila copia element LTR | 5' copia/cat | rice, wheat and sorghum (protoplasts) | (–) transient, but strong | 245 |
| firefly luciferase gene | 5' CaMV 35S/luciferase cDNA/3' nos<br>5' CaMV 19S/luciferase cDNA/3' nos<br>5' deletion series | tobacco (plants)<br>carrot (protoplasts) | —<br>(+) transient | 246, 247 |

TABLE 1-continued

| Origin of gene | Transferred constructs | Transformed species | Mode of foreign gene expression | References |
|---|---|---|---|---|
| Eukaryptic genes transferred to higher plants | | | | |
| Rabbit β-globin gene | genomic | tobacco (tumors) | (−) not expressed | 293 |
| Human α-globin gene | 5' nos/α-globin | tobacco (plants) | (+) incorrect transcript processing | 355 |
| Chicken α-actin gene | genomic | tobacco (tumors) | (−) not expressed | 189 |
| Chicken ovalbumin gene | genornic | tobacco (tumors) | (+) incorrect transcript processing | 189 |
| Mouse metallothionein gene (mmt) | 5' mmt/cat | tobacco (tumors) | (−) not expressed | 9 |
| Mouse dihydrofolate reductase gene (DHFR) | 5' CaMV 35S/DBFR-cDNA/ 3' nos | Petunia (plants) | + expression confers methotrexate resistance | 96 |
| Human growth hormone gene(hgh) | 5' CaMV 3 5S/hgh | tobacco (plants, tumors) | (+) incorrect transcript processing | 239 |
| | 5' nos/hgh/3' nos | tobacco and sunflower (tumors) | (+) transcription, but neither processing nor translation | 20 |
| | 5' CaMV 35S/hgh/hgh 3' | tobacco (plants) | (+) incorrect transcript polyadenylation | 167 |
| SV40 early genes | 5' SV401cat | tobacco (tumors) | (−) not expressed | 9 |
| | 5' CaMV 35S/ca/3' SV40 | tobacco (plants) | (+) incorrect transcript polyadenylation | 167 |
| HSV thymidine kinase gene (tk) | 5' HSV/tk/cat | tobacco (tumors) | (−) not expressed | 9 |
| Adenovirus type 5 EIA gene | 5' CaMV35S/EIA/ 3' EIA/3' rbcS | tobacco (plants) | (+) termination within rbcS, EIA polyadenylation site not used | 167 |
| Yeast | | | | |
| Yeast ADH | genomic | tobacco (plants) | (−) not expressed | 21 |
| Plant virus | | | | |
| cDNA encoding TMV coat protein (tobacco mosaic virus) | 5' CaMV35S/TMVcDNA/ 3' nos | tobacco (plants) | + expression confers enhanced resistance to TMV infection | 31, 236, 263 |
| cDNA encoding AMV coat protein (alfalfa mosaic virus) | 5' CaMV 19S/AMVcDNA 5' CaMV 35S/AMVcDNA/ 3' nos | tobacco and tomato (plants) | + expression confers enhanced resistance to AMV infection | 211, 342 |
| cDNAs encoding A- and B-component of TGMV (tomato golden mosaic virus) | separate transformation with either A- or B-component via agroinfection | Petunia (plants) | + only A-components in tandem are able to replicate | 274, 326 |
| cDNA encoding CNV (cucumber mosaic virus) satellite RNA | 5' CaMV 35S/CMVcDNA/ 3' nos | tobacco (plants) | + expression confers enhanced resistance to CMV infection | 23 |
| Plants | | | | |
| Bean phaseolin gene | 5' ocs/phaseolin genomic | sunflower (tumors) | + expressed and processed correctly | 230 |
| | genomic | tobacco (plants) | + development-specific expression in seeds: targeting to protein bodies in endosperm and embryos | 131, 289 |
| | 5' phaseolin/phaseolin-cDNA/3' phaseolin | tobacco (tumors) | + higher expression than using a genomic clone | 49 |
| | 5' phaseolin/maize zein/ 3' phaseolin | tobacco (plants) | + development-specific zein gene expression in tobacco seeds. Zein accumulation | 158 |
| Bean phytohemagglutinin-L gene (PHA-L) | genomic | tobacco (plants) | + development-specific expression in tobacco seeds | 362 |
| Soybean β-conglycinin gene (α subunit) | genomic 5' deletion series | Petunia (plants) | + development-specific expression in Petunia seeds depending on 5' sequences | 25, 51 |
| | 5' CaMV 35S or 19S/ conglycinin/3' nos | Petunia (plants) | + constitutive expression: 35S > 19S; 20 fold clonal variation | 204 |
| Soybean β-conglycinin gene (βsubunit) | genomic | tobacco and Petunia (plants) | + development-specific expression in seeds | 35 |
| Potato patatin gene | 5' patatin/cat/3' nos | potato (plants) | + organ-specific expression in tubers | 343 |
| | 5' ST-LS.1/patatin/3' patatin | tobacco (plants) | + light-regulated and organ-specific expression depending on the ST-LS.1 promoter. Correct splicing of patatin mRNA. | 275 |
| Maize zein gene | genomic | sunflower (tumors) | (+) transcription, but no detectable protein | 126, 217 |
| | 5' phaseolin/zein/3' phaseolin | tobacco (plants) | + development-specific expression in tobacco seeds | 158 |
| Wheat glutenin genes | 5' glutenin/cat/3' nos | tobacco (plants) | + development-specific expression in tobacco seeds | 60 |

TABLE 1-continued

Eukaryptic genes transferred to higher plants

| Origin of gene | Transferred constructs | Transformed species | Mode of foreign gene expression | | References |
|---|---|---|---|---|---|
| Wheat chlorophyll a/b-binding protein (cab) gene | genomic | Petunia and tobacco (plants) | + | light-regulated and organ-specific expression in leaves | 201 |
| | genomic<br>5' cab/cat<br>5' cab/5' CaMV 35S/cat/<br>3' rbcS<br>5' deletion series | tobacco (plants) | + | phytochrome-regulated expression in leaves depending on 5' sequences | 233, 234 |
| Pea cab gene | 5' cab/nptII<br>5' cab/5' nos/nptII | tobacco (plants) | + | light-regulated, organ-and cell-specific expression; depending on enhancer/silencer-like 5' sequences. Involvement of phytochrome. Correlation to the presence of chloroplasts. | 303, 304, 305 |
| Petunia cab gene | 5' cab/ocs<br>5' cab/nos | Petunia and tobacco (plants) | + | clonal variation of expression (200 fold) independent of copy number and homo-/heterologous host genorne | 171, 172 |
| Arabidopsis cab gene | 5' cab/cat | tobacco (plants) | + | light-regulated and organ-specific expression | 10 |
| Pea ribulose 1.5-Bisphosphate carboxylase small subunit gene (rbcS) E9 | genomic<br>5' rbcS/cat<br>5' deletion series | Petunia (tumors) | + | light-regulated expression dependent on 5' sequences | 38, 225 |
| | genomic<br>5' deletion series | Petunia and tobacco (plants) | + | light-regulated and organ-specific expression dependent on 5' sequences: 25-fold clonal variation | 232 |
| Pea rbcS 3.6 | 5' rbcS/cat/3' nos<br>5' deletion series | tobacco (tumors) | + | light-regulated expression dependent on enhancer-like 5' sequences | 152, 338 |
| | 5' rbcS/rbcS transit sequence/ nptII | tobacco (tumors and plants) | + | light-regulated expression and targeting of neomycin phosphotransferase into chloroplasts; analysis of signal sequences | 200, 285, 349, 370 |
| | 5' rbcS/nptII | tobacco (plants) | + | light-regulated, organ- and cell-specific expression. Involvement of a blue-light receptor | 304 |
| Pea rbcS 3A, 3C | genomic | Petunia (plants) | + | regulation of transcription by phytochrome- and/or blue-light receptor depending on the developmental state | 105 |
| Pea rbcS 3A, E9 | 5' rbcS/5' CaMV 35S/cat<br>5' deletion series | Petunia and tobacco (plants) | + | light-regulated and organ-specific expression depending on enhancer- and silencer-like 5' sequences | 106, 198 |
| Soybean rbcS | 5' rbcS/nptII/3' ocs | soybean (tumors) | + | light-regulated expression | 100 |
| | 5' rbcS/nos | Kalanchoe (tumors) | + | light-regulated expression | 295 |
| | 5' rbcS/nptII/3' nos | Petunia (plants) | + | light-regulated expression mediated by phytochrome | 300 |
| Soybean, pea and Petunia rbcS | 5' rbcS/nptII/3' nos | tomato (plants) | + | expression stronger than directed by nos-promoter | 218 |
| *Nicotiana plumbaginifolia* rbeS 8B | 5' rbcS/cat | tobacco and Petunia (plants) | + | light-regulated and organ-specific expression; 3-fold clonal variation independent of homo-/ heterologous host genome | 262, 341 |
| Wheat rbcS | genomic<br>5' CaMV 35 S/rbcS/3' rbcS | tobacco (plants) | (+) | no expression under the control of wheat promoter; CaMV 35S promoter is necessary | 182 |
| Potato ST-LS.1 gene | genomic; modified by exon tagging | potato and tobacco (plants) | + | light-regulated and organ-specific expression depending on the presence of chloroplasts and 5' sequences. Clonal variation parallels copy number, but is independent of homo-/ heterologous host. | 95, 322 |
| | 5' ST-LS.1/patatin/3' patatin | tobacco (plants) | + | light-regulated and organ-specific expression depending on the ST-LS.1 promoter sequences | 275 |
| Petroselinum and Antirrhinum. chalcone synthase genes (chs) | []5' chs(A)/nptII/3' chs(P)<br>5' deletion series | tobacco (plants) | + | UV-B-light-regulated expression dependent on enhancer-like 5' sequences | 180 |

TABLE 1-continued

Eukaryptic genes transferred to higher plants

| Origin of gene | Transferred constructs | Transformed species | Mode of foreign gene expression | | References |
|---|---|---|---|---|---|
| potato proteinase inhibitor II gene (PI II) | genomic<br>5' PI II/cat/3' T-DNA gene 6b<br>5' PI II/cat/3' PI II | tobacco (plants) | + | wound-inducible expression depending on 5' and 3' sequences; systemic spreading by transacting factors | 276, 337 |
| Soybean heat shock gene hs 6871 | genomic<br>5' deletion series | sunflower (tumors) and tobacco (plants) | + | temperature-regulated expression depending on 5' sequences | 24, 284 |
| Soybean heat shock gene Gmhsp 17.E | genomic<br>5' deletion series | sunflower (tumors) | + | expression regulated by temperature and presence of cadmium and arsenite depending on 5' sequences | 139 |
| Maize heat shock gene hsp70 | genomic | Petunia (plants) | + | temperature-regulated expression | 272 |
| Maize alcohol dehydrogenase I gene (AdhI) | 5' CaMV 35S/cat/AdhI intron/3' rbcS | tobacco (plants) | (+) | maize AdhI intron is not removed from the transcript | 182 |
| | 5' AdhI/cat<br>5' ocs/5' AdhI/cat<br>5' CaMV 35S/5' AdhI/cat<br>5' AdhI deletion series | tobacco (plants) and maize (protoplasts) | (+) | anaerobically inducible cat-expression dependent on 5' AdhI sequences only if additional CaMV- or ocs-promoter/enhancer sequences are present. | 97, 99, 164, 366 |
| Maize sucrose synthase gene (SS) | 5' ss/nptII/3' ocs | wheat (protoplasts) | (+) | transient expression | 373 |
| | 5' ss/nptII | maize (protoplasts) | (+) | transient expression suspension-culture derived but not in leaf-derived protoplasts | 177 |
| Soybean β-tubulin gene | genomic | tobacco (plants) | + | | 138 |
| cowpea trypsin inhibitor gene (CpTI) | 5' CaMV 35S/CpTI/3' nos | tobacco (plants) | + | expression enhances resistance to insect pests | 153 |
| Petunia EPSP synthase gene | 5' CaMV 35S/EPSP/3' nos | Petunia (plants) | + | 35S-directed EPSP overproduction confers glyphosate tolerance | 291 |
| | 5' T7-T-DNA/Petunia EPSP transit sequence/bacterial EPSP (aroA) coding region | tobacco (plants) | + | expression of bacterial EPSP; targeting into chloroplasts; glyphosate tolerance | 84 |
| Soybean leghemoglobin gene lbc3 | genomic | tobacco (plants) | | n.d. | 310 |
| | 5' lbc3/cat/3' lbc3 | *Lotus corniculatus* (plants) | + | development-specific and inducible expression only in nodules and only after infection by Rhizobium; dependence on 5' regulatory sequences | 170, 323, 324 |
| *Nicotiana plumbaginifolia* "insert 7" enhancer-like sequence | 5' insert 7/5' nos/nptII | tobacco (plants) | + | transient protoplast-specific overexpression of nptII | 163 |
| *Nicotiana plumbaginifolia* ATP synthase gene (atp2-1); β-subunit | 5' CaMV 35S/atp2-1 signal sequence/cat | tobacco (plants) | + | cat enzyme is targeted into mitochondria | 34 |
| Maize transposable elements Ac and Ds | Ac or Ds within borders of waxy locus | tobacco (tumors and shoots) | + | Ac is capable of self-catalyzed transposition | 15, 16 |

Abbreviations:
copia LTR—long terminal repeat of copia transposable element
HSV—*Herpes simplex* virus
Adh—alcohol dehydrogenase gene
ST-LS 1—*Solarium ruberosum* leaVstem-specific gene
EPSP—5-enolpyruvylshikirnate-3-phosphate (gene)
lbc3—member of the leghemoglobin gene family
Ac, Ds—maize transposable elements (activator, dissociation)
rbcS—ribulose-1,5-bisphosphate carboxylase small subunit gene
cab—chlorophyl a/b binding protein gene
nptII—neomycin phosphotransferase H gene
ocs—octopine synthase gene
nos—nopaline synthase gene
cat—chloramphenicol acetyltransferase gene
CaMV 35S, 19S—cauliflower mosaic virus genes encoding 35S and 19S-transcript, respectively
genomic—transferred construct contains the entire gene including 5 and 3' regions
Mode of expression:
+—correct expression of stably integrated gene
(+)—transient expression, or transcription followed by incorrect processing and/or translation
(−)—gene is not transcribed Of importance in improving food or feed value are genes encoding proteins that contain high levels of essential amino acids. For example, to be nutritionally adequate and support optimal growth of chickens, corn-soybean meal poultry feed is generally supplemented with synthetic methionine or a methionine analog. The development of lines of corn which supply higher levels of methionine can reduce the need for methionine supplements. The development of such high methionine corn lines can be accomplished by introducing into the corn genome a highly expressed gene or genes encoding a high-methionine protein.

Examples of genes encoding high-methionine proteins include: 1.) the gene encoding a maize 15 kD-zein protein (11% methionine), (Pedersen et al., *J. Biol. Chem.,* 261, 6279 (1986)); 2.) the gene encoding a Brazil nut storage protein (18% methionine), (Altenbach et al., *Plant Mol. Biol.,* 8; 239 (1987)) and 3.) the gene encoding a maize 10 kD-zein protein (22.5% methionine), (Kirihara et al., *Gene,* 71, 359 (1988)). The preferred gene is the 10 kD-zein gene, since it is an endogenous maize gene whose protein product normally accumulates in the kernel and is twice as high in methionine than the 15 kD-zein protein. To obtain high levels of expression in the seed, its coding sequence optionally may be fused to the regulatory sequence from a highly-expressed, seed-specific gene. Alternatively, introduction of additional copies of the intact endogenous 10 kD-zein gene into the corn genome can also increase the methionine content of corn seed.

Lysine, an amino acid essential in the diets of humans and monogastric animals, is among the three most limiting amino acids in most of the staple crops, the cereals in particular. Consequently, grain-based diets must be supplemented with synthetic lysine or with lysine-containing oilseed protein meals. Further, since most oilseed meals are themselves inadequate lysine sources, balancing the feed mixture for lysine frequently results in meals which are too high in other, less desirable nutrients. Therefore, a method to increase the lysine content of either the cereal grains or the oilseed crops or both would result in significant added nutritional value, as well as a significant cost savings to end-users such as the swine and poultry producers.

One approach to improving the lysine content of cereals is to deregulate the biosynthetic pathway, allowing free lysine to accumulate. The dap A gene of *Escherichia coli* encodes dihydrodipicolinic acid synthase (DHDPS), a key regulatory enzyme whose activity in plants is strongly feedback-inhibited by lysine. The bacterial enzyme is about 200-fold less sensitive to inhibition by lysine. The introduction and expression of the dap A gene in plant cells would allow the synthesis of free lysine to continue after the native plant DHDPS has been completely inhibited.

Of particular importance in maintaining yield from corn plants and contributing significantly to controlling the cost of growing a corn crop is the protection of the corn against attack by insect pests. In the USA the major insect pests of corn include a variety of Lepidoptera pests such as the European corn borer, cutworms and earworms as well as Coleoptera species such as Diabrotica spp. The protection of corn against insect attack is expensive to the grower and requires the use of toxic chemical insecticides applied in a timely manner. Since traditional methods of breeding and selection have not allowed for the development of new lines of corn that are substantially resistant to major insect pests, the introduction and inheritance of insect resistance genes or sequences in corn plants in accord with the present invention would reduce costs to the grower, reduce the use of toxic chemical insecticides and provide for more effective control of insect pests.

Essential components of the present invention are the introduction of the insect resistance gene into the corn cell, mitotic application of the gene so that the gene is incorporated into whole corn plants and is ultimately inherited by subsequent offspring of the plant via the processes of mitotic and meiotic division.

*Bacillus thuringiensis* (or "Bt") bacteria include nearly 20 known subspecies of bacteria which produce endotoxin polypeptides that are toxic when ingested by a wide variety of insect species. The biology and molecular biology of the endotoxin proteins (Bt proteins) and corresponding genes (Bt genes) has been reviewed recently by H. R. Whitely et al., *Ann. Rev. Microbiol.,* 40, 549 (1986) and by H. Hofte et al., *Microbiol. Rev.,* 53, 242 (1989). Genes coding for a variety of Bt proteins have been cloned and sequenced. Research has demonstrated that a segment of the Bt polypeptide is essential for toxicity to a variety of Lepidoptera pests and is contained within approximately the first 50% of the Bt polypeptide molecule. Consequently, a truncated Bt polypeptide coded by a truncated Bt gene will in many cases retain its toxicity towards a number of Lepidoptera insect pests. The HD73 and HD1 Bt polypeptides have been shown to be toxic to the larvae of the important Lepidoptera insect pests of corn plants in the USA such as the European corn borer, cutworms and earworms. The genes coding for the HD1 and HD73 Bt polypeptides have been cloned and sequenced by M. Geiser et al., Gene, 48, 109 (1986) and M. J. Adang et al., Gene, 36, 289 (1985), respectively, and can be cloned from HD1 and HD73 strains obtained from culture collections (e.g. Bacillus Genetic Stock Center, Columbus, Ohio or USDA Bt stock collection Peoria, Ill.) using standard protocols.

DNA coding for new, previously uncharacterized Bt toxins, may be cloned from the host Bacillus organism using protocols that have previously been used to clone Bt genes. These include the construction of a bank of DNA isolated from the Bacillus organism in a suitable plasmid or phage vector replicated in a suitable host and the use of antibodies, raised against the Bt protein or DNA isolated from a homologous Bt gene sequence, to identify transformants that contain the cloned Bt sequence. The approximate location of the Bt coding sequence may be initially determined using deletion analysis of the cloned DNA. The precise location of the Bt coding sequence could be determined using a variety of standard methods, including the determination of the sequence of the cloned segment of DNA, determining the presence of large open reading frames in this sequence that could code for the Bt protein and confirmation of the Bt coding nature of the DNA sequence by comparing the amino acid sequence derived from the DNA sequence with that derived from partial amino acid sequencing of the Bt protein.

A chimeric Bt gene useful in the present invention would comprise a 5' DNA sequence, comprising a sequence of DNA which will allow for the initiation of transcription ("promoter") and translation of a downstream located Bt sequence in a corn plant. The chimeric Bt gene would also comprise a 3' DNA sequence that includes a sequence derived from the 3' non-coding region of a gene that can be expressed in corn. Most importantly, the chimeric Bt gene will include a DNA sequence coding for a toxic Bt polypeptide produced by *Bacillus thuringiensis* or toxic portions thereof or having substantial amino sequence homology thereto. The Bt coding sequence would include: (i) DNA sequences which code for insecticidally active proteins that have substantial homology to Bt endotoxins that are active against insect pests of corn, e.g., the HD73 or HD1 Bt sequences; (ii) sequences coding for insecticidally active segments of the Bt endotoxin polypeptide, e.g., insecticidally active HD73 or HD1 polypeptides truncated from the carboxy and/or amino termini; (iii) a truncated Bt sequence fused in frame with a sequence(s) that codes for a polypeptide that provides some additional advantage such as: (a)

genes that are selectable, e.g., genes that confer resistance to antibiotics or herbicides, (b) reporter genes whose products are easy to detect or assay, e.g., luciferase or beta-glucuronidase; (c) DNA sequences that code for polypeptide sequences that have some additional use in stabilizing the Bt protein against degradation or enhance the efficacy of the Bt protein against insects, e.g., protease inhibitors and (d) sequences that help direct the Bt protein to a specific compartment inside or outside the corn cell, e.g., a signal sequence.

To obtain optimum synthesis of the Bt protein in corn, it may also be appropriate to adjust the DNA sequence of the Bt gene to more resemble the genes that are efficiently expressed in corn. Since the codon usage of many Bt genes, including the HD73 and HD1 genes, is more similar to that used by Bacillus species and dissimilar to that used by genes that are expressed in maize, the expression of the Bt gene in maize cells can be improved by the replacement of these rarely used Bacillus codons with those that are used more frequently in maize plants (See E. Murray et al., Nucl. Acids Res., 17, 477 (1989)). Such replacement of codons would require the substitution of bases without changing the amino acid sequence of the resulting Bt polypeptide. The Bt polypeptide would be identical in sequence to the bacterial gene or segments thereof. The complete Bt coding sequence, or sections thereof, containing a higher proportion of maize preferred codons than the original bacterial gene could be synthesized using standard chemical synthesis protocols, and introduced or assembled into the Bt gene using standard protocols, such as site-directed mutagenesis or DNA polymerization and ligation and the like.

Aside from recombinant DNA sequences that serve as transcription units or portions thereof, useful recombinant DNA may be untranscribed, serving a regulatory or a structural function. Also, the DNA may be introduced to act as a genetic tool to generate mutants and/or assist in the identification, genetic tagging, or isolation of segments of corn DNA. Additional examples may be found in Weising, cited supra.

The recombinant DNA to be introduced into the plant cells further will generally contain either a selectable marker or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in plants. Useful selectable markers are well known in the art and include, for example, antibiotic and herbicide resistance genes.

Specific examples of selectable marker genes are disclosed in Weising et al., cited supra. A preferred selectable marker gene is the hygromycin phosphotransferase (HPT) coding sequence, which may be derived from *E. coli* and which confers resistance to the antibiotic hygromycin B. Other selectable markers include the aminoglycoside phosphotransferase gene of transposon Tn5 (AphII) which encodes resistance to the antibiotics kanamycin, neomycin and G418, as well as those genes which code for resistance or tolerance to glyphosate, 2,2-dichloropropionic acid, methotrexate, imidazolinone herbicides, sulfonylurea herbicides, bromoxynil, phosphinothricin and other herbicidal compounds. Those selectable marker genes which confer resistance or tolerance to these phytotoxic compounds are also of commercial utility in the resulting transformed plants. Selectable marker genes encoding enzymes which impart resistance to phytotoxic compounds are listed in Table 2, below.

TABLE 2

Selectable Marker Genes

| Resistance Gene or Enzyme | Confers Resistance to: | Reference |
|---|---|---|
| Neomycin phosphotransferase (neo) | G-418, neomycin, kanamycin | P.J. Southern et al Mol. Appl. Gen., 1, 327 (1982) |
| Hygromycin phosphotranferase (hpt or hyg) | Hygromycin B | Y. Shimizu et al., Mol. Cell Biol., 6, 1074 (1986) |
| Dihydrofolate reductase (dhfr) | Methotrexate | W.V. Kwok et al., PNAS USA, 4552 (1986) |
| Phosphinothricin acetyltransferase (bar) | Phosphinothricin | M. DeBlock et al., EMBO J., 2513 (1987) |
| 2.2-Dichloropropionic acid dehalogenase | 2,2-Dichloropropionic acid (Dalapon) | V. Buchanan-Wollaston et al., J. Cell. Biochem Supp. 13D, 330 (1989) |
| Acetohydroxyacid synthase | Sulfonylurea, imidazolinone and triazolopyrimidine herbicides | P.C. Anderson et al. (U.S. Pat. No. 4,761,373); G.W. Haughn et al., Mol. Gen. Genet., 211, 266 (1988) |
| 5-Enolpyruvyl-shikimate-phosphate synthase (aroA) | Glyphosate | L. Comai et al., Nature, 317, 741 (1985) |
| Haloarylnitrilase | Bromoxynil | D.M. Stalker et al., published PCT appln. WO87/04181 |
| Acetyl-coenzyme A carboxylase | Sethoxydim, haloxyfop | W.B. Parker et al., Plant Physiol., 92, 1220 (1990) |
| Dihydropteroate synthase (sul I) | Sulfonamide herbicides | F. Guerineau et al.,- Plant Molec. Biol., 15, 127 (1990) |
| 32 kD photosystem II polypeptide (psbA) | Triazine herbicides | J. Hirschberg et al., Science, 222, 1346 (1983) |
| Anthranilate synthase | 5-Methyltryptophan | K. Hibberd et al., (U.S. Pat. No. 4,581,847) |
| Dihydrodipicolinic acid synthase (dap A) | Aminoethyl cysteine | K. Glassman et al., published PCT application No. WO89/11789 |

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., phenotypic change or enzymatic activity. Examples of such genes are provided in Weising et al., supra. Preferred genes include the chloramphenicol acetyl transferase gene (cat) from Tn9 of E. coli, the beta-glucuronidase gene (gus) of the uida locus of *E. coli*, and the luciferase gene from firefly *Photinus pyralis*. Expression of the reporter gene is assayed at a suitable time after the DNA has been introduced into the recipient cells. A preferred such assay entails the use of the *E. coli* beta-glucuronidase (GUS) gene (R. Jefferson et al., EMBO J., 16, 3901 (1987)). Maize cells transformed and expressing this gene will stain blue upon exposure to the substrate, 5-bromo-4-chloro-3-indolyl-beta-D-glucuronide (X-GLUC), in the extracellular medium.

The regulatory sequences useful herein include any constitutive, inducible, tissue or organ specific, or developmental stage specific promoter which can be expressed in the particular plant cell. Suitable such promoters are disclosed in Weising et al., supra. The following is a partial representative list of promoters suitable for use herein: regulatory sequences from the T-DNA of Aarobacterium tumefaciens, including mannopine synthase, nopaline synthase, and octopine synthase; alcohol dehydrogenase promoter from corn; light-inducible promoters such as the ribulose-bisphosphate-carboxylase/oxygenase small subunit genes from a variety of species; and the major chlorophyll a/b binding protein gene promoters; 35S and 19S promoters of cauliflower mosaic virus (CaMV); developmentally regulated promoters such as the waxy, zein, or bronze promoters from maize; as well as synthetic or other natural promoters which are either inducible or constitutive, including those promoters exhibiting organ-specific expression or expression at specific development stage(s) of the plant.

Other elements such as introns, enhancers, polyadenylation sequences and the like, may also be a part of the recombinant DNA. Such elements may or may not be necessary for the function of the DNA, but may provide improved expression of the DNA by affecting transcription, stability of the MRNA, or the like. Such elements may be included in the DNA as desired to obtain the optimal performance of the transforming DNA in the plant. For example, the maize AdhIS first intron may be placed between the promoter and the coding sequence in a particular recombinant DNA construction. This intron, when included in a DNA construction, is known to increase production of a protein in maize cells. (J. Callis et al., *Genes and Develop.,* 1, 1183 (1987)). However, sufficient expression for a selectable marker to perform satisfactorily can often be obtained without an intron. (T. Klein et al., *Plant Physiol.,* 91, 440 (1989)). An example of an alternative suitable intron is the shrunken-1 first intron of *Zea mays*. These other elements must be compatible with the remainder of the DNA constructions.

III. DNA Delivery Process

The recombinant DNA can be introduced into the regenerable maize cell cultures, preferably into callus cultures via a particle bombardment process. A general description of a suitable particle bombardment instrument is provided in Sanford et al. (1987), the disclosure of which is incorporated herein by reference. While protocols for the use of the instrument in the bombardment of maize non-regenerable suspension culture cells are described in Klein et al. (1988a, 1988b, and 1989), no protocols have been published for the bombardment of callus cultures or regenerable maize cells.

In a microprojectile bombardment process, also referred to as a biolistic process, the transport of the recombinant DNA into the callus is mediated by very small particles of a biologically inert material. When the inert particles are coated with DNA and accelerated to a suitable velocity, one or more of the particles is able to enter into one or more of the cells where the DNA is released from the particle and expressed within the cell. Some of the recipient cells stably retain the introduced DNA and express it.

The particles, called microprojectiles, are generally of a high density material such as tungsten or gold. They are coated with the DNA of interest. The microprojectiles are then placed onto the surface of a macroprojectile which serves to transfer the motive force from a suitable energy source to the microprojectiles. After the macroprojectile and the microprojectiles are accelerated to the proper velocity, they contact a blocking device which prevents the macroprojectile from continuing its forward path but allows the DNA-coated microprojectiles to continue on and impact the recipient callus cells. Suitable such instruments may use a variety of motive forces such as gunpowder or shock waves from an electric arc discharge (P. Christou et al., Plant Physiol., 87, 671 (1988)). An instrument in which gunpowder is the motive force is currently preferred and such is described and further explained in Sanford et al. (1987), the disclosure of which is incorporated herein by reference.

A protocol for the use of the gunpowder instrument is provided in Klein et al. (1988a,b) and involves two major steps. First, tungsten microprojectiles are mixed with the DNA, calcium chloride, and spermidine in a specified order in an aqueous solution. The concentrations of the various components may be varied as taught. The preferred procedure entails exactly the procedure of Klein et al. (1988b) except for doubling the stated optimum DNA concentration. Secondly, the DNA-coated microprojectiles, macroprojectiles, and recipient cells are placed in position in the instrument and the motive force is applied to the macroprojectiles. Parts of this step which may be varied include the distance of the recipient cells from the end of the barrel as well as the vacuum level in the sample chamber. The recipient tissue is positioned 2–15, preferably 5 cm below the stopping plate tray.

The callus cultures useful herein for generation of transgenic plants should generally be about midway between transfer periods, and thus, past any "lag" phase that might be associated with a transfer to a new media, but also before reaching any "stationary" phase associated with an extended period of time without subculture to fresh media. The tissue may be used in the form of pieces of about 30 to 80, preferably about 40 to 60, mg. The clumps can be placed on a petri dish or other surface and arranged in essentially any manner, recognizing that (i) the space in the center of the dish will receive the heaviest concentration of metal-DNA particles and the tissue located there is likely to suffer damage during bombardment and, (ii) the number of particles reaching the tissue will decrease with increasing distance of the tissue from the center of the blast so that the tissue far from the center of the dish is less likely to be bombarded. A mesh screen, preferably of metal, may be laid on the dish to prevent splashing or ejection of the tissue. An alternative method for presentation of the tissue for bombardment is to spread the tissue onto a filter paper in a thin layer. The tissue may be bombarded one or more times with the DNA-coated metal particles.

IV. Selection Process

Once the calli have been bombarded with the recombinant DNA and the DNA has penetrated some of the cells, it is necessary to identify and select those cells which both contain the recombinant DNA and still retain sufficient regenerative capacity. There are two general approaches which have been found useful for accomplishing this. First, the transformed calli or plants regenerated therefrom can be screened for the presence of the recombinant DNA by various standard methods which could include assays for the expression of reporter genes or assessment of phenotypic effects of the recombinant DNA, if any. Alternatively, and preferably, when a selectable marker gene has been transmitted along with or as part of the recombinant DNA, those cells of the callus which have been transformed can be identified by the use of a selective agent to detect expression of the selectable marker gene.

Selection of the putative transformants is a critical part of the successful transformation process since selection conditions must be chosen so as to allow growth and accumulation of the transformed cells while simultaneously inhibiting the growth of the non-transformed cells. The situation is complicated by the fact that the vitality of individual cells in a population is often highly dependent on the vitality of neighboring cells. Also, the selection conditions must not be so severe that the plant regeneration capacity of the callus cells and the fertility of the resulting plant are precluded. Thus, the effects of the selection agent on cell viability and morphology should be evaluated. This may be accomplished by experimentally producing a growth inhibition curve for the given selective agent and tissue being transformed before-hand. This will establish the concentration range which will inhibit growth.

When a selectable marker gene has been used, the callus clumps may be either allowed to recover from the bombardment on non-selective media, or preferably, directly transferred to media containing the selection agent.

Selection procedures involve exposure to a toxic agent and may employ sequential changes in the concentration of the agent and multiple rounds of selection. The particular concentrations and cycle lengths are likely to need to be varied for each particular agent. A currently preferred selection procedure entails using an initial selection round at a relatively low toxic agent concentration and then later round(s) at higher concentration(s). This allows the selective agent to exert its toxic effect slowly over a longer period of time. Preferably, the concentration of the agent is initially such that about a 5–40% level of growth inhibition will occur, as determined from a growth inhibition curve. The effect may be to allow the transformed cells to preferentially grow and divide while inhibiting untransformed cells, but not to the extent that growth of the untransformed cells is prevented. Once the few individual transformed cells have divided a sufficient number of times, the tissue may be shifted to media containing a higher concentration of the toxic agent to kill essentially all untransformed cells. The shift to the higher concentration also reduces the possibility of nontransformed cells adapting to the agent. The higher level is preferably in the range of about 30 to 100% growth inhibition. The length of the first selection cycle may be from about 1 to 4 weeks, preferably about 2 weeks. Later selection cycles may be from about 1 to 12 weeks, preferably about 2 to 10 weeks. Putative maize transformants can generally be identified as proliferating sectors of tissue among a background of non-proliferating cells. The callus may also be cultured on non-selective media at various times during the overall selection procedure.

Once a callus sector is identified as a putative transformant, transformation can be confirmed by phenotypic and/or genotypic analysis. If a selection agent is used, an example of phenotypic analysis is to measure the increase in fresh weight of the putative transformant as compared to a control on various levels of the selective agent. Other analyses that may be employed will depend on the function of the recombinant DNA. For example, if an enzyme or protein is encoded by the DNA, enzymatic or immunological assays specific for the particular enzyme or protein may be used. Other gene products may be assayed by using a suitable bioassay or chemical assay. Other such techniques are well known in the art and are not repeated here. The presence of the gene can also be confirmed by conventional procedures, i.e., Southern blot or polymerase chain reaction (PCR) or the like.

V. Reqeneration of Plants and Production of Seed

Cell lines which have been shown to be transformed must then be regenerated into plants and the fertility of the resultant plants determined. Transformed lines which test positive by genotypic and/or phenotypic analysis are then placed on a medium which promotes tissue differentiation and plant regeneration. Regeneration may be carried out in accordance with standard procedures well known in the art. The procedures commonly entail reducing the level of auxin which discontinues proliferation of a callus and promotes somatic embryo development or other tissue differentiation. One example of such a regeneration procedure is described in Green et al. (1982). The plants are grown to maturity in a growth room or greenhouse and appropriate sexual crosses are made as described by Neuffer (1982).

Regeneration, while important to the present invention, may be performed in any conventional manner. If a selectable marker has been transformed into the cells, the selection agent may be incorporated into the regeneration media to further confirm that the regenerated plantlets are transformed. Since regeneration techniques are well known and not critical to the present invention, any technique which accomplishes the regeneration and produces fertile plants may be used.

VI. Analysis of R1 Progeny

The plants regenerated from the transformed callus are referred to as the R0 generation or R0 plants. The seeds produced by various sexual crosses of the R0 generation plants are referred to as R1 progeny or the R1 generation. When R1 seeds are germinated, the resulting plants are also referred to as the R1 generation.

To confirm the successful transmission and inheritance of the recombinant DNA through one complete sexual cycle, the R1 generation should be analyzed to confirm the presence of the transforming DNA. The analysis may be performed in any of the manners such as were disclosed above for analyzing the bombarded callus for evidence of transformation, taking into account the fact that plants and plant parts are being used in place of the callus.

The recombinant DNA can show different types of inheritance patterns for different transformed lines. For example, the recombinant DNA may be inherited in the progeny according to the rules of Mendelian inheritance. This type of heritability involves transmission of the DNA through both the male and female gametes and is associated with stable integration or incorporation into maize nuclear DNA. An alternative type of inheritance pattern is maternal inheritance, in which the recombinant DNA is transmitted primarily or exclusively through the female gametes. The inheritance pattern for a particular transformant may be ascertained by analysis of the progeny of various sexual crosses.

VII. Establishment of the Recombinant DNA in Other Maize Varieties

Fertile, transgenic plants may then be used in a conventional maize breeding program in order to incorporate the introduced recombinant DNA into the desired lines or varieties. Methods and references for convergent improvement of corn are given by Hallauer et al., (1988) incorporated herein by reference. Among the approaches that conventional breeding programs employ is a conversion process (backcrossing). Briefly, conversion is performed by crossing the initial transgenic fertile plant to elite inbred lines. The progeny from this cross will segregate such that some of the plants will carry the recombinant DNA whereas some will not. The plants that do carry the DNA are then crossed again to the elite inbred lines resulting in progeny which segregate once more. This backcrossing process is repeated until the original elite inbred has been converted to a line containing the recombinant DNA, yet possessing all important attributes originally found in the parent. Generally, this will require about 6–8 generations. A separate backcrossing program will be generally used for every elite line that is to be converted to a genetically engineered elite line.

Generally, the commercial value of the transformed corn produced herein will be greatest if the recombinant DNA can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, and insect resistance. As such, it is necessary to incorporate the recombinant DNA into a large number of parental lines so that many hybrid combinations can be produced containing the desirable heterologous DNA.

Corn breeding and the techniques and skills required to transfer genes from one line or variety to another are well known to those skilled in the art. Thus, introducing recombinant DNA into any other line or variety can be accomplished by these breeding procedures.

VIII. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents (e.g., oils or starches) of corn and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from corn cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

The following non-limiting examples are illustrative of the present invention. They are presented to better explain the general procedures which were used to prepare the fertile *Zea mays* plants of this invention which stably express the recombinant DNA and which transmit that DNA to progeny. All parts and percentages are by weight unless otherwise specified. It must be recognized that the probability of a specific transformation event occurring is a function of the amount of material subjected to the transformation procedure. Thus, when individual situations arise in which the procedures described herein do not produce a transformed product, repetition of the procedures will be required.

EXAMPLE I

Fertile Transgenic *Zea Mays* Plants

I. Initiation and maintenance of maize cell cultures which retain plant regeneration capacity Friable, embryogenic maize callus cultures were initiated from hybrid immature embryos produced by pollination of inbred line A188 plants (University of Minnesota, Crop Improvement Association) with pollen of inbred line B73 plants (Iowa State University). Ears were harvested when the embryos had reached a length of 1.5 to 2.0 mm. Each ear was surface sterilized in 50% v/v commercial bleach (2.63% w/v sodium hypochlorite) for 20 min. at room temperature. The ears were then washed with sterile, distilled, deionized water. Immature embryos were aseptically isolated and placed on nutrient initiation/maintenance medium with the root/shoot axis exposed to the medium. Initiation/maintenance medium (hereinafter referred to as "F medium") consisted of N6 basal media (Chu 1975) with 2% (w/v) sucrose, 1.5 mg per liter 2,4-dichlorophenoxyacetic acid (2,4-D), 6 mM proline, and 0.25% Gelrite (Kelco, Inc., San Diego). The pH was adjusted to 5.8 prior to autoclaving. Unless otherwise stated, all tissue culture manipulations were carried out under sterile conditions.

The immature embryos were incubated at 260C in the dark. Cell proliferations from the scutellum of the immature embryos were evaluated for friable consistency and the presence of well-defined somatic embryos. Tissue with this morphology was transferred to fresh media 10 to 14 days after the initial plating of the immature embryos. The tissue was then subcultured on a routine basis every 14 to 21 days. Sixty to eighty milligram quantities of tissue were removed from pieces of tissue that had reached a size of approximately one gram and were transferred to fresh media. Subculturing always involved careful visual monitoring to be sure that only tissue of the correct morphology was maintained. The presence of somatic embryos ensured that the cultures would give rise to plants under & the proper conditions. The cell culture named AB12 used in this example was such a culture and had been initiated about 1 year before bombardment.

II. Plasmids

Figure 2:
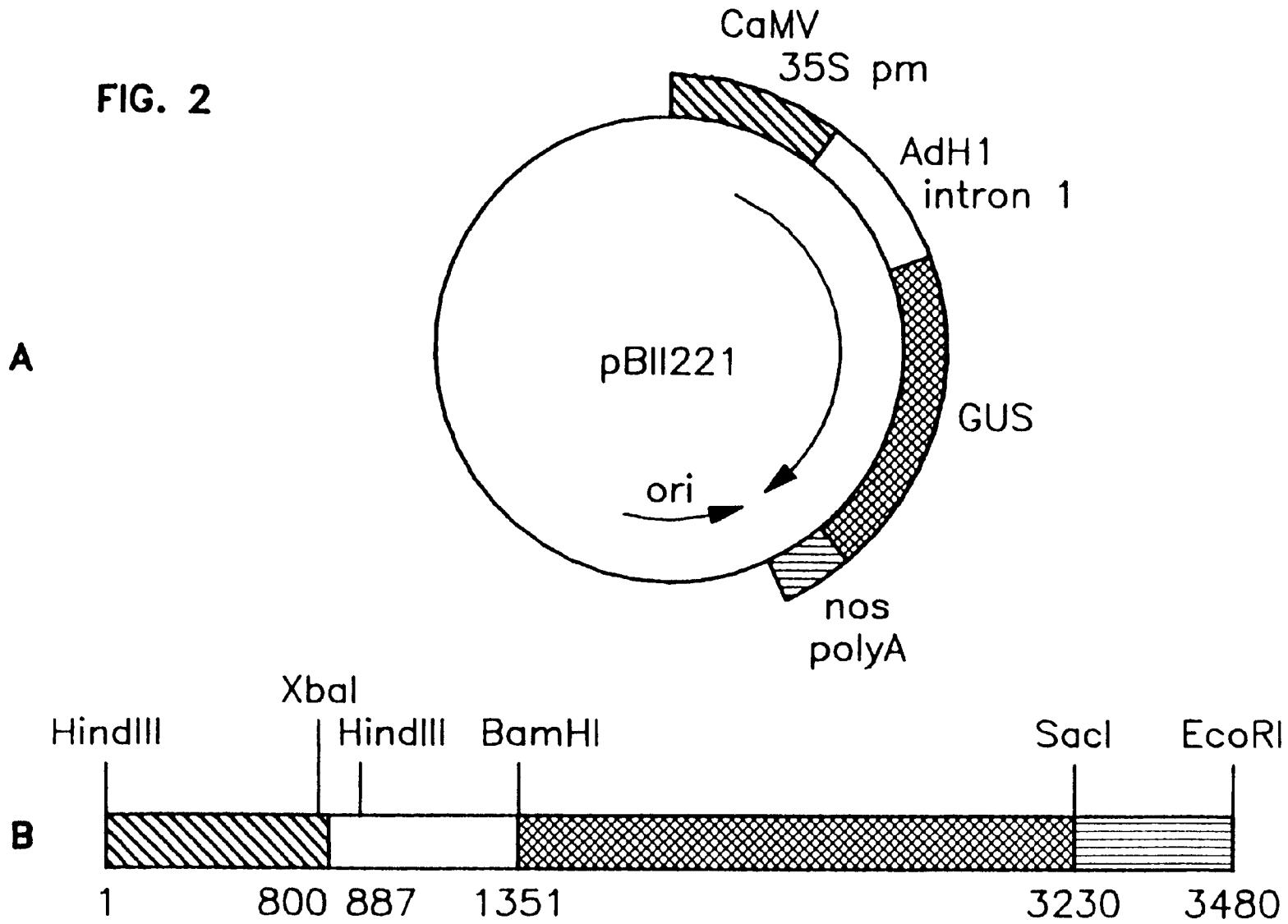
FIG. 2A shows a map of plasmid vector pBII221 utilized in EXAMPLE I.
FIG. 2B depicts linearized pBII221, e.g., from the HindIII cleavage site to the EcoRI cleavage site.

The plasmid pHYGI1, was constructed in the vector pBS+ (Stratagene, Inc., San Diego, Calif.), a 3.2 Kb circular plasmid, using standard recombinant DNA techniques. The 553 bp Bcl-BamHI fragment containing the maize AdhIS first intron (Callis et al. 1987) was inserted between the CaMV 35S promoter and the hygromycin coding sequence of pCHN1-1, a plasmid constructed in accord with Example V. A map of pHYGI1 is provided as FIG. 1. A sample of pHYGI1 was deposited at the American Type Culture Collection, Rockville, Md., USA, on Mar. 16, 1990, under the provisions of the Budapest Treaty, and assigned accession number 40774.

pBII221 contains the *E. coli* P-glucuronidase coding sequence flanked at the 5' end by the CAMV 35S promoter and at the 3' end by the nos polyadenylation sequence. The plasmid was constructed by inserting the maize AdhIS first intron between the 35S promoter and the coding sequence of pBI221 (Jefferson et al. 1987). A map of pBII221 is provided as FIG. 2.

Plasmids were introduced into the embryogenic callus culture AB12 by microprojectile bombardment.

III. DNA delivery process

The embryogenic maize callus line AB12 was subcultured 7 to 12 days prior to microprojectile bombardment. AB12 callus was prepared for bombardment as follows. Five clumps of callus, each approximately 50 mg in wet weight were arranged in a cross pattern in the center of a sterile 60×15 mm petri plate (Falcon 1007). Plates were stored in a closed container with moist paper towels, throughout the bombardment process. Twelve plates were prepared.

Plasmids were coated onto M-10 tungsten particles (Biolistics) exactly as described by Klein et al. (1988b) except that, (i) twice the recommended quantity of DNA was used, (ii) the DNA precipitation onto the particles was performed at 0° C, and (iii) the tubes containing the DNA-coated tungsten particles were stored on ice throughout the bombardment process.

All of the tubes contained 25 $\mu$l of 50 mg/ml M-10 tungsten in water, 25 $\mu$l of 2.5 M $CaCl_2$, and 10 $\mu$l of 100 mM spermidine along with a total of 5 $\mu$l of 1 mg/ml plasmid DNA. When both plasmids were used, each was present in an amount of 2.5 $\mu$l. One tube contained only plasmid pBII221; and one tube contained T.E. buffer (see Table 2, below).

All tubes were incubated on ice for 10 min., the particles were pelleted by centrifugation in an Eppendorf centrifuge at room temperature for 5 seconds, 25 $\mu$l of the supernatant was discarded. The tubes were stored on ice throughout the bombardment process. Each preparation was used for no more than 5 bombardments.

Macroprojectiles and stopping plates were obtained from Biolistics, Inc. (Ithaca, N.Y.). They were sterilized as described by the supplier. The microprojectile bombardment instrument was obtained from Biolistics, Inc.

The sample plate tray was placed 5 cm below the bottom of the stopping plate tray of the microprojectile instrument, with the stopping plate in the slot nearest to the barrel. Plates of callus tissue prepared as described above were centered on the sample plate tray and the petri dish lid removed. A 7×7 cm square rigid wire mesh with 3×3 mm mesh and made of galvanized steel was placed over the open dish in order to retain the tissue during the bombardment. Tungsten/DNA preparations were sonicated as described by Biolistics, Inc. and 2.5 $\mu$l of the suspensions were pipetted onto the top of the macroprojectiles for each bombardment. The instrument was operated as described by the manufacturer. The bombardments which were performed are summarized on Table 3.

TABLE 3

| | |
|---|---|
| 2 × PBII221 prep | To determine transient expression frequency |
| 7 × pHYGI1/pBII221 (1:1) | As a potential positive treatment for transformation |
| 3 × T.E.[a] | Negative control treatment |

[a]10 mM Tris.HCL, pH 8.0, 1 mM EDTA

The two plates of callus bombarded with pBII221 were transferred plate for plate to F medium (with no hygromycin) and the callus cultured at 26° C. in the dark. After 2 days, this callus was then transferred plate for plate into 35×10 mm petri plates (Falcon 1008) containing 2 ml of GUS assay buffer (1 mg/ml of 5-bromo-4-chloro-3-indolyl-beta-D-glucuronide) (Research Organics), 100 mM sodium phosphate pH 7.0, 5 mM each of potassium ferricyanide and potassium ferrocyanide, 10 mM EDTA, and 0.06% Triton X-100. The plates were incubated at 37° C. for 3 days after which the number of blue cells was counted giving a total of 313 and 355 transient GUS-expressing cells visible in the two plates, suggesting that the DNA delivery process had also occurred with the other bombarded plates. The plates of tissue used in the GUS assay were discarded after counting since the GUS assay is destructive.

IV. Selection process

Hygromycin B (Calbiochem) was incorporated into the medium prior to pouring plates by addition of the appropriate volume of filter-sterilized 100 mg/ml hygromycin B dissolved in water, when the medium had cooled to 45° C.

Immediately after all samples had been bombarded, callus from all of the plates treated with pHYGI1/pBII221, and two of the T.E. plates was transferred plate for plate onto F medium containing 15 mg/l hygromycin B, (ten pieces of callus per plate). These are referred to as round 1 selection plates. Callus from the T.E. treated plate was transferred to F medium without hygromycin. This tissue was subcultured every 2–3 weeks onto nonselective medium and is referred to as unselected control callus.

After 14 days of selection, tissue appeared essentially identical on both selective and nonselective media. All callus from seven plates of the pHYGI1/pBII221 and one T.E. treated plate were transferred from round 1 selection plates to round 2 selection plates that contained 60 mg/l hygromycin. The round 2 selection plates each contained ten 30 mg pieces of callus per plate, resulting in an expansion of the total number of plates.

After 21 days on the round 2 selection plates, all of the material was transferred to round 3 selection plates containing 60 mg/l hygromycin. After 79 days post-bombardment, the round 3 sets of selection plates were checked for viable sectors of callus. One of the sectors was proliferating from a background of necrotic tissue on plates treated with pHYGI1/pBII221. The sector was designated PH3 and was transferred to F medium without hygromycin.

After 19 days on F medium without hygromycin, PH3 was transferred to F-medium containing 60 mg/l hygromycin. PH3 was found to be capable of sustained growth through multiple subcultures in the presence of 60 mg/l hygromycin.

V. Confirmation of transformed callus

To show that the PH3 callus had acquired the hygromycin resistance gene, genomic DNA was isolated from PH3 callus and unselected control callus in accord with Example V, and analyzed by Southern blotting. The isolated DNA (10 $\mu$g) was digested with BamHI (NEB) and electrophoresed in a 0.8% w/v agarose gel at 15 V for 16 hrs in TAE buffer (40 mM Tris-acetate, pH 7.6, 1 mM EDTA). The DNA was transferred to a Nytran membrane (Schleicher and Schuell). Transfer, hybridization and washing conditions were carried out as per the manufacturer's recommendations.

A $^{32}$p labelled probe was prepared by random primer labelling with an Oligo Labelling Kit (Pharmacia) as per the supplier's Instructions with a-$^{32}$P-dCTP (ICN Radiochemicals). The template DNA used was the 1055 bp BamHI fragment of pHYGI1, which contains the entire HPT coding sequence.

Membranes were exposed to Kodak X-OMAT AR film in an X-OMATIC cassette with intensifying screens. A band was observed for PH3 callus at the expected position of 1.05 Kb, indicating that the HPT coding sequence was present. No band was observed for control callus.

To demonstrate that the hygromycin gene is incorporated into high molecular weight DNA, undigested DNA from PH3 callus and control callus was electrophoresed, blotted and hybridized as described above. Undigested PH3 DNA only showed hybridization to the probe at a mobility equal to uncut DNA. No hybridization was observed for DNA from control callus. These results demonstrate that the HPT coding sequence is not present in PH3 callus as intact pHYGI1 or as a small non-chromosomal plasmid. The results are consistent with incorporation of the hygromycin gene into high molecular weight DNA.

VI. Plant regeneration and production of seed

Portions of PH3 callus were transferred directly from plates containing 60 mg/l hygromycin to RM5 medium which consists of MS basal salts (Murashige et al. 1962) supplemented with thiamine.HCl 0.5 mg/l, 2,4-D 0.75 mg/l, sucrose 50 g/l, asparagine 150 mg/l, and Gelrite 2.5 g/l (Kelco Inc., San Diego).

After 14 days on RM5 medium, the majority of PH3 and unselected control callus was transferred to R5 medium (RM5 medium, except that 2,4-D is omitted). The plates were cultured in the dark for 7 days at 26° C. and transferred to a light regime of 14 hrs light and 10 hrs dark for 14 days at 26° C. At this point, plantlets that had formed were transferred to one quart canning jars (Ball) containing 100 ml of R5 medium. Plants were transferred from jars to vermiculite for 7 or 8 days before transplanting them into soil and growing them to maturity. A total of 45 plants were produced from PH3 and a total of 10 plants were produced from control callus.

Controlled pollinations of mature PH3 plants were conducted by standard techniques with inbred *Zea mays* lines MBS501 (Mike Brayton Seeds), FR4326 (Illinois Foundation Research) and the proprietary inbred line LM1112. Seed was harvested 45 days post-pollination and allowed to dry further for 1–2 weeks.

VII. Analysis of the R1 progeny

R1 plants were tested for the presence of the HPT and GUS gene sequences by PCR analysis. Expression of the HPT gene was determined with an enzymatic assay for HPT activity. Table 4 summarizes the data. These data demonstrate transmission and expression of the recombinant DNA through both male and female parents, and are consistent with Mendelian inheritance. The Southern blot evidence for integration of the HPT coding sequence into high molecular weight DNA for the source callus, combined with the inheritance data, suggest that the foregoing DNA sequences are chromosomally integrated. The presence of GUS gene sequences in the R1 progeny demonstrates cotransformation and inheritance of an unselected gene.

TABLE 4

Analysis of R1 Progeny of PH3 Transformants

| | Enzyme | PCR Assay | |
|---|---|---|---|
| PH3.4 Plant | HPT Assay | HPT | GUS |
| | Parents: MBS501 × PH3.4 | | |
| 4.1 | – | – | – |
| 4.2 | + | + | + |
| 4.3 | + | + | + |
| 4.4 | – | – | – |
| 4.5 | + | + | + |
| 4.6 | + | + | + |
| 4.7 | + | + | + |
| 4.8 | – | – | – |
| 4.9 | – | – | – |
| | Parents: LM1112 × PH3.18 | | |
| 18.1 | – | – | – |
| 18.2 | + | + | + |
| 18.3 | – | – | – |
| 18.4 | – | – | – |
| 18.5 | + | + | + |
| 18.6 | + | + | + |
| 18.7 | + | + | + |
| 18.8 | + | + | + |
| 18.9 | + | + | + |
| 18.10 | + | + | + |
| | Parents: PH3.2 × FR4326 | | |
| 2.1 | – | – | – |
| 2.2 | – | – | – |
| 2.3 | + | + | + |
| 2.4 | – | – | – |
| 2.5 | + | + | + |
| 2.6 | – | – | – |
| 2.7 | + | + | + |
| 2.8 | + | + | ND |
| 2.9 | + | + | ND |
| | Controls | | |
| | Parents: TE3.1 × Oh43 | | |
| 3.1 | – | – | ND |
| 3.2 | – | – | ND |
| 3.3 | – | – | ND |
| 3.4 | – | – | ND |
| 3.5 | – | – | ND |
| 3.6 | – | – | ND |
| 3.7 | – | – | – |
| 3.8 | – | – | – |
| 3.9 | – | – | – |
| 3.10 | – | – | – |
| 3.11 | – | ND | ND |
| 3.12 | – | ND | ND |
| 3.13 | – | ND | ND |
| 3.14 | – | ND | ND |
| 3.15 | – | ND | ND |
| 3.16 | – | ND | ND |
| 3.17 | – | ND | ND |
| 3.18 | – | ND | ND |
| 3.19 | – | ND | ND |
| 3.20 | – | ND | ND |
| 3.21 | – | ND | ND |
| 3.22 | – | ND | ND |
| 3.23 | – | ND | ND |
| 3.24 | – | ND | ND |

The HPT enzyme assay was based on the following methods: S. K. Datta et al., *Bio/Technology,* 8, 736 (1990), M. Staebell et al., *Anal. Biochem.,* 185, 319 (1990), and E. Cabanes-Bastos, *Gene,* 77, 169 (1989).

Root samples (0.2 g) were excised from 7–10 day old seedlings and were quick frozen in liquid nitrogen ($N_2$). Samples were ground with alumina and 400 $\mu$l of EB (50 mM Tris-HCl, 10% v/v glycerol, 0.1 mM PMSF, pH 7.0) for 30–60 seconds using a disposable pestle and tube (Kontes), then centrifuged in an Eppendorf microfuge for 10 min. The supernatant was transferred to a Centricon 30 filter unit and desalted by centrifuging in a fixed angle rotor at 5000 rpm in a Beckman GPR centrifuge for 30 min at 4° C. One ml of EB was used to wash each filter unit, spinning an additional 5000 RPM for 60 min. The retentate was then recovered and stored at −70° C. Samples of transgenic and unselected control callus tissue (0.2 g) were ground as described above, and the supernatents were used as positive and negative controls.

Protein was quantified using the method of Bradford, *Anal. Biochem.,* 72, 248 (1976) with a BioRad kit. Protein concentrations in root extracts ranged from 0.2–2 μg/μl.

The root extract (4 pg total protein) was added to a reaction mixture containing 20 mM Tris-maleate, 13 mM $MgCl_2$, 120 mM $NH_4Cl$, 0.5 mM DTT, 50 μM ATP, 0.61 μg/μl hygromycin B, 25 pg/pl bovine serum albumin, and 12 μCi gamma 32P-ATP. Reaction volume was 33 μl. The reaction mixture was incubated for 30 min at 37° C.

One μl of the reaction mixture was spotted on a polyethyleneimine cellulose thin layer chromatography plate (Sigma Chem. Co.). Plates were developed in 50 mM formic acid pH 5.4, air dried, and exposed to Kodak XAR-5 film. The reaction product, hygromycin phosphate, migrates near the solvent front under these conditions.

To conduct the PCR assay, 0.1 g samples were taken from plant tissues and frozen in liquid nitrogen. Samples were then ground with 120 grit carborundum in 200μl 0.1M Tris-HCl, O.1M NaCl, 20 mM EDTA, 1% Sarkosyl pH 8.5) at 4° C. Following phenol/chloroform extraction and ethanol and isopropanol precipitations, samples were suspended in T.E. and analyzed by polymerase chain reaction (K. B. Mullis, U.S. Pat. No. 4,683,202).

PCR was carried out in 100 μl volumes in 50 mM KCl, 10 mM Tris-HCl pH 8.4, 3 mM $MgCl_2$, 100 μg/ml gelatin, 0.25 μM each of the appropriate primers, 0.2 mM of each deoxynucleoside triphosphate (DATP, dCTP, dGTP, dTTP), 2.5 Units of Taq DNA polymerase (Cetus), and 10 μl of the DNA preparation. The mixture was overlaid with mineral oil, heated to 94° C. for 3 min, and amplified for 35 cycles of 55° C. for 1 min, 72° C. for 1 min, 94° C. for 1 min. The mixture was then incubated at 50° C. for 2 min and 72° C. for 5 min. 10 μl of the PCR product was electrophoresed in agarose gels and visualized by staining with ethidium bromide.

For analysis of the presence of the HPT gene, a PCR primer complementary to the 35S promoter, and one complementary to the HPT coding sequence were employed. Thus, in order to generate the appropriately sized PCR product, the HPT template DNA must contain contiguous 35S promoter region, Adh1 intron, and 5' protein coding sequence region.

For analysis of the presence of the GUS gene, PCR primers complementary to sequences within the GUS protein coding region were employed. A 797 bp PCR product is predicted if the template DNA contains an intact coding region between the two primers.

EXAMPLE II

Fertile Transgenic Plants from Callus Line AB63S Containing Recombinant DNA Encoding a Seed Storage Protein The 10 kD-zein storage protein is produced in the endosperm of the maize kernel and is a representative member of a class of proteins referred to as "seed storage proteins." The protein contains extremely high levels of methionine (22.5%) and is encoded by the Zps10/(22) gene (M. S. Benner et al., *Theor. Appl. Genet.,* 78, 761 (1989)); a gene referred to as z10 herein. Thus, increased expression of the z10 gene can be used to increase the methionine content of corn. Production of fertile transgenic corn containing a chimeric z10 gene was accomplished by the procedures of Example I with some minor modifications. Example II also demonstrates the introduction of recombinant DNA using a callus line different from that used in Example I.

I. Tissue Culture Lines

The embryogenic maize callus line named AB63S used in this example was produced from immature embryos resulting from a cross between elite inbred lines A188 and B73, by the initiation and maintenance procedures described in Example I. The callus line had been initiated approximately 7 months prior to bombardment. Eleven weeks prior to bombardment the tissue was sieved by forcing it through a 1.9 mm screen and plated onto N6 maintenance medium.

Friable, embryogenic callus was selected from the resulting tissue after 1–2 weeks of growth, transferred to fresh medium and allowed to grow for 1.5–3 weeks before sieving again. This cycle of sieving and recovery of friable callus was carried out a total of three times prior to subjecting the tissue to bombardment.

II. Plasmids

Figure 7:
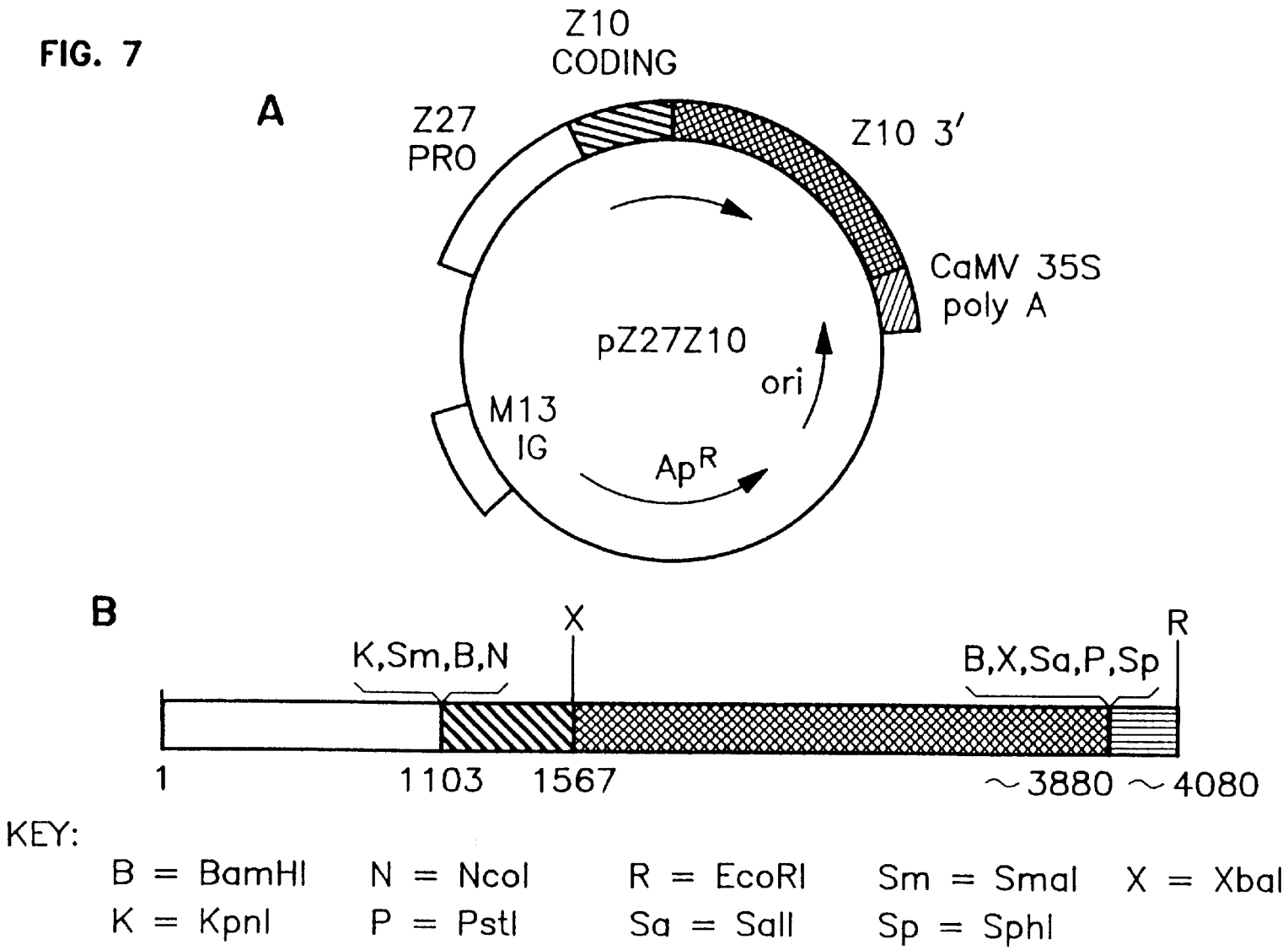
FIG. 7A shows a map of plasmid vector pZ27Z10 utilized in EXAMPLE II.
FIG. 7B depicts linearized plasmid pZ27Z10 encompassing the z10 coding sequence and associated regulatory elements.

The plasmids pHYGI1 and pBII221 described in Example I were used in this Example. In addition, the plasmid pZ27Z10 was included in the DNA/tungsten preparations. The plasmid pZ27Z10 was constructed using the vector pUC118 (J. Vieira et al., Methods Enzymol., 153, 3 (1987), a 3.2 kb circular plasmid, by standard recombinant DNA techniques. pZ27Z10 contains the 5' transcriptional regulatory region from a maize 27 kD-zein gene (D. E. Geraghty, Ph.D. Thesis, University of Minnesota (1987)), referred to as z27 in this document), positioned immediately adjacent to the coding sequence and 3' noncoding sequence from a maize 10 kD-zein gene (Kirihara et al., Gene, 7, 359 (1988)), referred to as z10 in this document). The combination of the z27 regulatory sequence and z10 coding and 3' sequences is referred to as the chimeric z27-z10 gene in this document. The poly A signal from the region of the CaMV genome adjacent to the 35S promoter is positioned 3' to the z10 gene sequences in pZ27Z10. FIG. 7 depicts a map of this plasmid.

A sample of plasmid pZ27Z10 has been deposited in the American Type Culture Collection, Rockville, Md., under the provisions of the Budapest Treaty under accession number ATCC 40938.

III. DNA Delivery Process

Tissue from the maize embryogenic callus line AB63S was subcultured 3 weeks prior to microprojectile bombardment. The tissue was prepared for bombardment by sieving it through a 1.9 mm screen. The sieved tissue was plated onto sterile 5.5 cm Whatman No. 1 filter disks as a thin lawn of approximately 500 mg of tissue per filter disk. A total of 6 disks of tissue were prepared. Prior to microprojectile bombardment the filter disks containing the tissue were transferred to empty petri plates. The tissue was dehydrated slightly by allowing the plates to stand uncovered in a laminar flow hood for 20 minutes. To prevent further dehydration of the tissue, the plates were stored in a high humidity box until used for bombardment.

The DNA used in the bombardment consisted of a 1:1:1 mixture (by weight) of the plasmids pHYGI1, pZ27Z10 and pBII221. Precipitation of the DNA onto tungsten particles was carried out as described in Example I.

The bombardments were carried out as described in Example I except that the Biolisticn PDS 1000 (DuPont) instrument was used, and no screen was placed over the tissue. The six filter disks with callus tissue were treated as follows: two filters were bombarded two times each with the DNA/tungsten preparation (potential positive treatment 2X); three filters were bombarded one time each with the DNA/tungsten preparation (potential positive treatment 1X); one filter was bombarded once with a tungsten/water suspension using the same weight of tungsten used in the DNA/tungsten bombardments (negative control treatment).

IV. Selection of Transformed Callus

After bombardment, the filter disks with callus tissue from the 2X DNA treatment were transferred to round 1 selection plates: F medium containing 15 mg/l hygromycin. Two of the filters from the 1X DNA treatment and the filter from the negative control treatment were also transferred to round 1 selection medium. The third filter from the 1X DNA treatment was transferred to F medium containing no hygromycin, for use as unselected control callus. Since this unselected control callus was potentially positive, it was only maintained for the first two rounds of selection for comparative purposes; subsequently, non-bombarded AB63S callus maintained on F medium without hygromycin was used as unselected control callus.

After five days the callus was transferred in small clumps (about 25 mg) from the filter disks onto fresh round 1 selection medium. The plating density was 10 callus clumps per plate. By this time the callus had increased approximately two-fold in weight. The unselected control callus was transferred in the same manner to F medium without hygromycin. At nineteen days post-bombardment, all of the tissue was transferred from round 1 selection medium to round 2 selection medium (F medium containing 60 mg/l hygromycin). The plating density was 14 callus clumps per plate at this transfer. The callus had increased approximately three-fold in volume during the 14 days since the previous transfer. After 23 days, all of the callus was transferred from round 2 selection medium to round 3 selection medium containing 60 mg/l hygromycin.

At 59 days post-bombardment, five live sectors were observed proliferating among the surrounding necrotic callus clumps. These five sectors were thought to have been derived from a single callus clump from the round 2 selection, since they appeared adjacent to one another on consecutive plates from the previous transfer. These sectors arose from a 2X DNA treatment and were designated as callus line Met1.

The callus line Met1 was transferred to F medium containing 60 mg/l hygromycin and to F medium without hygromycin. After 22 days of incubation, there was no visible difference in growth or appearance of the tissue on the two types of media. The callus line Met1 grew rapidly and appeared to be uninhibited by the presence of the hygromycin in the medium. The Met1 callus appeared highly friable and embryogenic on either medium, and was visually indistinguishable from control AB63S callus grown on F medium without hygromycin.

V. Confirmation of Transformed Callus

An inhibition study was performed using Met1 callus and control AB63S callus. Prior to initiating the inhibition study, Met1 callus was grown for 21 days on F medium without hygromycin. Callus of Met1 and control AB63S callus was transferred onto plates of F medium containing 0, 15, 60, 100 and 200 mg/l hygromycin. Three plates of each callus line were prepared for each concentration of hygromycin; each plate contained 5 or 6 pieces of callus at approximately 50 mg per piece (total callus per plate was approximately 300 mg).

After 28 days of incubation, the weight of callus on each plate was measured. A measure of percent growth inhibition was determined by dividing the average weight of callus obtained at each hygromycin concentration by the average weight of callus obtained at 0 mg/l hygromycin. The results showed that the growth of Met1 callus was completely uninhibited at hygromycin concentrations of 15, 60 and 100 mg/l. The growth of Met1 callus was approximately 20% inhibited on medium containing 200 mg/l hygromycin. In contrast, the growth of AB63S callus was inhibited at all concentrations of hygromycin; at 200 mg/l hygromycin, AB63S callus was 90% inhibited in growth. These results confirmed that the callus line Met1 exhibited resistance to the presence of hygromycin in the growth medium.

Southern blot analysis was carried out to verify the presence of the hygromycin resistance gene in Met1 callus DNA and to determine whether the callus had also acquired the chimeric z27-z10 gene. For detection of the HPT coding sequence, DNA samples isolated from Met1 callus and from control callus were digested with the restriction enzymes BamHI, HindIII and BstEII. The digested DNA samples were subjected to electrophoresis on a 0.8% agarose gel and blotted to a Nytran membrane as described in Example I. Visual inspection of the ethidium bromide-stained gel prior to blotting indicated that the BamHI digestions appeared to be complete, whereas neither HindIII nor BstEII cleaved the DNA samples to a significant degree. The blot was probed with a biotin-labeled 1.05 kb BamHI fragment from the HPT coding sequence. The conditions used for hybridization, washing and detection were as suggested in a BRL Photogenel kit used in this experiment.

After hybridization, labeled bands were observed in the lanes containing BamHI digested Met1 DNA at the expected size of 1.05 kb as well as at sizes of approximately 2.7, 4.5 and 6.5 kb. This result showed that the HPT coding sequence was present in DNA from the callus line Met1. The additional bands at 2.7, 4.5 and 6.5 kb indicated that either the restriction enzyme digestion was incomplete, or that multiple rearranged copies of the HPT sequence were present. For the HindIII and BstEII digests, hybridization signals were visible in both lanes at the position of undigested DNA. This result indicated that the HPT coding sequence was integrated into high molecular-weight DNA in the Met1 genome. No hybridization signals were observed in any of the lanes containing digestions of DNA from control callus.

For detection of the chimeric z27-z10 gene, Southern blot analysis was carried out using DNA samples isolated from Met1 callus and control callus. The DNA samples were digested with the restriction enzymes BamHI and EcoRI. A BamHI digestion liberates a 2.76 kb fragment containing the z10 coding sequence and 3' noncoding sequence from the pZ27Z10 construction used in this transformation. There is a single EcoRI site in the 7.26 kb pZ27Z10 plasmid. The blot prepared was hybridized with a biotin-labeled probe containing the entire z10 coding sequence, using the conditions described in a Photogene kit (BRL).

For the BamHI digestions, endogenous z10 sequences gave hybridization signals at 9 kb and at approximately 15 kb in the lanes containing both Met1 and control callus DNAs. An additional band was observed at approximately 3.5 kb in the Met1 sample but not in the control DNA samples. No strong hybridization signal was observed at the expected 2.76 kb size in Met1 DNA. The lack of a labeled band of 2.76 kb in the BamHI digestion of Met1 DNA indicated either incomplete digestion of the DNA, or rearrangement of the introduced DNA.

For the EcoRI digestions, endogenous z10 sequences gave hybridization signals at approximately 12 kb and 16 kb in both Met1 and control callus DNAs. An additional band was observed at approximately 14 kb in the Met1 sample but not in the control callus DNA samples. These results indicated that novel z10 sequences were present in DNA from Met1 callus that were absent from control callus DNA samples.

These results were confirmed by a second Southern blot analysis in which Met1 and control callus DNAs were digested with BamHI, NcoI and NsiI. Also included were samples of undigested DNA from Met1 and control callus. The filter was probed with a $^{32}$P-labeled z10 coding sequence probe. In all of the digestions, novel z10 hybridization signals were observed in Met1 callus DNA that were absent in the negative control callus DNA samples. These results confirmed that novel z10 coding sequences were present in the Met1 callus. In the lanes containing undigested DNA, hybridization signals were observed at the position of undigested DNA from both Met1 and control callus. These results indicated that the introduced z10 sequences were integrated into chromosomal DNA in Met1 callus.

VI. Plant ReQeneration and Production of Transgenic Seed

Callus from the line Met1 and from the control line AB63S was placed on RM5 medium as described in Example I. After 14 days of incubation at 26° C. in the dark, the callus was transferred to R5 medium as in Example I. The callus was incubated at 26° C. in the dark for 7 days, and then transferred to the light under the conditions described in Example I. After 14 days in the light, plantlets were transferred to Magenta boxes (Sigma Chemical Co.) containing 100 ml of R5 medium. After 7–14 days on this medium, plantlets were transferred to vermiculite for 7 days and then to soil where they were grown to maturity. A total of 49 plants (designated Met1-1 through Met1-49) were regenerated from Met1 callus, and a total of 25 plants were regenerated from control AB63S callus.

Figure 8:
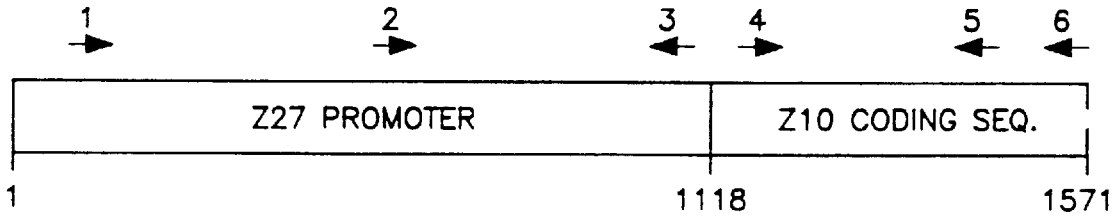
FIG. 8 is a schematic depiction of the location of the PCR primers within the chimeric z27-z10 gene.

PCR analysis was carried out on samples of DNA prepared from leaf tissue to verify that the plants regenerated from Met1 callus had retained the introduced DNA. For this purpose, a set of six oligodeoxyribonucleotides were used. The sequences of these oligonucleotides, their orientations and relative positions within the chimeric z27-z10 gene construction shown in FIG. 8 are summarized in Table 5 below.

TABLE 5

| I. | OLIGONUCLEOTIDE NAMES/POSITIONS IN CHIMERIC Z27-Z10 GENE: | | |
|---|---|---|---|
| 1. | Z27-5' | nt | 132–1566 |
| 2. | Z27-MID | nt | 628–651 |
| 3. | Z27-3' | nt | 1081–1104 |
| 4. | Z10-5' | nt | 1182–1206 |
| 5. | Z10-MID | nt | 1420–1444 |
| 6. | Z10-3' | nt | 1548–1571 |

TABLE 5-continued

| II. | AMPLIFIED FRAGMENT SIZES FROM OLIGONUCLEOTIDE PAIRS: | |
|---|---|---|
| A. | ENDOGENOUS OR CHIMERIC GENE PAIRS: | |
| | (1) + (3) | 972 BP |
| | (2) + (3) | 476 BP |
| | (4) + (6) | 389 BP |
| | (4) + (5) | 262 BP |
| B. | CHIMERIC GENE-SPECIFIC PAIRS: | |
| | (1) + (6) | 1439 BP |
| | (1) + (5) | 1312 BP |
| | (2) + (6) | 943 BP |
| | (2) + (5) | 816 BP |

The set of oligonucleotides (or primers) was designed such that the use of a pair of oligonucleotides consisting of one z27 oligonucleotide (z275' or z27mid) and one z10 oligonucleotide (z10mid or z103') would result in amplification of fragments from the chimeric z27-z10 gene only, and not from endogenous maize z27 or z10 genes. The appearance of amplified fragments of the expected sizes in PCR reactions using these z27-z10-specific oligonucleotide pairs were diagnostic for the presence of the chimeric z27-z10 gene in a particular callus or plant DNA sample.

The use of a pair of z27 oligonucleotides (z275' or z27mid with z273') or a pair of z10 oligonucleotides (z105' with z10mid or z103') resulted in amplification of fragments representing z27 regulatory sequences or z10 coding sequences, respectively, when used in PCR reactions carried out with control AB63S callus DNA, Met1 callus DNA or pZ27Z10 plasmid DNA. These reactions served as positive controls for amplification of endogenous maize gene sequences from a particular callus or plant DNA sample.

Leaf DNA was prepared from two Met1 R0 plants (designated Met1-1 and Met1-2) and from one control AB63S R0 plant as described hereinbelow. PCR reactions were carried out with these DNA samples using the oligonucleotide pairs specific for the HPT coding sequence, the chimeric z27-z10 gene, the z27 regulatory sequence and the z10 coding sequence. Gel analysis of the PCR reaction products showed that the expected size amplification products were obtained in all reactions using Met1-1 DNA and Met1-2 DNA. Control AB63S DNA was negative for the HPT coding sequence and for the chimeric z27-z10 gene, but positive for the endogenous z27 regulatory sequence and z10 coding sequence. These results demonstrated that the Met1 R0 plants examined had retained the introduced HPT DNA and the chimeric z27-z10 DNA.

As corroborative proof that the diagnostic z27-z10 PCR reaction products contained both z27 regulatory sequences and z10 coding sequences, Southern blot analysis was carried out on the PCR reaction products. Southern blot filters were prepared from two agarose gels loaded with identical samples. The samples contained the PCR reaction products resulting from amplification of z27 regulatory sequences, z10 coding sequences, and chimeric z27-z10 gene sequences described above. One blot was hybridized with a z10 coding sequence probe and the other blot was hybridized with a z27 regulatory sequence probe. The results showed that the z10 coding sequence probe hybridized to the amplified fragments from the z10 coding sequence PCR reactions and the chimeric z27-z10 gene PCR reactions, but not to the amplified fragments from the z27 regulatory sequence PCR reactions. Analogously, the z27 probe hybridized to the amplified fragments from the z27 regulatory sequence PCR reactions and the chimeric z27-z10 gene PCR reactions but not to the amplified fragments from the z10 coding sequence PCR reactions. These results demonstrated that the fragments amplified in the PCR reactions contained the expected gene sequences and that the diagnostic PCR amplification product for the chimeric z27-z10 gene contained both z27 regulatory sequences and z10 coding sequences.

Controlled pollinations of mature Met1 R0 plants were carried out with inbred maize lines A188, B73, A654 and H99. In addition, several self- and sib-pollinations were carried out. A total of 130 pollinations were carried out, using Met1 R0 plants as both male pollen donors and as female pollen recipients. Mature seed was harvested at 45 days post-pollination and allowed to dry further for 1–2 weeks.

VII. Analysis of the R1 progeny

The presence of the HPT sequence and the chimeric z27-z10 gene were evaluated by PCR analysis of DNA from R1 plant tissues, in three sets of R1 progeny.

The first set of R1 progeny analyzed consisted of four immature tassel-seeds from R0 plant Met1-7. These tassel-seeds were obtained through open pollination of silks developing from the tassel of Met1-7. Approximately 18 days after pollination, the tassel-seeds were removed from the plant and surface-sterilized. The endosperm from each seed was excised and frozen on dry ice and stored at −70° C. until used for DNA isolation.

The embryo from each seed was transferred to R5 medium and allowed to germinate. After 10 days, the seedlings were transferred to vermiculite for 7 days and then to soil, where they were allowed to grow to maturity. PCR analysis was carried out on DNA isolated from each endosperm using oligonucleotide sets specific for the HPT coding sequence, the chimeric z27-z10 gene and the maize Adh-1 gene. Three of the four endosperm DNA samples were found to be positive for all of the above gene sequences. The fourth endosperm DNA sample was negative for the HPT coding sequence and the chimeric z27-z10 gene sequence but positive for the endogenous Adh-1 sequence. These results showed that both the HPT sequence and the chimeric z27-z10 gene had been transmitted to R1 progeny of Met1-7.

A similar analysis was carried out with 24 seeds from the cross A654 X Met1-1. At 24 days after pollination, the seeds were removed from the ear and surface-sterilized. Endosperms and embryos were isolated and treated as described above. PCR analysis of the endosperm DNA samples showed that 9 of the 24 progeny had received both the HPT sequences and the chimeric z27-z10 gene. The remaining 15 progeny carried neither of the introduced gene sequences. The third set of R1 progeny analyzed consisted of 28 R1 plants derived from self-pollination of R0 plant Met1-6. DNA samples were prepared from leaf tissue of 28 two-week old seedlings.

PCR analysis of the leaf DNA samples showed that 24 of the R1 progeny carried both the HPT sequences and the chimeric z27-z10 gene. The remaining 4 R1 progeny carried neither of the introduced gene sequences. The results of the analyses described above are summarized in Table 6 and demonstrate that a significant proportion of the R1 progeny of Met1 plants inherited the introduced DNA.

TABLE 6

Inheritance of the Introduced HPT Sequences and the Chimeric Z10 Gene in Progeny from Crosses of Met1 Plants

| (A654 × Met1-1) Genotype | Outcross (Met1-6) No. Progeny | Self-Pollination No. Progeny |
|---|---|---|
| HPT+/z27z10+ | 9/24 | 24/28 |
| HPT+/z27z10− | 0/24 | 0/28 |
| HPT−/z27z10+ | 0/24 | 0/28 |
| HPT−/z27z10− | 15/24 | 4/28 |

The ratio of z27z10+/HPT+ plants to z27z10-/HPT-plants from the outcross population is consistent with a 1:1 segregation ratio of a single locus. In addition, the 35 ratio of z27z10+/HPT+plants to z27z10−/HPT− plants from the self-pollinated population is consistent with a 3:1 segregation ratio of a single locus. The data also indicate linkage of the introduced HPT and z27-z10 sequences.

EXAMPLE III

Fertile Transgenic Plants from Callus Line AB12 Containing Recombinant DNA Encoding an Insecticidal Protein The proteins encoded by the various *Bacillus thuringiensis* genes have been shown to be useful in a number of pesticidal applications. Production of transgenic maize plants with specific heterologous Bt genes may improve the resistance of the plants to specific pests. Fertile transgenic plants containing a recombinant Bt gene were prepared according to the procedure of Example I, with several minor modifications, as indicated below.

The plasmid pHYGI1 described in Example I was used, as well as pMS533, which is a plasmid that contains the insecticidal *Bacillus thuringiensis* endotoxin (BT) gene fused in frame with the neomycin phosphotransferase (NPTII) gene. At a position 5' from the fusion gene-are located segments of DNA from the CaMV and nopaline synthase promoters. At a position 3' from the fusion gene are segments of DNA derived from the tomato protease inhibitor I gene and the poly A region of the nopaline synthase gene.

AB12 callus was bombarded as described in Example I except that the DNA used in the tungsten/DNA preparations contained plasmids pHYGI1 and pMS533. One tube contained only 5 $\mu$l TE (10 mM Tris-HCl pH 8.0, 1 mM EDTA).

The following bombardments were done: 11×TE pHYGI1/pMS533 (potential positive treatment) and 3×TE prep (control treatment).

After bombardment, the callus from the pHYGI1/pMS533 treatments was placed onto round 1 selection plates, F medium containing 15 mg/l hygromycin as ten pieces per plate. The same was done for two of the plates bombarded with the TE preparation (selected control callus). One plate of callus bombarded with the TE preparation was placed onto F medium with no hygromycin; this callus was maintained throughout the experiment as a source of control tissue (unselected control callus).

After 18 days, the callus was transferred from round 1 selection plates to round 2 selection plates containing 60 mg/l hygromycin as ten 30 mg pieces per plate. After 21 days of selection on round 2 selection plates, the callus appeared completely inhibited. All of the callus was transferred from round 2 selection plates to round 3 selection plates containing 60 mg/l hygromycin.

After 42 days on round three selection plates, six sectors were observed proliferating from the surrounding necrotic tissue, all were from pHYGI1/pMS533-treated material. The callus lines were transferred to F medium.

After 24 days, one callus line, designated CB2, had grown substantially. Portions of each callus line were then transferred to (i) F medium containing 15 mg/l hygromycin, or (ii) F medium containing 60 mg/l hygromycin. Control callus was plated on F medium with 15 mg/l hygromycin.

Only one of the six callus lines, CB2, was capable of sustained growth through multiple subcultures in the presence of 60 mg/l hygromycin. DNA was isolated from portions of this callus and the presence of the Bt gene was confirmed by Southern blot analysis.

DNA was digested with the restriction enzymes BamHI and XhoI in combination. BamHI cuts at the 5' end of the Bt coding sequence and XhoI cuts at the 3' end of the coding region. A $^{32}$p labeled probe was prepared from the 1.8 kb BamHI/XhoI restriction fragment of pMS533. The predicted 1.8 kb band was observed after hybridization and autoradiography. No bands were observed in the DNA from the untransformed callus.

Plants were regenerated from CB2 and controlled pollinations were performed to yield the R1 generation, as described hereinabove. R1 plants were tested for the presence of the HPT and Bt gene sequences by PCR analysis, and for HPT gene expression by enzyme assay as described in Example I.

PCR analysis was performed on DNA isolated from root tissue of R1 seedlings by the methods described in Example I. To test that each DNA sample was competent for PCR, PCR analysis was carried out using primers specific for the native maize 10 kD zein gene. The primers used for PCR analysis of the Bt gene were one complementary to the 35S promoter and one complementary to the Bt coding sequence. Primers used for HPT PCR analysis were the same as those described in Example I. The results of this analysis are presented in Table 7. The results show transmission of the introduced HPT and Bt genes through both the male and female parents and the observed frequencies are consistent with Mendelian inheritance. The results are consistent with the insertion of the HPT and Bt genes into chromosomal DNA. It was also found that the HPT and Bt genes show a linked inheritance, indicating that the two genes are inserted close together on the same chromosome.

TABLE 7

Analysis of R1 Progeny of CB2

| Plant | 10Kd PCR | HPT PCR | BT PCR | HPT ENZ. | Plant | 10Kd PCR | HPT PCR | BT PCR | HPT ENZ. |
|---|---|---|---|---|---|---|---|---|---|
| A. Transgenic CB2.8 × FR4326 Analysis | | | | | Control AB12.7 × FR4326 Analysis | | | | |
| 1 | + | + | + | + | 1 | + | − | − | − |
| 2 | + | + | + | + | 2 | + | − | − | − |
| 3 | + | − | − | − | | | | | |
| 4 | + | + | + | + | | | | | |
| 5 | + | + | + | + | | | | | |
| 6 | + | − | − | − | | | | | |
| 7 | + | + | + | + | | | | | |
| 8 | + | − | − | − | | | | | |
| 9 | + | + | + | + | | | | | |
| 10 | + | − | − | − | | | | | |

TABLE 7-continued

Analysis of R1 Progeny of CB2

| Plant | 10Kd PCR | HPT PCR | BT PCR | HPT ENZ. | Plant | 10Kd PCR | HPT PCR | BT PCR | HPT ENZ. |
|---|---|---|---|---|---|---|---|---|---|
| B. Transgenic CB2.11 × LB101 Assays | | | | | Control AB12.4 × LB101 Assays | | | | |
| 1 | + | − | − | − | 1 | + | − | − | − |
| 2 | + | + | + | + | 2 | + | − | − | − |
| 3 | + | − | − | − | | | | | |
| 4 | + | + | + | + | | | | | |
| 5 | + | − | − | − | | | | | |
| 6 | + | + | + | + | | | | | |
| 7 | + | − | − | − | | | | | |
| 8 | + | − | − | − | | | | | |
| 9 | + | − | − | − | | | | | |
| 10 | + | − | − | + | | | | | |
| C. Transgenic CB2.7 × LM1112 Assays | | | | | Control AB12.5 × LM1112 Assays | | | | |
| 1 | + | − | − | | 1 | + | − | − | |
| 2 | + | + | + | | 2 | + | − | − | |
| 3 | + | − | − | | | | | | |
| 4 | + | − | − | | | | | | |
| 5 | + | + | + | | | | | | |
| 6 | + | + | + | | | | | | |
| 7 | + | + | + | | | | | | |
| 8 | + | + | + | | | | | | |
| 9 | + | − | − | | | | | | |
| 10 | + | − | − | | | | | | |
| D. Transgenic FR4326 × CB2.9 Assays | | | | | Control FR4326 × AB12.1 Assays | | | | |
| 1 | + | − | − | | 1 | + | − | − | |
| 2 | + | + | + | | 2 | + | − | − | |
| 3 | + | + | + | | | | | | |
| 4 | + | + | + | | | | | | |
| 5 | + | + | + | | | | | | |
| 6 | + | − | − | | | | | | |
| 7 | + | + | + | | | | | | |
| 8 | + | + | + | | | | | | |
| 9 | + | − | − | | | | | | |
| 10 | + | − | − | | | | | | |
| E. Transgenic A188 × CB2.1 Assays | | | | | Control A188 × AB12.2 Assays | | | | |
| 1 | + | + | + | | 1 | + | − | − | |
| 2 | + | + | + | | 2 | + | − | − | |
| 3 | + | + | + | | | | | | |
| 4 | + | − | − | | | | | | |
| 5 | + | + | + | | | | | | |
| 6 | + | − | − | | | | | | |
| 7 | + | + | + | | | | | | |
| 8 | + | + | + | | | | | | |
| 9 | + | − | − | | | | | | |
| 10 | + | − | − | | | | | | |
| F. Transgenic LM1112 × CB2.2 Assays | | | | | Control LM112 × AB12.6 Assays | | | | |
| 1 | + | − | − | | 1 | + | − | − | |
| 2 | + | − | − | | 2 | + | − | − | |
| 3 | + | − | − | | | | | | |
| 4 | + | − | − | | | | | | |
| 5 | + | − | − | | | | | | |
| 6 | + | − | − | | | | | | |
| 7 | + | − | − | | | | | | |
| 8 | + | + | + | | | | | | |

EXAMPLE IV

Fertile Transgenic Plants from Callus Line AB12 Transmitting Recombinant DNA through Two Complete Sexual Cycles

I. Plant Lines and Tissue Culture

The callus line AB12 was used, and is described in Example I.

II. Plasmids

The plasmids pBII221 and pHYGI1 described in ample I were used.

III. DNA Delivery Process

Callus was bombarded as in Example I, except that the DNA used in the tungsten/DNA preparations differed. All of the tubes contained 25 $\mu$l 50 mg/ml M-10 tungsten in water, 25 $\mu$l 2.5 M $CaCl_2$, and 10 $\mu$l 100 mM spermidine along with a total of 5 $\mu$l 1 mg/ml total plasmid content. One tube contained only plasmid pBII221; two tubes contained only plasmid pHYGI1; and one tube contained no plasmid but 5 $\mu$l TE buffer.

The following bombardments were done: 2×pBII221 prep (for transient expression); 7×pHYGI1 prep (potential positive treatment); and 3×TE prep (negative control treatment).

After all the bombardments were performed, the callus from the pBII221 treatment was transferred plate for plate to F medium as five 50 mg pieces. After 2 days, the callus was placed into GUS assay buffer as per Example I. Numbers of transiently expressing cells were counted and found to be 686 and 845 GUS positive cells, suggesting that the particle delivery process had occurred in the other bombarded plates.

IV. Selection of Transformed Callus

After bombardment, the callus from the pHYGI1 treatments was placed onto round 1 selection plates, F medium containing 15 mg/l hygromycin, as ten 25 mg pieces per plate. The same was done for two of the plates bombarded with the TE preparation (selected control callus). One plate of callus bombarded with the TE preparation was placed onto F medium with no hygromycin; this callus was maintained throughout the experiment as a source of control tissue (unselected control callus).

After 13 days, the callus on round 1 selection plates was indistinguishable from unselected control callus. All of the callus was transferred from round 1 selection plates to round 2 selection plates containing 60 mg/l hygromycin. An approximate five-fold expansion of the numbers of plates occurred.

The callus on round 2 selection plates had increased substantially in weight after 23 days, but at this time appeared close to necrotic. All of the callus was transferred from round 2 selection plates to round 3 selection plates containing 60 mg/l hygromycin.

At 58 days post-bombardment, three live sectors were observed proliferating from the surrounding dead tissue. All three lines were from pHYGI1 treatments and were designated 24C, 56A, and 55A.

After 15 days on maintenance medium, growth of the lines was observed. The line 24C grew well whereas lines 55A and 56A grew more slowly. All three lines were transferred to F medium containing 60 mg/l hygromycin. Unselected control callus from maintenance medium was also plated to F medium containing 60 mg/l hygromycin.

After 19 days on 60 mg/l hygromycin, the growth of line 24C appeared to be entirely uninhibited, while the control showed approximately 80% of the weight gain of 24C. The line 56A was completely necrotic, and the line 55A was very close to necrotic. The lines 24C and 55A were transferred again to F medium containing 60 mg/l hygromycin, as was the control tissue.

After 23 days on 60 mg/l hygromycin, the line 24C again appeared entirely uninhibited. The line 55A was completely dead, as was the negative control callus on its second exposure to F medium having 60 mg/l hygromycin.

V. Confirmation of Transformed Callus

Figure 6:
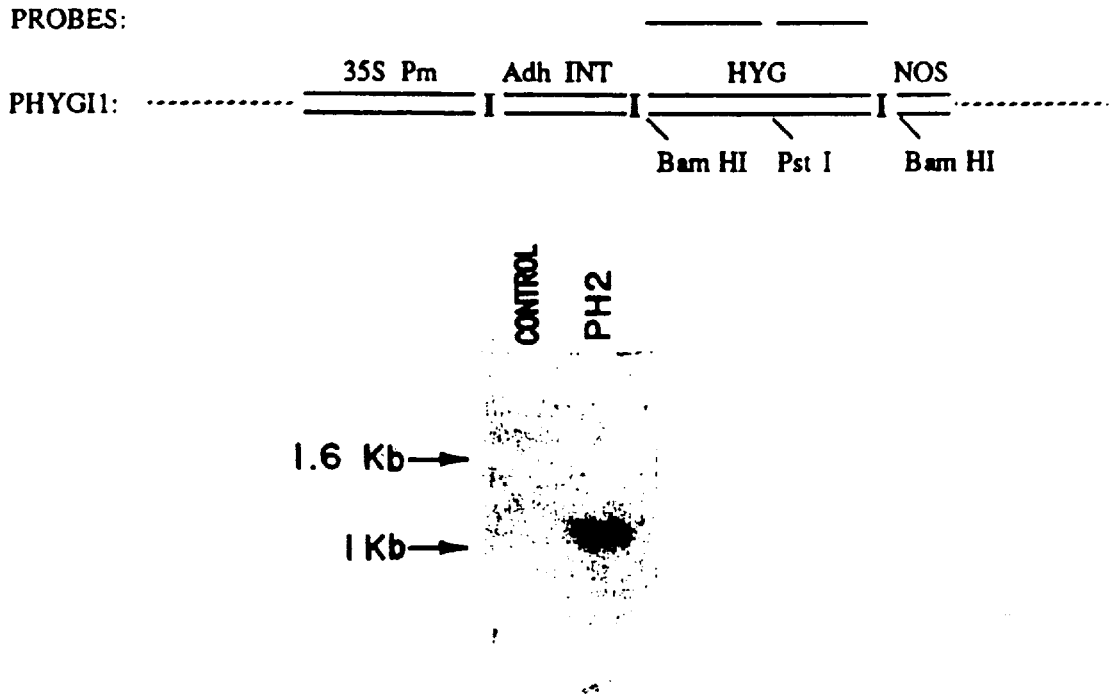
FIG. 6 is a Southern blot of DNA isolated from the PH2 callus line and an untransformed control callus line, and a schematic depiction of the pHYGI1 probes used in the assay.

A Southern blot was prepared from BamHI-digested DNA from the line 24C and probed with the HPT probe described in Example I. As shown in FIG. 6, a band was observed for the line 24C at the expected size of 1.05 kb showing that the line 24C contained the HPT coding sequence. No band was observed for DNA from control tissue. The name of the callus line 24C was changed to PH2.

To demonstrate that the hygromycin gene is incorporated into high molecular weight DNA, DNA isolated from PH2 callus and control callus was treated with (i) no restriction enzyme, (ii) BamHI, as described previously, or, (iii) PstI, which cuts the plasmid pHYGI1 only once within the HPT coding sequence. Samples were blotted and probed with the HPT coding sequence as described previously.

Undigested PH2 DNA only showed hybridization the probe at the position of uncut DNA, demonstrating that the hygromycin gene is incorporated into high molecular weight DNA. The expected 1.05 kb band for PH2 DNA digested with BamHI was observed, as had been shown previously. For PH2 DNA digested with PstI, a 5.9 kb band would be expected if the hygromycin gene was present on an intact pHYGI1 plasmid. Two or more bands of variable size (size dependent on the position of flanking PstI sites within the host DNA) would be expected if the gene was integrated into genomic DNA. Two bands were observed with approximate molecular sizes of 6.0 and 3.0 kb. These data are consistent with incorporation of the hygromycin gene into high molecular weight DNA. No hybridization was observed for DNA from control callus in any of the above treatments.

These results demonstrate that the HPT coding sequence is not present in PH2 callus as intact pHYGI1 or as a small non-chromosomal plasmid. They are consistent with incorporation of the hygromycin gene into high molecular weight DNA. Further Southern blot analyses demonstrated that the HPT coding sequence is contiguous with the 35S promoter sequence.

VI. Plant Reqeneration and Production of Seed

The line PH2, along with unselected control callus, was placed onto RM5 medium to regenerate plants as in Example I. After 16 days, the callus was transferred to R5 medium as in Example I. After 25 d on R5 medium, plantlets were transferred to R5 medium and grown up for 20 days. At this point, plantlets were transferred to vermiculite for one week and then transplanted into soil where they were grown to sexual maturity. Controlled pollinations were then performed with the inbred line B73.

VII. Analysis of R1 progeny

A. PH2 as Pollen Donor

Ten R1 progeny plants from a B73 X PH 2.6 cross were assayed for HPT expression with both root elongation and etiolated leaf assays. One positive plant was identified. The presence of the HPT gene in the positive plant was confirmed by Southern blot analysis employing the HPT probe as described in Example I.

To conduct the root elongation bioassay, seed was sterilized in a 1:1 dilution of commercial bleach in water plus 0.1% Alconox for 20 min. in 125 ml Erlenmeyer flasks and rinsed 3 times in sterile water. The seeds were imbibed overnight in sterile water containing 50 mg/ml Captan by shaking at 150 rpm.

After imbibition, the solution was decanted from the flasks and the seed transferred to flow boxes (Flow Laboratories) containing 3 sheets of $H_2O$ saturated germination paper. A fourth sheet of water saturated germination paper was placed on top of the seed. Seed was allowed to germinate 4 days.

After the seed had germinated, approximately 1 cm of the primary root tip was excised from each seedling and plated on medium containing MS salts, 20 g/l sucrose, 50 mg/l hygromycin, 0.25% Gelrite, and incubated in the dark at 26° C. for 4 days.

Roots were evaluated for the presence or absence of abundant root hairs and root branches. Roots were classified as transgenic (hygromycin resistant) if they had root hairs and root branches, and untransformed (hygromycin sensitive) if they had limited numbers of branches.

After the root tips were excised, the seedlings of one PH2 ear and one control ear were transferred to moist vermiculite and grown in the dark for 5 days. At this point, to conduct an etiolated leaf bioassay, 1 mm sections were cut from the tip of the coleoptile, surface sterilized 10 seconds, and plated on MS basal salts, 20 g/l sucrose, 2.5 g/l Gelrite with either 0 (control) or 100 mg/l hygromycin and incubated in the dark at 26° C. for 18 hrs. Each plate contained duplicate sections of each shoot. The plates were then incubated in a light regimen of 14 hrs light 10 hrs dark at 26° C. for 48 hrs, and rated on a scale of from 0 (all brown) to 6 (all green) for the percent of green color in the leaf tissue. Shoots were classified as untransformed (hygromycin sensitive) if they had a rating of zero and classified as transformed (hygromycin resistant) if they had a rating of 3 or greater.

B. PH2 as Pollen Recipient

80 R1 progeny plants from a PH2 plant designated PH 2.23 X B73 cross were assayed for HPT expression by root elongation assay and 26 tested positive. The expression of the HPT gene was further confirmed for all 26 by direct exposure of seedlings to hygromycin-containing medium in Flow boxes. Two of the resistant plants were analyzed by PCR, and the presence of the HPT sequence was confirmed.

VIII. Analysis of R2 Progeny

The transgenic R1 plant which had PH2 as the pollen parent was grown to maturity and used to pollinate an FR4326 plant.

R2 seeds from this cross were germinated and tested for the presence of HPT sequences by PCR. Expression of the HPT gene was determined with the HPT enzymatic assay described in Example I.

Three of the 19 progeny tested contained HPT gene sequences and also expressed the HPT enzyme activity. The remainder neither contained HPT sequences nor showed enzyme activity. This result demonstrates pollen transmission and expression of the genetically engineered DNA through 2 successive generations, indicating that the gene is stable.

EXAMPLE V

The friable, embryogenic maize callus culture AB12 described in Example I was used.

The plasmids pCHN1-1 and pLUC-1 were constructed in the vector pBS+ (Stratagene, Inc., San Diego, Calif.), a 3.2 Kb circular plasmid, using standard recombinant DNA techniques. pCHN1-1 contains the hygromycin B phosphotransferase (HPT) coding sequence from *E. coli* (Gritz et al. 1983) flanked at the 3' end by the nopaline synthase (nos) polyadenylation sequence of Agrobacterium tumefaciens (Chilton and Barnes 1983). Expression is driven by the cauliflower mosaic virus (CaKV) 35S promoter (Guilley et al. 1982), located upstream from the HPT coding sequence. The plasmids pBII221 and pHYGI1 were also used in this example. pLUC-1 contains the firefly luciferase coding sequence (DeWet et al. 1987) flanked at the 5" end by the CaMV 35S promoter and at the 3' end by the nos polyadenylation sequence. This plasmid was used solely as negative control DNA. Plasmids were introduced into AB12 by microprojectile bombardment. Twenty-six plates were prepared as described in Example I. One tube contained only plasmid pBII221; two tubes contained both plasmids pHYGI1 and pBII221; two tubes contained both plasmids pCHN1-1 and pBII221; and one tube contained only plasmid pLUC-1. The bombardments which were performed are summarized on Table 8.

TABLE 8

| | |
|---|---|
| 2 × pBII221 prep | To determine transient expression frequency |
| 10 × pCHN1-1/pBII221 | As a potential positive treatment for transformation |
| 10 × pHYGI1/pBII221 | As a potential positive treatment for transformation |
| 4 × pLUC-1 | Negative control treatment |

The two plates of callus bombarded with pBII221 were assayed for transient GUS expression. The number of blue cells was counted, giving 291 and 477 transient GUS expressing cells in the two plates, suggesting that the DNA delivery process had also occurred with the other bombarded plates.

Immediately after all samples had been bombarded, callus from all of the plates treated with pHYGI1/pBII221, pCHN1-1/pBII221 and three of the plates treated with pLUC-1 were transferred plate for plate onto round 1 selection plates, F medium containing 15 mg/l hygromycin B, (five pieces of callus per plate). Callus from the fourth plate treated with pLUC-1 was transferred to F medium without hygromycin. This tissue was subcultured every 2–3 weeks onto nonselective medium and is referred to as unselected control callus.

After two weeks of selection, tissue appeared essentially identical on both selective and nonselective media. All callus from eight plates from each of the pHYGI1/pBII221 and pCHN1-1/pBII221 treatments and two plates of the control callus on selective media were transferred from round 1 selection plates to round 2 selection plates that contained 60 mg/l hygromycin. The round 2 selection plates each contained ten 30 mg pieces of callus per plate, resulting in an expansion of the total number of plates.

The remaining tissue on selective media, two plates each of pHYGI1/pBII221 and pCHN1-1/pBII221 treated tissue and one of control callus, were placed in GUS assay buffer at 37° C. to determine whether blue clusters of cells were observable at two weeks post-bombardment. After 6 days in assay buffer, this tissue was scored for(,GUS expression. The results are summarized on Table 9.

TABLE 9

| Treatment | Replicate | Observations |
|---|---|---|
| pLUC-1 | | No blue cells |
| pHYGI1/pBI1221 | Plate 1 | 11 single cells |
| | | 1 four-cell cluster |
| | Plate 2 | 5 single cells |
| pCHN1-1/pEII221 | Plate 1 | 1 single cell |
| | | 2 two-cell clusters |
| | Plate 2 | 5 single cells |
| | | 1 two-cell cluster |
| | | 2 clusters of 8–10 cells |

After 21 days on the round 2 selection plates, all viable portions of the material were transferred to round 3 selection plates containing 60 mg/l hygromycin. The round 2 selection plates, containing only tissue that was apparently dead, were reserved. Both round 2 and 3 selection plates were observed periodically for viable proliferating sectors.

After 35 days on round 3 selection plates, both the round 2 and round 3 sets of selection plates were checked for viable sectors of callus. Two such sectors were observed proliferating from a background of dead tissue on plates treated with pHYGI1/pBII221. The first sector named 3AA was from the round 3 group of plates and the second sector named PH1 was from the round 2 group of 15 plates. Both lines were then transferred to F medium without hygromycin.

After 19 days on F medium without hygromycin, the line 3AA grew very little whereas the line PH1 grew rapidly. Both were transferred again to F medium for 9 days. The lines 3AA and PH1 were then transferred to F medium containing 15 mg/l hygromycin for 14 days. At this point, line 3AA was observed to be of very poor quality and slow growing. The line PH1, however, grew rapidly on F medium with 15 mg/l hygromycin; the line was then subcultured to F medium without hygromycin.

After 10 days on F medium, an inhibition study of the line PH1 was initiated. Callus of PH1 was transferred onto F medium containing 1, 10, 30, 100, and 250 mg/l hygromycin B. Five plates of callus were prepared for each concentration and each plate contained ten approximately 50 mg pieces of callus. One plate of unselected control tissue was prepared for each concentration of hygromycin.

It was found that the line PH1 was capable of sustained growth over 9 subcultures on 0, 10, 30, 100, and 250 mg/l hygromycin.

Additional sectors were recovered at various time points from the round 2 and 3 selection plates. None of these were able to grow in the presence of hygromycin for multiple rounds, i.e., two or three subcultures.

To show that the PH1 callus had acquired the hygromycin resistance gene, a Southern blot of PH1 callus was prepared by isolating DNA from PH1 and unselected control calli by freezing 2 g of callus in liquid nitrogen and grinding it to a fine powder which was transferred to a 30 ml Oak Ridge tube containing 6 ml extraction buffer (7M urea, 250 mM NaCl, 50 mM Tris-HCl pH 8.0, 20 mM EDTA pH 8.0, 1% sarcosine). To this was added 7 ml of phenol:-chloroform 1:1, the tubes shaken and incubated at 37° C. for 15 min. Samples were centrifuged at 8K for 10 min. at 40° C. The supernatant was-pipetted through miracloth (Calbiochem 475855) into a disposable 15 ml tube (American Scientific Products, C3920-15A) containing 1 ml 4.4 M ammonium acetate, pH 5.2. Isopropanol, 6 ml was added, the tubes shaken, and the samples incubated at −20° C. for 15 min. The DNA was pelleted in a Beckman TJ-6 centrifuge at the maximum speed for 5 min. at 40° C. The supernatant was discarded and the pellet was dissolved in 500 μl TE-10 (10 mM Tris-HCl pH 8.0, 10 mM EDTA pH 8.0) 15 min. at room temperature. The samples were transferred to a 1.5 ml Eppendorf tube and 100 μl 4.4 M ammonium acetate, pH 5.2 and 700 μl isopropanol were added. This was incubated at −20° C. for 15 min. and the DNA pelleted 5 min. in an Eppendorf microcentrifuge (12,000 rpm). The pellet was washed with 70% ethanol, dried, and resuspended in TE-1 (10 mM Tris-HCl pH 8.0, 1 mM EDTA).

Figure 3:
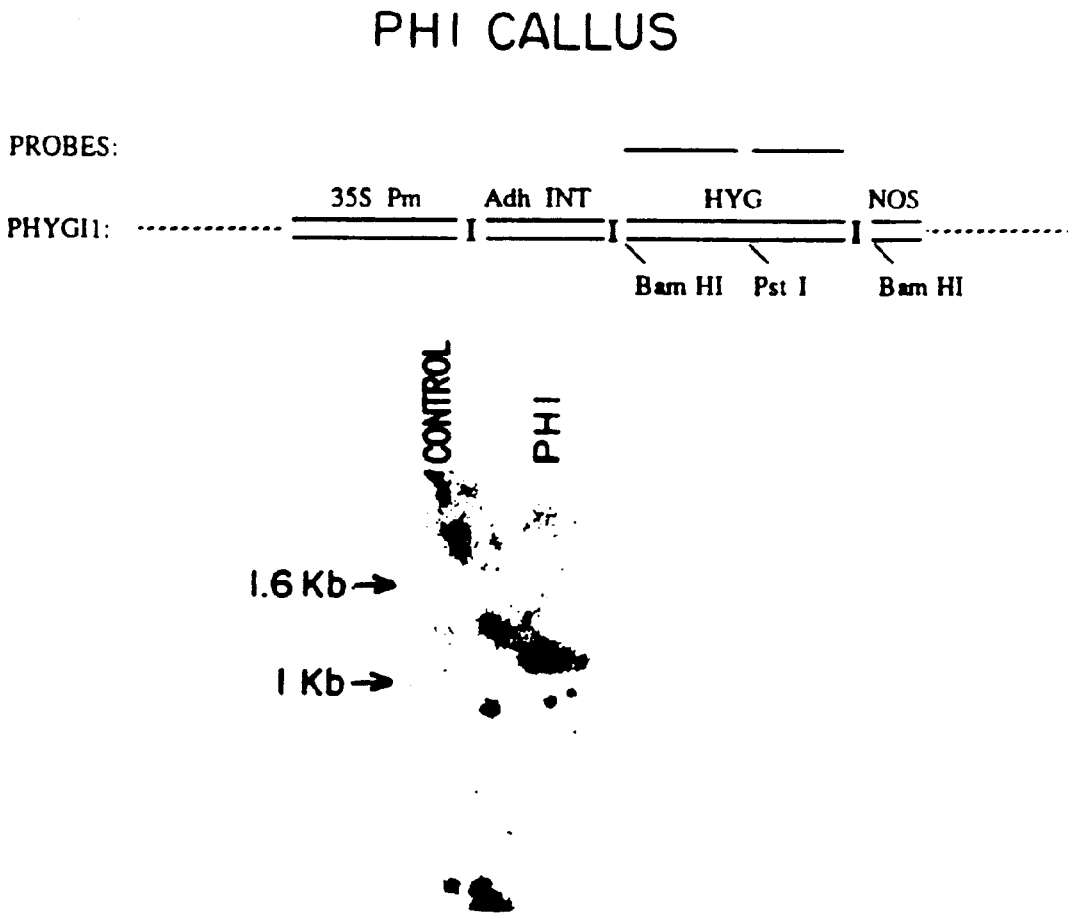
FIG. 3 is a Southern blot of DNA isolated from the PH1 callus line and an untransformed control callus line, and a schematic depiction of the pHYGI1 probes used in the assay.

Ten pg of isolated DNA were digested with BamHI (NEB) and analyzed as described in Example I using the HPT probe. As shown in FIG. 3, a band was observed for PH1 callus at the expected position of 1.05 Kb, indicating that the HPT coding sequence was present. No band was observed for control callus.

To demonstrate that the hygromycin gene is incorporated into high molecular weight DNA, DNA isolated from PH1 callus and control callus was treated with (i) no restriction enzyme, (ii) BamHI, as described previously, or (iii) PstI, which cuts the plasmid pHYGI1 only once within the HPT coding sequence. Samples were blotted and probed with the HPT coding sequence as described previously.

Undigested PH1 DNA only showed hybridization to the probe at the position of uncut DNA, demonstrating that the hygromycin gene is incorporated into high molecular weight DNA. The expected 1.05 Kb band for PH1 DNA digested with BamHI was observed, as had been shown previously. For PH1 DNA digested with PstI, a 5.9 Kb band would be expected if the hygromycin gene was present on an intact pHYGI1 plasmid. Two or more bands of variable size (size dependent on the position flanking PstI sites within the host DNA) would be expected if the gene was incorporated into high molecular weight DNA. Three bands were observed with approximate molecular sizes of 12, 5.1, and 4.9 Kb. This result demonstrates incorporation of the hygromycin gene into high molecular weight DNA. The intensity of the 4.9 Kb band is approximately twice as great as the other two bands, suggesting either partial digestion or possibly a tandem repeat of the HPT gene. No hybridization was observed for DNA from control callus in any of the above treatments.

These results demonstrate that the HPT coding sequence is not present in PH1 callus as intact PHYGI1 or as a small non-chromosomal plasmid. They are consistent with incorporation of the hygromycin gene into high molecular weight DNA. Further, Southern blot analyses demonstrated that the HPT coding sequence is contiguous with the 35S promoter sequence.

PH1 callus was transferred from all of the concentrations of hygromycin used in the inhibition study to RM5 medium and plants were regenerated as described in Example I. A total of 65 plants were produced from PH1 and a total of 30 plants were produced from control callus.

Figure 4:
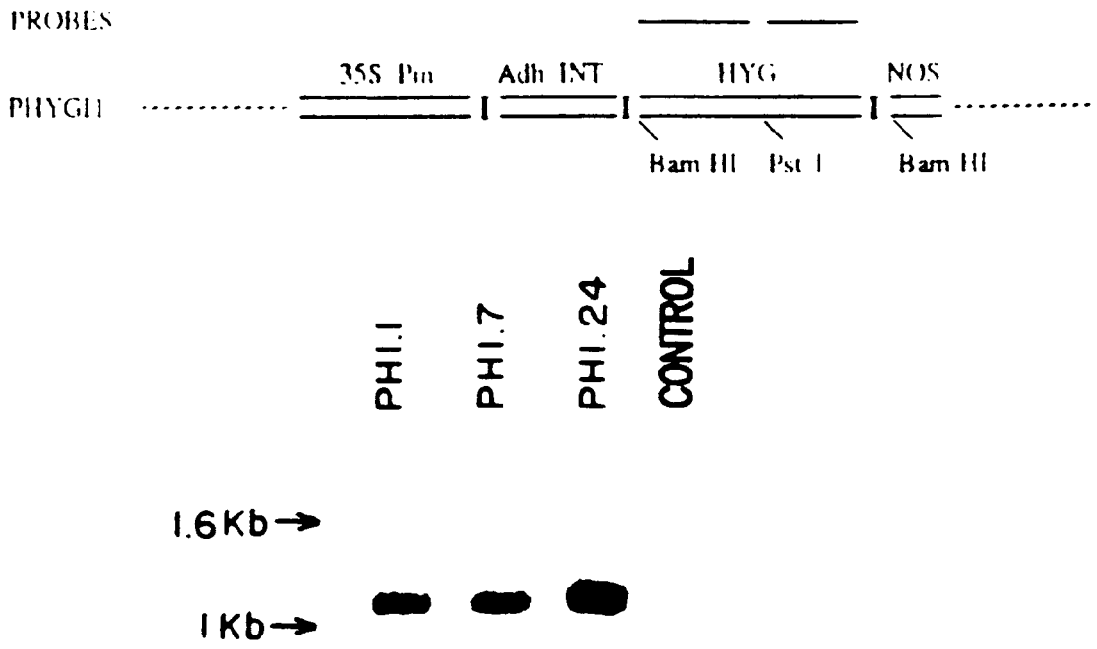
FIG. 4 is a Southern blot of leaf DNA isolated from R0 plants regenerated from PH1 and untransformed callus, and a schematic depiction of the pHYGI1 probes used in the assay.

To demonstrate that the introduced DNA had been retained in the R0 tissue, a Southern blot was performed as previously described on BamHI digested leaf DNA from three randomly chosen R0 plants of PH1. The blot was probed with the HPT probe as in Example I. As shown in FIG. 4, a 1.05 Kb band was observed with all three plants indicating that the HPT coding sequence was present. No band was observed for DNA from a control plant.

Controlled pollinations of mature PH1 plants were conducted by standard techniques with inbred *Zea mays* lines A188, B73, and Oh43. Seed was harvested 45 days post-pollination and allowed to dry further 1–2 weeks.

Figure 5:
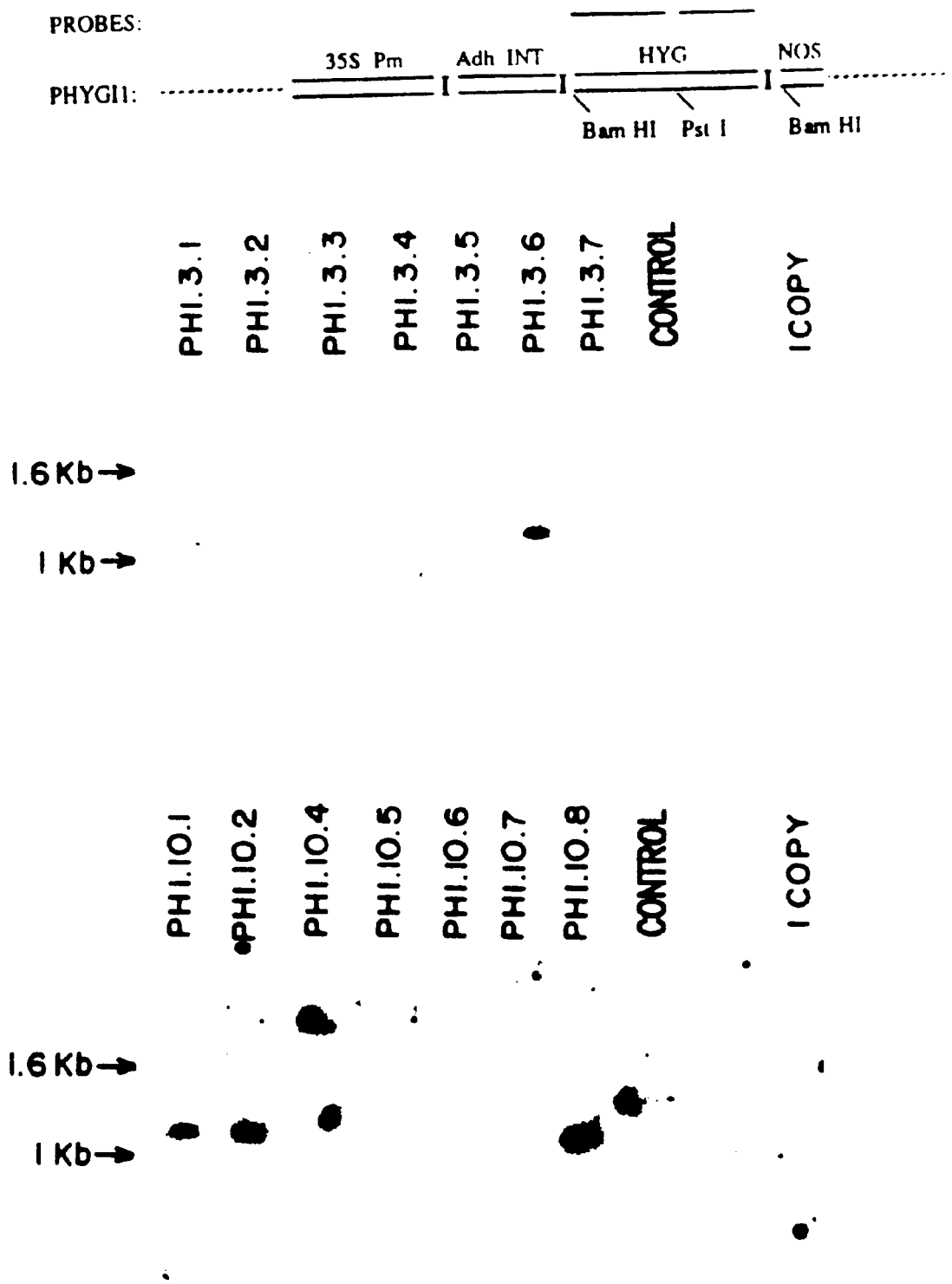
FIG. 5 is a Southern blot of leaf DNA isolated from R1 progeny of PH1 R0 plants and untransformed R0 plants, and a schematic depiction of the pHYGI1 probes used in the assay.

The presence of the hygromycin resistance trait in the R1 progeny was evaluated by the root elongation bioassay, an etiolated leaf bioassay, and by Southern blotting. Two ears each from regenerated PH1 and control plants were selected for analysis. The pollen donor was inbred line A188 for all ears. The results are shown in FIG. 5 and in Table 10, below.

TABLE 10

ANALYSIS OF PH1 R1 PLANTS

| PHI PLANT | ROOT ASSAY | LEAF ASSAY | BLOT | CONT PLANT | ROOT ASSAY | LEAF ASSAY | BLOT |
|---|---|---|---|---|---|---|---|
| 3.1 | + | ND | + | 4.1 | – | ND | ND |
| 3.2 | – | ND | – | 4.2 | – | ND | ND |
| 3.3 | – | ND | – | 4.3 | – | ND | ND |
| 3.4 | – | ND | – | 4.4 | – | ND | ND |
| 3.5 | – | ND | – | 4.5 | – | ND | ND |
| 3.6 | + | ND | + | 4.6 | – | ND | ND |
| 3.7 | – | ND | – | 4.7 | – | ND | ND |
| | | | | 2.1 | – | ND | – |
| 10.1 | + | + | + | 1.1 | – | – | – |
| 10.2 | + | + | + | 1.2 | – | – | ND |
| 10.3 | – | – | ND | 1.3 | – | – | ND |
| 10.4 | – | – | – | 1.4 | – | – | ND |
| 10.5 | – | – | – | 1.5 | – | – | ND |
| 10.6 | – | – | – | 1.6 | – | – | ND |
| 10.7 | – | – | – | 1.7 | – | – | ND |
| 10.8 | ND | + | + | 1.8 | – | – | ND |

Key:
+ = transgenic;– = nontransgenic; ND = not done

The presence of the HPT gene was confirmed in two R2 progeny deriving from a PH1 maternal parent.

Plant PH1.3.1 (see Table 9) was pollinated with Oh43 pollen. Nine seeds derived from this cross were germinated, DNA was prepared from the leaves of four of the progeny plants, and analyzed by Southern blotting using the HPT coding sequence probe. Two of the four plants tested contained the HPT sequence in high copy number. Although the HPT gene was present in two of the plants, expression of the gene could not be detected in the etiolated leaf assay.

Plant PH1.10.8 (Table 9) was used to pollinate B73 and was also selfed. Fifty of the progeny from the out-cross were tested for HPT expression in both root and leaf assays. No expression was detected. Likewise Southern blots on DNA from eight of the progeny did not detect the presence of the HPT gene. In the progeny from the self cross, no evidence for the presence of the gene was obtained in leaf assays of nine progeny, or from Southern blots of the DNA from four of these plants.

The recombinant DNA was only shown to be inherited by progeny when a transgenic plant (both R0 and R1) was used as a female. This is suggestive of maternal inheritance of the recombinant DNA for PH1.

All of the publications and patent documents cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A fertile, mature, transgenic *Zea mays* plant, the genome of which has been altered by the introduction of an isolated, heterologous DNA construct, comprising a potato patatin gene, wherein said DNA construct is expressed so that the transgenic plant exhibits insect resistance that renders it identifiable over the corresponding untransformed *Zea mays* plant which does not comprise said DNA construct, and wherein the DNA is transmitted through a normal sexual cycle of the transgenic *Zea mays* plant to progeny.

2. A seed produced by the fertile, transgenic *Zea mays* plant of claim 1 which comprises said DNA construct.

3. A progeny *Zea mays* plant derived from the fertile, transgenic *Zea mays* plant of claim 1 wherein said progeny plant expresses said DNA construct so that said progeny plant exhibits said traits.

4. A seed derived from said progeny *Zea mays* plant of claim 3 wherein said seed comprises said DNA construct.

5. The fertile, transgenic *Zea mays* plant of claim 1 wherein said DNA construct further comprises a promoter.

6. The fertile, transgenic *Zea mays* plant of claims 1 or 5 wherein said DNA construct further comprises a selectable marker gene or a reporter gene.

7. The fertile, transgenic *Zea mays* plant of claim 6 wherein the selectable marker gene is neo, hpt, dhfr or bar.

8. An inbred transgenic *Zea mays* plant of claim 1.

9. A hybrid transgenic *Zea mays* plant of claim 1.

* * * * *